(12) United States Patent
Jones

(10) Patent No.: US 7,214,513 B2
(45) Date of Patent: May 8, 2007

(54) TRANSCRIPTIONAL REGULATORY FACTOR

(75) Inventor: Michael H. Jones, Niihari-mura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 84 days.

(21) Appl. No.: 10/754,342

(22) Filed: Jan. 9, 2004

(65) Prior Publication Data

US 2004/0146914 A1    Jul. 29, 2004

Related U.S. Application Data

(60) Division of application No. 09/698,295, filed on Oct. 27, 2000, now Pat. No. 6,689,584, which is a continuation-in-part of application No. PCT/JP99/02340, filed on Apr. 30, 1999.

(30) Foreign Application Priority Data

Apr. 30, 1998    (JP)    ................. 10-137631

(51) Int. Cl.
- C12P 21/02    (2006.01)
- C12N 1/21     (2006.01)
- C12N 1/19     (2006.01)
- C12N 15/63    (2006.01)
- C12N 5/10     (2006.01)
- C07H 21/04    (2006.01)

(52) U.S. Cl. ............ 435/69.1; 435/252.3; 435/254.11; 435/320.1; 435/325; 536/23.5

(58) Field of Classification Search ............... 526/23.1; 435/69.1, 320; 350/350
See application file for complete search history.

(56) References Cited

FOREIGN PATENT DOCUMENTS

| | | |
|---|---|---|
| EP | 1 033 401 A2 | 9/2000 |
| EP | 1 033 401 A3 | 9/2000 |
| WO | WO 99/10363 | 3/1999 |
| WO | WO 99/53045 | 10/1999 |
| WO | WO 00/21991 | 4/2000 |
| WO | WO 00/55320 | 9/2000 |

OTHER PUBLICATIONS

Popi Syntichaki et al. Nature, 404:414-417, 2000.
Raymond H. Jacobson et al.: Science, 228: 1422-1425, 2000.
Tony Kouzarides: EMBO J, 19:1176-1179, 2000.
Bowser R, Giambrone A, Davies P. FACI, a novel gene identified with the monoclonal antibody Alz50, is developmentally regulated in human brain. Dev Neurosci. 1995; 17(1):20-37.
Georgakopoulos et al., "Histone acetyltransferase GCN5," EMBL Database accession No. Q03330 (1993).
Hillier et al., "zb12c07.r1 Soares_fetal_lung_NbHL19W Homo sapiens cDNA clone Image: 301826 5' similar to SW: GCN5_Yeast Q03330 Transcriptional Activator GCN5," NCBI Database accession No. W17142 (1996).
Hillier et al., "zj2lh12.s1 Soares fetal liver spleen 1NFLS s1 Homo sapiens cDNA clone 450983 3' similar to TR: Q12830 Fetal ALZ-50-Reactive Clone 1," EMBL accession No. AA704421 (1998).
Hillier et al., "zr51a03.r1 Soares NhHMPu S1 Homo sapiens cDNA clone 666892 5' similar to SW: GCN5_Yeast Q03330 Transcriptional Activator GCN5," EMBL Database accession No. AA236286 (1997).
Jones et al., "Identification and Characterization of BPTF, a Novel Bromodomain Transcription Factor," *Genomics*, 63(1):35-39 (2000).
Seq Id No: 3139 of EP 1 033 401 A2, EMBL Database accession No. AAG03135 (2000).
Seq Id No: 7216 of EP 1 033 401 A2, EMBL Database accession No. AAC03141 (2000).

*Primary Examiner*—Robert A. Wax
(74) *Attorney, Agent, or Firm*—Fish & Richardson P.C.

(57) ABSTRACT

BLAST search was done on the EST database by using various nucleotide sequences encoding known bromodomain motifs to discover several ESTs likely encoding bromodomain genes. Next, testicular cDNAs were PCR cloned by using primers designed based on the sequence of EST (W17142), which is one of the ESTs discovered above. By using the thus obtained PCR product as a probe, the testicular library was screened. The obtained cDNA clone was used as a probe to re-screen the testicular cDNA library, thereby successfully isolating a full-length cDNA corresponding to EST (W17142). The protein encoded by the thus isolated cDNA had, in addition to the bromodomain, several regions and domains conserved in transcription regulatory factors. Moreover, the protein interacted with proteins associated with the chromatin-mediated transcriptional regulatory mechanism and a transcription co-activator.

40 Claims, 8 Drawing Sheets

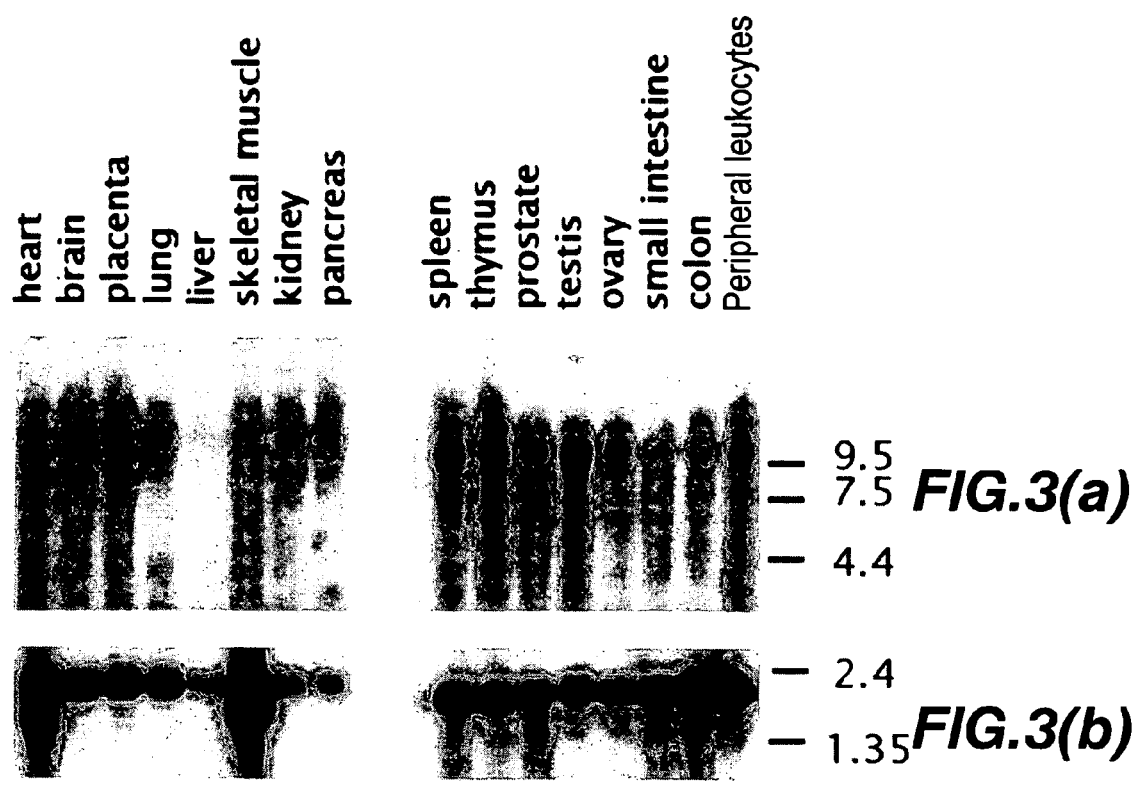

SEQUENCE LISTING

```
<160> NUMBER OF SEQ ID NOS: 10

<210> SEQ ID NO 1
<211> LENGTH: 2907
<212> TYPE: PRT
<213> ORGANISM: Homo sapiens

<400> SEQUENCE: 1

Met Val Ser Glu Glu Glu Glu Glu Asp Gly Asp Ala Glu Glu Thr
 1               5                  10                  15

Gln Asp Ser Glu Asp Asp Glu Glu Asp Glu Met Glu Glu Asp Asp Asp
                20                  25                  30

Asp Ser Asp Tyr Pro Glu Glu Met Glu Asp Asp Asp Asp Ala Ser
                35                  40                  45

Tyr Cys Thr Glu Ser Ser Phe Arg Ser His Ser Thr Tyr Ser Ser Thr
 50                  55                  60

Pro Gly Arg Arg Lys Pro Arg Val His Arg Pro Arg Ser Pro Ile Leu
 65                  70                  75                  80

Glu Glu Lys Asp Ile Pro Pro Leu Glu Phe Pro Lys Ser Ser Glu Asp
                85                  90                  95

Leu Met Val Pro Asn Glu His Ile Met Asn Val Ile Ala Ile Tyr Glu
                100                 105                 110

Val Leu Arg Asn Phe Gly Thr Val Leu Arg Leu Ser Pro Phe Arg Phe
            115                 120                 125

Glu Asp Phe Cys Ala Ala Leu Val Ser Gln Glu Gln Cys Thr Leu Met
        130                 135                 140

Ala Glu Met His Val Val Leu Leu Lys Ala Val Leu Arg Glu Glu Asp
145                 150                 155                 160

Thr Ser Asn Thr Thr Phe Gly Pro Ala Asp Leu Lys Asp Ser Val Asn
                165                 170                 175

Ser Thr Leu Tyr Phe Ile Asp Gly Met Thr Trp Pro Glu Val Leu Arg
            180                 185                 190

Val Tyr Cys Glu Ser Asp Lys Glu Tyr His His Val Leu Pro Tyr Gln
        195                 200                 205

Glu Ala Glu Asp Tyr Pro Tyr Gly Pro Val Glu Asn Lys Ile Lys Val
    210                 215                 220

Leu Gln Phe Leu Val Asp Gln Phe Leu Thr Thr Asn Ile Ala Arg Glu
225                 230                 235                 240

Glu Leu Met Ser Glu Gly Val Ile Gln Tyr Asp Asp His Cys Arg Val
                245                 250                 255

Cys His Lys Leu Gly Asp Leu Leu Cys Cys Glu Thr Cys Ser Ala Val
                260                 265                 270
```

-continued

```
Tyr His Leu Glu Cys Val Lys Pro Pro Leu Glu Glu Val Pro Glu Asp
        275                 280                 285

Glu Trp Gln Cys Glu Val Cys Val Ala His Lys Val Pro Gly Val Thr
    290                 295                 300

Asp Cys Val Ala Glu Ile Gln Lys Asn Lys Pro Tyr Ile Arg His Glu
305                 310                 315                 320

Pro Ile Gly Tyr Asp Arg Ser Arg Arg Lys Tyr Trp Phe Leu Asn Arg
                325                 330                 335

Arg Leu Ile Ile Glu Glu Asp Thr Glu Asn Glu Asn Glu Lys Lys Ile
            340                 345                 350

Trp Tyr Tyr Ser Thr Lys Val Gln Leu Ala Glu Leu Ile Asp Cys Leu
        355                 360                 365

Asp Lys Asp Tyr Trp Glu Ala Glu Leu Cys Lys Ile Leu Glu Glu Met
    370                 375                 380

Arg Glu Glu Ile His Arg His Met Asp Ile Thr Glu Asp Leu Thr Asn
385                 390                 395                 400

Lys Ala Arg Gly Ser Asn Lys Ser Phe Leu Ala Ala Ala Asn Glu Glu
                405                 410                 415

Ile Leu Glu Ser Ile Arg Ala Lys Lys Gly Asp Ile Asp Asn Val Lys
            420                 425                 430

Ser Pro Glu Glu Thr Glu Lys Asp Lys Asn Glu Thr Glu Asn Asp Ser
        435                 440                 445

Lys Asp Ala Glu Lys Asn Arg Glu Glu Phe Glu Asp Gln Ser Leu Glu
    450                 455                 460

Lys Asp Ser Asp Asp Lys Thr Pro Asp Asp Pro Glu Gln Gly Lys
465                 470                 475                 480

Ser Glu Glu Pro Thr Glu Val Gly Asp Lys Gly Asn Ser Val Ser Ala
                485                 490                 495

Asn Leu Gly Asp Asn Thr Thr Asn Ala Thr Ser Glu Glu Thr Ser Pro
            500                 505                 510

Ser Glu Gly Arg Ser Pro Val Gly Cys Leu Ser Glu Thr Pro Asp Ser
        515                 520                 525

Ser Asn Met Ala Glu Lys Lys Val Ala Ser Glu Leu Pro Gln Asp Val
    530                 535                 540

Pro Glu Glu Pro Asn Lys Thr Cys Glu Ser Ser Asn Thr Ser Ala Thr
545                 550                 555                 560

Thr Thr Ser Ile Gln Pro Asn Leu Glu Asn Ser Asn Ser Ser Ser Glu
                565                 570                 575

Leu Asn Ser Ser Gln Ser Glu Ser Ala Lys Ala Ala Asp Asp Pro Glu
            580                 585                 590

Asn Gly Glu Arg Glu Ser His Thr Pro Val Ser Ile Gln Glu Glu Ile
        595                 600                 605

Val Gly Asp Phe Thr Ser Glu Lys Ser Thr Gly Glu Leu Ser Glu Ser
    610                 615                 620

Pro Gly Ala Gly Lys Gly Ala Ser Gly Ser Thr Arg Ile Ile Thr Arg
625                 630                 635                 640

Leu Arg Asn Pro Asp Ser Lys Leu Ser Gln Leu Lys Ser Gln Gln Val
                645                 650                 655

Ala Ala Ala Ala His Glu Ala Asn Lys Leu Phe Lys Glu Gly Lys Glu
            660                 665                 670

Val Leu Val Val Asn Ser Gln Gly Glu Ile Ser Arg Leu Ser Thr Lys
        675                 680                 685
```

-continued

```
Lys Glu Val Ile Met Lys Gly Asn Ile Asn Asn Tyr Phe Lys Leu Gly
        690                 695                 700
Gln Glu Gly Lys Tyr Arg Val Tyr His Asn Gln Tyr Ser Thr Asn Ser
705                 710                 715                 720
Phe Ala Leu Asn Lys His Gln His Arg Glu Asp His Asp Lys Arg Arg
                725                 730                 735
His Leu Ala His Lys Phe Cys Leu Thr Pro Ala Gly Glu Phe Lys Trp
            740                 745                 750
Asn Gly Ser Val His Gly Ser Lys Val Leu Thr Ile Ser Thr Leu Arg
        755                 760                 765
Leu Thr Ile Thr Gln Leu Glu Asn Asn Ile Pro Ser Ser Phe Phe His
770                 775                 780
Pro Asn Trp Ala Ser His Arg Ala Asn Trp Ile Lys Ala Val Gln Met
785                 790                 795                 800
Cys Ser Lys Pro Arg Glu Phe Ala Leu Ala Leu Ala Ile Leu Glu Cys
                805                 810                 815
Ala Val Lys Pro Val Val Met Leu Pro Ile Trp Arg Glu Phe Leu Gly
            820                 825                 830
His Thr Arg Leu His Arg Met Thr Ser Ile Glu Arg Glu Glu Lys Glu
        835                 840                 845
Lys Val Lys Lys Lys Glu Lys Lys Gln Glu Glu Glu Thr Met Gln
850                 855                 860
Gln Ala Thr Trp Val Lys Tyr Thr Phe Pro Val Lys His Gln Val Trp
865                 870                 875                 880
Lys Gln Lys Gly Glu Glu Tyr Arg Val Thr Gly Tyr Gly Trp Ser
                885                 890                 895
Trp Ile Ser Lys Thr His Val Tyr Arg Phe Val Pro Lys Leu Pro Gly
            900                 905                 910
Asn Thr Asn Val Asn Tyr Arg Lys Ser Leu Glu Gly Thr Lys Asn Asn
        915                 920                 925
Met Asp Glu Asn Met Asp Glu Ser Asp Lys Arg Lys Cys Ser Arg Ser
930                 935                 940
Pro Lys Lys Ile Lys Ile Glu Pro Asp Ser Lys Asp Glu Val Lys
945                 950                 955                 960
Gly Ser Asp Ala Ala Lys Gly Ala Asp Gln Asn Glu Met Asp Ile Ser
                965                 970                 975
Lys Ile Thr Glu Lys Lys Asp Gln Asp Val Lys Glu Leu Leu Asp Ser
            980                 985                 990
Asp Ser Asp Lys Pro Cys Lys Glu Glu Pro Met Glu Val Asp Asp Asp
        995                 1000                1005
Met Lys Thr Glu Ser His Val Asn Cys Gln Glu Ser Ser Gln Val Asp
        1010                1015                1020
Val Val Asn Val Ser Glu Gly Phe His Leu Arg Thr Ser Tyr Lys Lys
1025                1030                1035                1040
Lys Thr Lys Ser Ser Lys Leu Asp Gly Leu Leu Glu Arg Arg Ile Lys
                1045                1050                1055
Gln Phe Thr Leu Glu Glu Lys Gln Arg Leu Glu Lys Ile Lys Leu Glu
            1060                1065                1070
Gly Gly Ile Lys Gly Ile Gly Lys Thr Ser Thr Asn Ser Ser Lys Asn
        1075                1080                1085
Leu Ser Glu Ser Pro Val Ile Thr Lys Ala Lys Glu Gly Cys Gln Ser
1090                1095                1100
```

```
Asp Ser Met Arg Gln Glu Gln Ser Pro Asn Ala Asn Asn Asp Gln Pro
1105                1110                1115                1120

Glu Asp Leu Ile Gln Gly Cys Ser Gln Ser Asp Ser Ser Val Leu Arg
            1125                1130                1135

Met Ser Asp Pro Ser His Thr Thr Asn Lys Leu Tyr Pro Lys Asp Arg
            1140                1145                1150

Val Leu Asp Asp Val Ser Ile Arg Ser Pro Glu Thr Lys Cys Pro Lys
            1155                1160                1165

Gln Asn Ser Ile Glu Asn Asp Ile Glu Glu Lys Val Ser Asp Leu Ala
            1170                1175                1180

Ser Arg Gly Gln Glu Pro Thr Lys Ser Lys Thr Lys Gly Asn Asp Phe
1185                1190                1195                1200

Phe Ile Asp Asp Ser Lys Leu Ala Ser Ala Asp Asp Ile Gly Thr Leu
                1205                1210                1215

Ile Cys Lys Asn Lys Lys Pro Leu Ile Gln Glu Glu Ser Asp Thr Ile
                1220                1225                1230

Val Ser Ser Ser Lys Ser Ala Leu His Ser Ser Val Pro Lys Ser Thr
                1235                1240                1245

Asn Asp Arg Asp Ala Thr Pro Leu Ser Arg Ala Met Asp Phe Glu Gly
                1250                1255                1260

Lys Leu Gly Cys Asp Ser Glu Ser Asn Ser Thr Leu Glu Asn Ser Ser
1265                1270                1275                1280

Asp Thr Val Ser Ile Gln Asp Ser Ser Glu Glu Asp Met Ile Val Gln
                1285                1290                1295

Asn Ser Asn Glu Ser Ile Ser Glu Gln Phe Arg Thr Arg Glu Gln Asp
                1300                1305                1310

Val Glu Val Leu Glu Pro Leu Lys Cys Glu Leu Val Ser Gly Glu Ser
            1315                1320                1325

Thr Gly Asn Cys Glu Asp Arg Leu Pro Val Lys Gly Thr Glu Ala Asn
            1330                1335                1340

Gly Lys Lys Pro Ser Gln Gln Lys Lys Leu Glu Glu Arg Pro Val Asn
1345                1350                1355                1360

Lys Cys Ser Asp Gln Ile Lys Leu Lys Asn Thr Thr Asp Lys Lys Asn
                1365                1370                1375

Asn Glu Asn Arg Glu Ser Glu Lys Lys Gly Gln Arg Thr Ser Thr Phe
                1380                1385                1390

Gln Ile Asn Gly Lys Asp Asn Lys Pro Lys Ile Tyr Leu Lys Gly Glu
            1395                1400                1405

Cys Leu Lys Glu Ile Ser Glu Ser Arg Val Val Ser Gly Asn Val Glu
    1410                1415                1420

Pro Lys Val Asn Asn Ile Asn Lys Ile Ile Pro Glu Asn Asp Ile Lys
1425                1430                1435                1440

Ser Leu Thr Val Lys Glu Ser Ala Ile Arg Pro Phe Ile Asn Gly Asp
                1445                1450                1455

Val Ile Met Glu Asp Phe Asn Glu Arg Asn Ser Ser Glu Thr Lys Ser
            1460                1465                1470

His Leu Leu Ser Ser Ser Asp Ala Glu Gly Asn Tyr Arg Asp Ser Leu
    1475                1480                1485

Glu Thr Leu Pro Ser Thr Lys Glu Ser Asp Ser Thr Gln Thr Thr Thr
    1490                1495                1500

Pro Ser Ala Ser Cys Pro Glu Ser Asn Ser Val Asn Gln Val Glu Asp
1505                1510                1515                1520
```

```
Met Glu Ile Glu Thr Ser Glu Val Lys Lys Val Thr Ser Pro Ile
                1525                1530                1535

Thr Ser Glu Glu Glu Ser Asn Leu Ser Asn Asp Phe Ile Asp Glu Asn
                1540                1545                1550

Gly Leu Pro Ile Asn Lys Asn Glu Asn Val Asn Gly Glu Ser Lys Arg
                1555                1560                1565

Lys Thr Val Ile Thr Glu Val Thr Thr Met Thr Ser Thr Val Ala Thr
                1570                1575                1580

Glu Ser Lys Thr Val Ile Lys Val Glu Lys Gly Asp Lys Gln Thr Val
1585                1590                1595                1600

Val Ser Ser Thr Glu Asn Cys Ala Lys Ser Thr Val Thr Thr Thr Thr
                1605                1610                1615

Thr Thr Val Thr Lys Leu Ser Thr Pro Ser Thr Gly Gly Ser Val Asp
                1620                1625                1630

Ile Ile Ser Val Lys Glu Gln Ser Lys Thr Val Val Thr Thr Thr Val
                1635                1640                1645

Thr Asp Ser Leu Thr Thr Thr Gly Gly Thr Leu Val Thr Ser Met Thr
                1650                1655                1660

Val Ser Lys Glu Tyr Ser Thr Arg Asp Lys Val Lys Leu Met Lys Phe
1665                1670                1675                1680

Ser Arg Pro Lys Lys Thr Arg Ser Gly Thr Ala Leu Pro Ser Tyr Arg
                1685                1690                1695

Lys Phe Val Thr Lys Ser Thr Lys Lys Ser Ile Phe Val Leu Pro Asn
                1700                1705                1710

Asp Asp Leu Lys Lys Leu Ala Arg Lys Gly Gly Ile Arg Glu Val Pro
                1715                1720                1725

Tyr Phe Asn Tyr Asn Ala Lys Pro Ala Leu Asp Ile Trp Pro Tyr Pro
                1730                1735                1740

Ser Pro Arg Pro Thr Phe Gly Ile Thr Trp Arg Tyr Arg Leu Gln Thr
1745                1750                1755                1760

Val Lys Ser Leu Ala Gly Val Ser Leu Met Leu Arg Leu Leu Trp Ala
                1765                1770                1775

Ser Leu Arg Trp Asp Asp Met Ala Ala Lys Val Pro Pro Gly Gly Gly
                1780                1785                1790

Ser Thr Arg Thr Glu Thr Ser Glu Thr Glu Ile Thr Thr Thr Glu Ile
                1795                1800                1805

Ile Lys Arg Arg Asp Val Gly Pro Tyr Gly Ile Arg Phe Glu Tyr Cys
                1810                1815                1820

Ile Arg Lys Ile Ile Cys Pro Ile Gly Val Pro Glu Thr Pro Lys Glu
1825                1830                1835                1840

Thr Pro Thr Pro Gln Arg Lys Gly Leu Arg Ser Ser Ala Leu Arg Pro
                1845                1850                1855

Lys Arg Pro Glu Thr Pro Lys Gln Thr Gly Pro Val Ile Ile Glu Thr
                1860                1865                1870

Trp Val Ala Glu Glu Glu Leu Glu Leu Trp Glu Ile Arg Ala Phe Ala
                1875                1880                1885

Glu Arg Val Glu Lys Glu Lys Ala Gln Ala Val Glu Gln Gln Ala Lys
                1890                1895                1900

Lys Arg Leu Glu Gln Gln Lys Pro Thr Val Ile Ala Thr Ser Thr Thr
1905                1910                1915                1920

Ser Pro Thr Ser Ser Thr Thr Ser Thr Ile Ser Pro Ala Gln Lys Val
                1925                1930                1935
```

-continued

```
Met Val Ala Pro Ile Ser Gly Ser Val Thr Thr Gly Thr Lys Met Val
            1940                1945                1950

Leu Thr Thr Lys Val Gly Ser Pro Ala Thr Val Thr Phe Gln Gln Asn
        1955                1960                1965

Lys Asn Phe His Gln Thr Phe Ala Thr Trp Val Lys Gln Gly Gln Ser
    1970                1975                1980

Asn Ser Gly Val Val Gln Val Gln Gln Lys Val Leu Gly Ile Ile Pro
1985                1990                1995                2000

Ser Ser Thr Gly Thr Ser Gln Gln Thr Phe Thr Ser Phe Gln Pro Arg
                2005                2010                2015

Thr Ala Thr Val Thr Ile Arg Pro Asn Thr Ser Gly Ser Gly Gly Thr
                2020                2025                2030

Thr Ser Asn Ser Gln Val Ile Thr Gly Pro Gln Ile Arg Pro Gly Met
            2035                2040                2045

Thr Val Ile Arg Thr Pro Leu Gln Gln Ser Thr Leu Gly Lys Ala Ile
    2050                2055                2060

Ile Arg Thr Pro Val Met Val Gln Pro Gly Ala Pro Gln Gln Val Met
2065                2070                2075                2080

Thr Gln Ile Ile Arg Gly Gln Pro Val Ser Thr Ala Val Ser Ala Pro
                2085                2090                2095

Asn Thr Val Ser Ser Thr Pro Gly Gln Lys Ser Leu Thr Ser Ala Thr
            2100                2105                2110

Ser Thr Ser Asn Ile Gln Ser Ser Ala Ser Gln Pro Pro Arg Pro Gln
            2115                2120                2125

Gln Gly Gln Val Lys Leu Thr Met Ala Gln Leu Thr Gln Leu Thr Gln
    2130                2135                2140

Gly His Gly Gly Asn Gln Gly Leu Thr Val Val Ile Gln Gly Gln Gly
2145                2150                2155                2160

Gln Thr Thr Gly Gln Leu Gln Leu Ile Pro Gln Gly Val Thr Val Leu
                2165                2170                2175

Pro Gly Pro Gly Gln Gln Leu Met Gln Ala Ala Met Pro Asn Gly Thr
                2180                2185                2190

Val Gln Arg Phe Leu Phe Thr Pro Leu Ala Thr Thr Ala Thr Thr Ala
            2195                2200                2205

Ser Thr Thr Thr Thr Thr Val Ser Thr Thr Ala Ala Gly Thr Gly Glu
    2210                2215                2220

Gln Arg Gln Ser Lys Leu Ser Pro Gln Met Gln Val His Gln Asp Lys
2225                2230                2235                2240

Thr Leu Pro Pro Ala Gln Ser Ser Val Gly Pro Ala Lys Ala Gln
                2245                2250                2255

Pro Gln Thr Ala Gln Pro Ser Ala Arg Pro Gln Pro Gln Thr Gln Pro
                2260                2265                2270

Gln Ser Pro Ala Gln Pro Glu Val Gln Thr Gln Pro Glu Val Gln Thr
            2275                2280                2285

Gln Thr Thr Val Ser Ser His Val Pro Ser Glu Ala Gln Pro Thr His
    2290                2295                2300

Ala Gln Ser Ser Lys Pro Gln Val Ala Ala Gln Ser Gln Pro Gln Ser
2305                2310                2315                2320

Asn Val Gln Gly Gln Ser Pro Val Arg Val Gln Ser Pro Ser Gln Thr
            2325                2330                2335

Arg Ile Arg Pro Ser Thr Pro Ser Gln Leu Ser Pro Gly Gln Gln Ser
            2340                2345                2350
```

```
Gln Val Gln Thr Thr Thr Ser Gln Pro Ile Pro Ile Gln Pro His Thr
            2355                2360                2365
Ser Leu Gln Ile Pro Ser Gln Gly Gln Pro Gln Ser Gln Pro Gln Val
        2370                2375                2380
Gln Ser Ser Thr Gln Thr Leu Ser Ser Gly Gln Thr Leu Asn Gln Val
2385                2390                2395                2400
Ser Val Ser Ser Pro Ser Arg Pro Gln Leu Gln Ile Gln Gln Pro Gln
            2405                2410                2415
Pro Gln Val Ile Ala Val Pro Gln Leu Gln Gln Val Gln Val Leu
        2420                2425                2430
Ser Gln Ile Gln Ser Gln Val Val Ala Gln Ile Gln Ala Gln Gln Ser
            2435                2440                2445
Gly Val Pro Gln Gln Ile Lys Leu Gln Leu Pro Ile Gln Ile Gln Gln
        2450                2455                2460
Ser Ser Ala Val Gln Thr His Gln Ile Gln Asn Val Val Thr Val Gln
2465                2470                2475                2480
Ala Ala Ser Val Gln Glu Gln Leu Gln Arg Val Gln Gln Leu Arg Asp
            2485                2490                2495
Gln Gln Gln Lys Lys Gln Gln Gln Ile Glu Ile Asn Val Asn Thr
        2500                2505                2510
Pro Ser Lys Leu Leu Ile Lys Val Glu Ile Ile Gln Lys Gln Val Val
            2515                2520                2525
Met Lys His Asn Ala Val Ile Glu His Leu Lys Gln Lys Lys Ser Met
        2530                2535                2540
Thr Pro Ala Glu Arg Glu Glu Asn Gln Arg Met Ile Val Cys Asn Gln
2545                2550                2555                2560
Val Met Lys Tyr Ile Leu Asp Lys Ile Asp Lys Glu Glu Lys Gln Ala
            2565                2570                2575
Ala Lys Lys Arg Lys Arg Glu Glu Ser Val Glu Gln Lys Arg Ser Lys
        2580                2585                2590
Gln Asn Ala Thr Lys Leu Ser Ala Leu Leu Phe Lys His Lys Glu Gln
            2595                2600                2605
Leu Arg Ala Glu Ile Leu Lys Lys Arg Ala Leu Leu Asp Lys Asp Leu
        2610                2615                2620
Gln Ile Glu Val Gln Glu Glu Leu Lys Arg Asp Leu Lys Ile Lys Lys
2625                2630                2635                2640
Glu Lys Asp Leu Met Gln Leu Ala Gln Ala Thr Ala Val Ala Ala Pro
            2645                2650                2655
Cys Pro Pro Val Thr Pro Val Leu Pro Ala Pro Pro Ala Pro Pro Pro
        2660                2665                2670
Ser Pro Pro Pro Pro Gly Val Gln His Thr Gly Leu Leu Ser Thr
            2675                2680                2685
Pro Thr Leu Pro Val Ala Ser Gln Lys Arg Lys Arg Glu Glu Lys
        2690                2695                2700
Asp Ser Ser Ser Lys Ser Lys Lys Lys Met Ile Ser Thr Thr Ser
2705                2710                2715                2720
Lys Glu Thr Lys Lys Asp Thr Lys Leu Tyr Cys Ile Cys Lys Thr Pro
            2725                2730                2735
Tyr Asp Glu Ser Lys Phe Tyr Ile Gly Cys Asp Arg Cys Gln Asn Trp
            2740                2745                2750
Tyr His Gly Arg Cys Val Gly Ile Leu Gln Ser Glu Ala Glu Leu Ile
            2755                2760                2765
```

```
Asp Glu Tyr Val Cys Pro Gln Cys Gln Ser Thr Glu Asp Ala Met Thr
    2770            2775                2780
Val Leu Thr Pro Leu Thr Glu Lys Asp Tyr Glu Gly Leu Lys Arg Val
2785            2790                2795                2800
Leu Arg Ser Leu Gln Ala His Lys Met Ala Trp Pro Phe Leu Glu Pro
            2805                2810                2815
Val Asp Pro Asn Asp Ala Pro Asp Tyr Tyr Gly Val Ile Lys Glu Pro
        2820                2825                2830
Met Asp Leu Ala Thr Met Glu Glu Arg Val Gln Arg Arg Tyr Tyr Glu
        2835                2840                2845
Lys Leu Thr Glu Phe Val Ala Asp Met Thr Lys Ile Phe Asp Asn Cys
    2850                2855                2860
Arg Tyr Tyr Asn Pro Ser Asp Ser Pro Phe Tyr Gln Cys Ala Glu Val
2865            2870                2875                2880
Leu Glu Ser Phe Phe Val Gln Lys Leu Lys Gly Phe Lys Ala Ser Arg
            2885                2890                2895
Ser His Asn Asn Lys Leu Gln Ser Thr Ala Ser
            2900                2905

<210> SEQ ID NO 2
<211> LENGTH: 9865
<212> TYPE: DNA
<213> ORGANISM: Homo sapiens
<220> FEATURE:
<221> NAME/KEY: CDS
<222> LOCATION: (259)...(8979)

<400> SEQUENCE: 2
ggccaggctg aggtggcgcc caagacgcgg ctgagctcgc ccaggggggg cagcagtagc      60
cggaggaagc cgccgccgcc gccgccggcc ccccccagca ccagcgcccc gggccggggg     120
gggcgaggag gcggggcgg cacgacgggg ggcgggggcg gcggcggcca cctgtcccgg     180
accaccgcgg cccggagggc cgtcaacaaa gtggtgtacg atgaccacga gagcgaggcg     240
gtggaggaag aggaggac atg gtc tcc gag gag gag gag gag gag gac ggc       291
                   Met Val Ser Glu Glu Glu Glu Glu Glu Asp Gly
                     1               5                  10 gac gcc gag gag acc cag gat tct gag gac gac gag gag gat gag atg       339
Asp Ala Glu Glu Thr Gln Asp Ser Glu Asp Asp Glu Glu Asp Glu Met
            15                  20                  25 gaa gag gac gac gat gac tcc gat tat ccg gag gag atg gaa gac gac       387
Glu Glu Asp Asp Asp Asp Ser Asp Tyr Pro Glu Glu Met Glu Asp Asp
        30                  35                  40 gac gac gac gcc agt tac tgc acg gaa agc agc ttc agg agc cat agt       435
Asp Asp Asp Ala Ser Tyr Cys Thr Glu Ser Ser Phe Arg Ser His Ser
    45                  50                  55 acc tac agc agc act cca ggt agg cga aaa cca aga gta cat cgg cct       483
Thr Tyr Ser Ser Thr Pro Gly Arg Arg Lys Pro Arg Val His Arg Pro
60                  65                  70                  75 cgt tct cct ata ttg gaa gaa aaa gac atc ccg ccc ctt gaa ttt ccc       531
Arg Ser Pro Ile Leu Glu Glu Lys Asp Ile Pro Pro Leu Glu Phe Pro
                80                  85                  90 aag tcc tct gag gat tta atg gtg cct aat gag cat ata atg aat gtc       579
Lys Ser Ser Glu Asp Leu Met Val Pro Asn Glu His Ile Met Asn Val
            95                 100                 105 att gcc att tac gag gta ctg cgg aac ttt ggc act gtt ttg aga tta       627
Ile Ala Ile Tyr Glu Val Leu Arg Asn Phe Gly Thr Val Leu Arg Leu
        110                 115                 120 tct cct ttt cgc ttt gag gac ttt tgt gca gct ctg gtg agc caa gag       675
```

```
                                                       -continued

Ser Pro Phe Arg Phe Glu Asp Phe Cys Ala Ala Leu Val Ser Gln Glu
    125                 130                 135 cag tgc aca ctc atg gca gag atg cat gtt gtg ctt ttg aaa gca gtt      723
Gln Cys Thr Leu Met Ala Glu Met His Val Val Leu Leu Lys Ala Val
140                 145                 150                 155 ctg cgt gaa gaa gac act tcc aat act acc ttt gga cct gct gat ctg      771
Leu Arg Glu Glu Asp Thr Ser Asn Thr Thr Phe Gly Pro Ala Asp Leu
                160                 165                 170 aaa gat agc gtt aat tcc aca ctg tat ttc ata gat ggg atg acg tgg      819
Lys Asp Ser Val Asn Ser Thr Leu Tyr Phe Ile Asp Gly Met Thr Trp
            175                 180                 185 cca gag gtg ctg cgg gtg tac tgt gag agt gat aag gag tac cat cac      867
Pro Glu Val Leu Arg Val Tyr Cys Glu Ser Asp Lys Glu Tyr His His
        190                 195                 200 gtt ctt cct tac caa gag gca gag gac tac cca tat gga cca gta gag      915
Val Leu Pro Tyr Gln Glu Ala Glu Asp Tyr Pro Tyr Gly Pro Val Glu
    205                 210                 215 aac aag atc aaa gtt cta cag ttt cta gtc gat cag ttt ctt aca aca      963
Asn Lys Ile Lys Val Leu Gln Phe Leu Val Asp Gln Phe Leu Thr Thr
220                 225                 230                 235 aat att gct cga gag gaa ttg atg tct gaa ggg gtg ata cag tat gat     1011
Asn Ile Ala Arg Glu Glu Leu Met Ser Glu Gly Val Ile Gln Tyr Asp
                240                 245                 250 gac cat tgt agg gtt tgt cac aaa ctt ggg gat ttg ctt tgc tgt gag     1059
Asp His Cys Arg Val Cys His Lys Leu Gly Asp Leu Leu Cys Cys Glu
            255                 260                 265 aca tgt tca gca gta tac cat ttg gaa tgt gtg aag cca cct ctt gag     1107
Thr Cys Ser Ala Val Tyr His Leu Glu Cys Val Lys Pro Pro Leu Glu
        270                 275                 280 gag gtg cca gag gac gag tgg cag tgt gaa gtc tgt gta gca cac aag     1155
Glu Val Pro Glu Asp Glu Trp Gln Cys Glu Val Cys Val Ala His Lys
    285                 290                 295 gtg cct ggt gtg act gac tgt gtt gct gaa atc caa aaa aat aaa cca     1203
Val Pro Gly Val Thr Asp Cys Val Ala Glu Ile Gln Lys Asn Lys Pro
300                 305                 310                 315 tat att cga cat gaa cct att gga tat gat aga agt cgg agg aaa tac     1251
Tyr Ile Arg His Glu Pro Ile Gly Tyr Asp Arg Ser Arg Arg Lys Tyr
                320                 325                 330 tgg ttc ttg aac cga aga ctc ata ata gaa gaa gat aca gaa aat gaa     1299
Trp Phe Leu Asn Arg Arg Leu Ile Ile Glu Glu Asp Thr Glu Asn Glu
            335                 340                 345 aat gaa aag aaa att tgg tat tac agc aca aag gtc caa ctt gca gaa     1347
Asn Glu Lys Lys Ile Trp Tyr Tyr Ser Thr Lys Val Gln Leu Ala Glu
        350                 355                 360 tta att gac tgt cta gac aaa gat tat tgg gaa gca gaa ctc tgc aaa     1395
Leu Ile Asp Cys Leu Asp Lys Asp Tyr Trp Glu Ala Glu Leu Cys Lys
    365                 370                 375 att cta gaa gaa atg cgt gaa gaa atc cac cga cac atg gac ata act     1443
Ile Leu Glu Glu Met Arg Glu Glu Ile His Arg His Met Asp Ile Thr
380                 385                 390                 395 gaa gac ctg acc aat aag gct cgg ggc agt aac aaa tcc ttt ctg gcg     1491
Glu Asp Leu Thr Asn Lys Ala Arg Gly Ser Asn Lys Ser Phe Leu Ala
                400                 405                 410 gca gct aat gaa gaa att ttg gaa tcc ata aga gcc aaa aag gga gac     1539
Ala Ala Asn Glu Glu Ile Leu Glu Ser Ile Arg Ala Lys Lys Gly Asp
            415                 420                 425 att gat aat gtt aaa agc cca gaa gaa aca gaa aaa gac aag aat gag     1587
Ile Asp Asn Val Lys Ser Pro Glu Glu Thr Glu Lys Asp Lys Asn Glu
        430                 435                 440
```

```
act gag aat gac tct aaa gat gct gag aaa aac aga gaa gaa ttt gaa    1635
Thr Glu Asn Asp Ser Lys Asp Ala Glu Lys Asn Arg Glu Glu Phe Glu
        445                 450                 455 gac cag tcc ctt gaa aaa gac agt gac gac aaa aca cca gat gat gac    1683
Asp Gln Ser Leu Glu Lys Asp Ser Asp Asp Lys Thr Pro Asp Asp Asp
460                 465                 470                 475 cct gag caa gga aaa tct gag gag cca aca gaa gtt ggg gat aaa ggt    1731
Pro Glu Gln Gly Lys Ser Glu Glu Pro Thr Glu Val Gly Asp Lys Gly
                480                 485                 490 aac tct gtg tca gca aat ctt ggc gac aac aca aca aat gca act tca    1779
Asn Ser Val Ser Ala Asn Leu Gly Asp Asn Thr Thr Asn Ala Thr Ser
            495                 500                 505 gaa gag act agt ccc tct gaa ggg agg agc cct gtg ggg tgt ctc tca    1827
Glu Glu Thr Ser Pro Ser Glu Gly Arg Ser Pro Val Gly Cys Leu Ser
        510                 515                 520 gaa acc ccc gat agc agc aac atg gca gag aag aag gtg gca tct gag    1875
Glu Thr Pro Asp Ser Ser Asn Met Ala Glu Lys Lys Val Ala Ser Glu
525                 530                 535 ctc ccc cag gat gtg cca gaa gaa cct aac aag aca tgt gag agc agt    1923
Leu Pro Gln Asp Val Pro Glu Glu Pro Asn Lys Thr Cys Glu Ser Ser
540                 545                 550                 555 aac act agt gct acc act acc tcc atc cag cct aat ctg gaa aac agt    1971
Asn Thr Ser Ala Thr Thr Thr Ser Ile Gln Pro Asn Leu Glu Asn Ser
                560                 565                 570 aac agc agc agt gaa cta aat tct tcc cag agt gaa tct gct aag gca    2019
Asn Ser Ser Ser Glu Leu Asn Ser Ser Gln Ser Glu Ser Ala Lys Ala
            575                 580                 585 gct gat gat cct gaa aat gga gaa aga gaa tct cat aca cct gtc tct    2067
Ala Asp Asp Pro Glu Asn Gly Glu Arg Glu Ser His Thr Pro Val Ser
        590                 595                 600 att cag gaa gag ata gta ggt gat ttc aca tcg gag aag tcc acc ggg    2115
Ile Gln Glu Glu Ile Val Gly Asp Phe Thr Ser Glu Lys Ser Thr Gly
605                 610                 615 gag cta agt gaa tct cct gga gct gga aaa gga gca tct ggc tca act    2163
Glu Leu Ser Glu Ser Pro Gly Ala Gly Lys Gly Ala Ser Gly Ser Thr
620                 625                 630                 635 cga atc atc acc aga ttg cgg aat cca gat agc aaa ctt agt cag ctg    2211
Arg Ile Ile Thr Arg Leu Arg Asn Pro Asp Ser Lys Leu Ser Gln Leu
                640                 645                 650 aag agc cag cag gtg gca gcc gct gca cat gaa gca aat aaa tta ttt    2259
Lys Ser Gln Gln Val Ala Ala Ala Ala His Glu Ala Asn Lys Leu Phe
            655                 660                 665 aag gag ggc aaa gag gta ctg gta gtt aac tct caa gga gaa att tca    2307
Lys Glu Gly Lys Glu Val Leu Val Val Asn Ser Gln Gly Glu Ile Ser
        670                 675                 680 cgg ttg agc acc aaa aag gaa gtg atc atg aaa gga aat atc aac aat    2355
Arg Leu Ser Thr Lys Lys Glu Val Ile Met Lys Gly Asn Ile Asn Asn
685                 690                 695 tat ttt aaa ttg ggt caa gaa ggg aag tat cgc gtc tac cac aat caa    2403
Tyr Phe Lys Leu Gly Gln Glu Gly Lys Tyr Arg Val Tyr His Asn Gln
700                 705                 710                 715 tac tcc acc aat tca ttt gct ttg aat aag cac cag cac aga gaa gac    2451
Tyr Ser Thr Asn Ser Phe Ala Leu Asn Lys His Gln His Arg Glu Asp
                720                 725                 730 cat gat aag aga agg cat ctt gca cat aag ttc tgt ctg act cca gca    2499
His Asp Lys Arg Arg His Leu Ala His Lys Phe Cys Leu Thr Pro Ala
            735                 740                 745 gga gag ttc aaa tgg aac ggt tct gtc cat ggg tcc aaa gtt ctt acc    2547
Gly Glu Phe Lys Trp Asn Gly Ser Val His Gly Ser Lys Val Leu Thr
        750                 755                 760
```

-continued

| | |
|---|---|
| ata tct act ctg aga ctg act atc acc caa tta gaa aac aac atc cct<br>Ile Ser Thr Leu Arg Leu Thr Ile Thr Gln Leu Glu Asn Asn Ile Pro<br>765                        770                         775 | 2595 |
| tca tcc ttt ttt cat ccc aac tgg gca tca cat agg gca aat tgg atc<br>Ser Ser Phe Phe His Pro Asn Trp Ala Ser His Arg Ala Asn Trp Ile<br>780                        785                        790                        795 | 2643 |
| aag gca gtt cag atg tgt agc aaa ccc aga gaa ttt gca ttg gct tta<br>Lys Ala Val Gln Met Cys Ser Lys Pro Arg Glu Phe Ala Leu Ala Leu<br>                        800                        805                        810 | 2691 |
| gcc att ttg gag tgt gca gtt aaa cca gtt gtg atg cta cca ata tgg<br>Ala Ile Leu Glu Cys Ala Val Lys Pro Val Val Met Leu Pro Ile Trp<br>             815                        820                        825 | 2739 |
| cga gaa ttt tta gga cat acc agg tta cac cgg atg aca tca att gaa<br>Arg Glu Phe Leu Gly His Thr Arg Leu His Arg Met Thr Ser Ile Glu<br>                        830                        835                        840 | 2787 |
| aga gaa gaa aag gag aaa gtc aaa aaa aaa gag aag aaa cag gaa gaa<br>Arg Glu Glu Lys Glu Lys Val Lys Lys Lys Glu Lys Lys Gln Glu Glu<br>845                        850                         855 | 2835 |
| gaa gaa acg atg cag caa gcg aca tgg gta aaa tac aca ttt cca gtt<br>Glu Glu Thr Met Gln Gln Ala Thr Trp Val Lys Tyr Thr Phe Pro Val<br>860                        865                        870                        875 | 2883 |
| aag cat cag gtt tgg aaa caa aaa ggt gaa gag tac aga gtg aca gga<br>Lys His Gln Val Trp Lys Gln Lys Gly Glu Glu Tyr Arg Val Thr Gly<br>                        880                        885                        890 | 2931 |
| tat ggt ggt tgg agc tgg att agt aaa act cat gtt tat agg ttt gtt<br>Tyr Gly Gly Trp Ser Trp Ile Ser Lys Thr His Val Tyr Arg Phe Val<br>                        895                        900                        905 | 2979 |
| cct aaa ttg cca ggc aat act aat gtg aat tac aga aag tcg tta gaa<br>Pro Lys Leu Pro Gly Asn Thr Asn Val Asn Tyr Arg Lys Ser Leu Glu<br>                        910                        915                        920 | 3027 |
| gga acc aaa aat aat atg gat gaa aat atg gat gag tca gat aaa aga<br>Gly Thr Lys Asn Asn Met Asp Glu Asn Met Asp Glu Ser Asp Lys Arg<br>925                        930                        935 | 3075 |
| aaa tgt tca cga agt cca aaa aaa ata aaa ata gag cct gat tct gaa<br>Lys Cys Ser Arg Ser Pro Lys Lys Ile Lys Ile Glu Pro Asp Ser Glu<br>940                        945                        950                        955 | 3123 |
| aaa gat gag gta aaa ggt tca gat gct gca aaa gga gca gac caa aat<br>Lys Asp Glu Val Lys Gly Ser Asp Ala Ala Lys Gly Ala Asp Gln Asn<br>                        960                        965                        970 | 3171 |
| gaa atg gat atc tca aag att act gag aag aag gac caa gat gtg aag<br>Glu Met Asp Ile Ser Lys Ile Thr Glu Lys Lys Asp Gln Asp Val Lys<br>                        975                        980                        985 | 3219 |
| gag ctc tta gat tct gac agt gat aaa ccc tgc aag gaa gaa cca atg<br>Glu Leu Leu Asp Ser Asp Ser Asp Lys Pro Cys Lys Glu Glu Pro Met<br>                        990                        995                        1000 | 3267 |
| gaa gta gac gat gac atg aaa aca gag tca cat gta aat tgt cag gag<br>Glu Val Asp Asp Asp Met Lys Thr Glu Ser His Val Asn Cys Gln Glu<br>                        1005                      1010                      1015 | 3315 |
| agt tct caa gta gat gtg gtc aat gtt agt gag ggt ttt cat cta agg<br>Ser Ser Gln Val Asp Val Val Asn Val Ser Glu Gly Phe His Leu Arg<br>1020                        1025                      1030                      1035 | 3363 |
| act agt tac aaa aag aaa aca aaa tca tcc aaa cta gat gga ctt ctt<br>Thr Ser Tyr Lys Lys Lys Thr Lys Ser Ser Lys Leu Asp Gly Leu Leu<br>                        1040                      1045                      1050 | 3411 |
| gaa agg aga att aaa cag ttt aca ctg gaa gaa aaa cag cga ctc gaa<br>Glu Arg Arg Ile Lys Gln Phe Thr Leu Glu Glu Lys Gln Arg Leu Glu<br>1055                      1060                      1065 | 3459 |

-continued

| | |
|---|---|
| aaa atc aag ttg gag ggt gga att aag ggt ata gga aag act tct aca<br>Lys Ile Lys Leu Glu Gly Gly Ile Lys Gly Ile Gly Lys Thr Ser Thr<br>1070                  1075                1080 | 3507 |
| aat tct tca aaa aat ctc tct gaa tca cca gta ata acg aaa gca aaa<br>Asn Ser Ser Lys Asn Leu Ser Glu Ser Pro Val Ile Thr Lys Ala Lys<br>    1085                1090                1095 | 3555 |
| gaa ggg tgt cag agt gac tcg atg aga caa gaa cag agc cca aat gca<br>Glu Gly Cys Gln Ser Asp Ser Met Arg Gln Glu Gln Ser Pro Asn Ala<br>1100                  1105              1110              1115 | 3603 |
| aat aat gat caa cct gag gac ttg att cag gga tgt tca caa agt gat<br>Asn Asn Asp Gln Pro Glu Asp Leu Ile Gln Gly Cys Ser Gln Ser Asp<br>           1120                1125              1130 | 3651 |
| tcc tca gtt ctt aga atg agt gat cct agt cat acc aca aac aaa ctt<br>Ser Ser Val Leu Arg Met Ser Asp Pro Ser His Thr Thr Asn Lys Leu<br>1135                  1140              1145 | 3699 |
| tat cca aaa gat cga gtg tta gat gat gtc tcc att cgg agc cca gaa<br>Tyr Pro Lys Asp Arg Val Leu Asp Asp Val Ser Ile Arg Ser Pro Glu<br>    1150                1155                1160 | 3747 |
| aca aaa tgt ccg aaa caa aat tcc att gaa aat gac ata gaa gaa aaa<br>Thr Lys Cys Pro Lys Gln Asn Ser Ile Glu Asn Asp Ile Glu Glu Lys<br>1165                  1170              1175 | 3795 |
| gtc tct gac ctt gcc agt aga ggc cag gaa ccc act aag agt aaa acc<br>Val Ser Asp Leu Ala Ser Arg Gly Gln Glu Pro Thr Lys Ser Lys Thr<br>1180                  1185              1190              1195 | 3843 |
| aaa gga aat gat ttt ttc atc gat gac tct aaa cta gcc agt gca gat<br>Lys Gly Asn Asp Phe Phe Ile Asp Asp Ser Lys Leu Ala Ser Ala Asp<br>           1200                1205              1210 | 3891 |
| gat att ggt act ttg atc tgt aag aac aaa aaa ccg ctc ata cag gag<br>Asp Ile Gly Thr Leu Ile Cys Lys Asn Lys Lys Pro Leu Ile Gln Glu<br>                1215              1220              1225 | 3939 |
| gaa agt gac acc att gtt tct tct tcc aag agt gct tta cat tca tca<br>Glu Ser Asp Thr Ile Val Ser Ser Ser Lys Ser Ala Leu His Ser Ser<br>           1230                1235              1240 | 3987 |
| gtg cct aaa agt acc aat gac aga gat gcc aca cct ctg tca aga gca<br>Val Pro Lys Ser Thr Asn Asp Arg Asp Ala Thr Pro Leu Ser Arg Ala<br>1245                  1250              1255 | 4035 |
| atg gac ttt gaa gga aaa ctg gga tgt gac tct gaa tct aat agc act<br>Met Asp Phe Glu Gly Lys Leu Gly Cys Asp Ser Glu Ser Asn Ser Thr<br>1260                  1265              1270              1275 | 4083 |
| ttg gaa aat agt tct gat acc gtg tct att cag gat agc agt gaa gaa<br>Leu Glu Asn Ser Ser Asp Thr Val Ser Ile Gln Asp Ser Ser Glu Glu<br>           1280                1285              1290 | 4131 |
| gat atg att gtt cag aat agc aat gaa agc att tct gaa cag ttc aga<br>Asp Met Ile Val Gln Asn Ser Asn Glu Ser Ile Ser Glu Gln Phe Arg<br>                1295              1300              1305 | 4179 |
| act cga gaa caa gat gtt gaa gtc ttg gag ccg tta aag tgt gag ttg<br>Thr Arg Glu Gln Asp Val Glu Val Leu Glu Pro Leu Lys Cys Glu Leu<br>           1310                1315              1320 | 4227 |
| gtt tct ggt gag tcc act gga aac tgt gag gac agg ctg ccg gtc aag<br>Val Ser Gly Glu Ser Thr Gly Asn Cys Glu Asp Arg Leu Pro Val Lys<br>1325                  1330              1335 | 4275 |
| ggg act gaa gca aat ggt aaa aaa cca agt cag cag aag aaa tta gag<br>Gly Thr Glu Ala Asn Gly Lys Lys Pro Ser Gln Gln Lys Lys Leu Glu<br>1340                  1345              1350              1355 | 4323 |
| gag aga cca gtt aat aaa tgt agt gat caa ata aag cta aaa aat acc<br>Glu Arg Pro Val Asn Lys Cys Ser Asp Gln Ile Lys Leu Lys Asn Thr<br>                1360              1365              1370 | 4371 |

```
act gac aaa aag aat aat gaa aat cga gag tct gaa aag aaa gga cag      4419
Thr Asp Lys Lys Asn Asn Glu Asn Arg Glu Ser Glu Lys Lys Gly Gln
            1375                1380                1385 aga aca agt aca ttt caa ata aat gga aaa gat aat aaa ccc aaa ata      4467
Arg Thr Ser Thr Phe Gln Ile Asn Gly Lys Asp Asn Lys Pro Lys Ile
        1390                1395                1400 tat ttg aaa ggt gaa tgc ttg aaa gaa att tct gag agt aga gta gta      4515
Tyr Leu Lys Gly Glu Cys Leu Lys Glu Ile Ser Glu Ser Arg Val Val
    1405                1410                1415 agt ggt aat gtt gaa cca aag gtt aat aat ata aat aaa ata atc cct      4563
Ser Gly Asn Val Glu Pro Lys Val Asn Asn Ile Asn Lys Ile Ile Pro
1420                1425                1430                1435 gag aat gat att aaa tca ttg act gtt aaa gaa tct gct ata agg cca      4611
Glu Asn Asp Ile Lys Ser Leu Thr Val Lys Glu Ser Ala Ile Arg Pro
                1440                1445                1450 ttc att aat ggt gat gtc atc atg gaa gat ttt aat gaa aga aac agc      4659
Phe Ile Asn Gly Asp Val Ile Met Glu Asp Phe Asn Glu Arg Asn Ser
            1455                1460                1465 tcc gaa aca aaa tcg cat ttg ctg agt tct tca gat gct gaa ggt aac      4707
Ser Glu Thr Lys Ser His Leu Leu Ser Ser Ser Asp Ala Glu Gly Asn
        1470                1475                1480 tac cga gat agc ctt gag acc ctg cca tca acc aaa gag tct gac agt      4755
Tyr Arg Asp Ser Leu Glu Thr Leu Pro Ser Thr Lys Glu Ser Asp Ser
    1485                1490                1495 aca cag acg acc aca ccc tca gca tct tgt cca gaa agc aat tca gtt      4803
Thr Gln Thr Thr Thr Pro Ser Ala Ser Cys Pro Glu Ser Asn Ser Val
1500                1505                1510                1515 aat cag gta gaa gat atg gaa ata gaa acc tca gaa gtt aag aaa gtt      4851
Asn Gln Val Glu Asp Met Glu Ile Glu Thr Ser Glu Val Lys Lys Val
                1520                1525                1530 act tca tca cct att act tct gaa gag gaa tct aat ctc agt aat gac      4899
Thr Ser Ser Pro Ile Thr Ser Glu Glu Glu Ser Asn Leu Ser Asn Asp
            1535                1540                1545 ttt att gat gaa aat ggt ctg ccc atc aac aaa aat gaa aat gtc aat      4947
Phe Ile Asp Glu Asn Gly Leu Pro Ile Asn Lys Asn Glu Asn Val Asn
        1550                1555                1560 gga gaa tct aaa aga aaa acc gtc atc aca gaa gtc acc acg atg acc      4995
Gly Glu Ser Lys Arg Lys Thr Val Ile Thr Glu Val Thr Thr Met Thr
    1565                1570                1575 tcc aca gtg gcc aca gaa tca aaa act gtg atc aag gta gaa aaa ggc      5043
Ser Thr Val Ala Thr Glu Ser Lys Thr Val Ile Lys Val Glu Lys Gly
1580                1585                1590                1595 gat aag caa act gtg gtt tct tcc aca gaa aat tgt gca aaa tcc act      5091
Asp Lys Gln Thr Val Val Ser Ser Thr Glu Asn Cys Ala Lys Ser Thr
                1600                1605                1610 gtc aca acc acc act aca aca gtg acc aag ctt tcc aca ccc tcc aca      5139
Val Thr Thr Thr Thr Thr Thr Val Thr Lys Leu Ser Thr Pro Ser Thr
            1615                1620                1625 ggc ggc agt gtg gac atc atc tct gta aag gag cag agc aaa acc gtg      5187
Gly Gly Ser Val Asp Ile Ile Ser Val Lys Glu Gln Ser Lys Thr Val
        1630                1635                1640 gtc acc acg aca gtg aca gac tcc ctg acc acc acg gga ggc aca ctg      5235
Val Thr Thr Thr Val Thr Asp Ser Leu Thr Thr Thr Gly Gly Thr Leu
    1645                1650                1655 gtt aca tct atg act gtg agc aaa gag tat tcc aca cga gac aaa gtg      5283
Val Thr Ser Met Thr Val Ser Lys Glu Tyr Ser Thr Arg Asp Lys Val
1660                1665                1670                1675
```

```
                                                      -continued aaa ctg atg aaa ttt tca aga cca aag aag act cgt tca ggt aca gct       5331
Lys Leu Met Lys Phe Ser Arg Pro Lys Lys Thr Arg Ser Gly Thr Ala
            1680                1685                1690 ctg cca tcc tat aga aaa ttt gtt acc aag agc acc aag aag agc att       5379
Leu Pro Ser Tyr Arg Lys Phe Val Thr Lys Ser Thr Lys Lys Ser Ile
        1695                1700                1705 ttt gtt ttg cct aat gat gac tta aaa aag ttg gcc cga aaa gga gga       5427
Phe Val Leu Pro Asn Asp Asp Leu Lys Lys Leu Ala Arg Lys Gly Gly
        1710                1715                1720 atc cga gag gtc cct tat ttt aat tac aat gca aaa cct gct ttg gat       5475
Ile Arg Glu Val Pro Tyr Phe Asn Tyr Asn Ala Lys Pro Ala Leu Asp
        1725                1730                1735 ata tgg cca tat cct tct cct aga ccg acc ttt ggc atc act tgg agg       5523
Ile Trp Pro Tyr Pro Ser Pro Arg Pro Thr Phe Gly Ile Thr Trp Arg
1740                1745                1750                1755 tat aga ctt cag aca gta aag tcc tta gct gga gtg agc ctg atg tta       5571
Tyr Arg Leu Gln Thr Val Lys Ser Leu Ala Gly Val Ser Leu Met Leu
                1760                1765                1770 cgg tta ctg tgg gca agt ttg aga tgg gat gat atg gcg gcc aag gtt       5619
Arg Leu Leu Trp Ala Ser Leu Arg Trp Asp Asp Met Ala Ala Lys Val
        1775                1780                1785 cct cca gga gga ggg agt aca cgg aca gaa aca tcc gaa act gaa atc       5667
Pro Pro Gly Gly Gly Ser Thr Arg Thr Glu Thr Ser Glu Thr Glu Ile
        1790                1795                1800 aca aca aca gaa ata att aag agg aga gat gtt ggt cct tat ggc att       5715
Thr Thr Thr Glu Ile Ile Lys Arg Arg Asp Val Gly Pro Tyr Gly Ile
        1805                1810                1815 cga ttt gaa tat tgt atc agg aaa atc att tgt ccc att gga gtt cca       5763
Arg Phe Glu Tyr Cys Ile Arg Lys Ile Ile Cys Pro Ile Gly Val Pro
1820                1825                1830                1835 gaa aca cca aaa gaa acg cct aca cct cag agg aaa ggc ctt cga tca       5811
Glu Thr Pro Lys Glu Thr Pro Thr Pro Gln Arg Lys Gly Leu Arg Ser
                1840                1845                1850 agt gca ctg cgg cca aag aga cca gaa acg ccc aag caa act ggc cct       5859
Ser Ala Leu Arg Pro Lys Arg Pro Glu Thr Pro Lys Gln Thr Gly Pro
        1855                1860                1865 gtt att att gaa acc tgg gta gca gaa gaa gaa ctg gaa ttg tgg gag       5907
Val Ile Ile Glu Thr Trp Val Ala Glu Glu Glu Leu Glu Leu Trp Glu
        1870                1875                1880 atc agg gca ttt gct gag aga gtg gag aaa gaa aag gca caa gca gtt       5955
Ile Arg Ala Phe Ala Glu Arg Val Glu Lys Glu Lys Ala Gln Ala Val
        1885                1890                1895 gag caa cag gct aag aaa cga ctg gag cag cag aag ccg aca gtg att       6003
Glu Gln Gln Ala Lys Lys Arg Leu Glu Gln Gln Lys Pro Thr Val Ile
1900                1905                1910                1915 gca act tcc act act tcc cca aca agc agt aca acc agc acc atc tct       6051
Ala Thr Ser Thr Thr Ser Pro Thr Ser Ser Thr Thr Ser Thr Ile Ser
                1920                1925                1930 cca gca cag aaa gtt atg gtg gcc ccc ata agt ggc tca gtt aca act       6099
Pro Ala Gln Lys Val Met Val Ala Pro Ile Ser Gly Ser Val Thr Thr
        1935                1940                1945 gga acc aaa atg gta cta act act aaa gtt gga tct cca gct aca gta       6147
Gly Thr Lys Met Val Leu Thr Thr Lys Val Gly Ser Pro Ala Thr Val
        1950                1955                1960 aca ttc caa caa aac aag aac ttt cat caa acc ttt gct aca tgg gtt       6195
Thr Phe Gln Gln Asn Lys Asn Phe His Gln Thr Phe Ala Thr Trp Val
        1965                1970                1975
```

-continued

```
aag caa ggc cag tca aat tca ggc gtt gtt caa gta cag cag aaa gtc    6243
Lys Gln Gly Gln Ser Asn Ser Gly Val Val Gln Val Gln Gln Lys Val
1980            1985                1990                1995 ctg ggt atc att cca tca agt aca ggt acc agt cag caa acc ttt act    6291
Leu Gly Ile Ile Pro Ser Ser Thr Gly Thr Ser Gln Gln Thr Phe Thr
                2000                2005                2010 tca ttc cag ccc agg aca gca aca gtc aca att agg ccc aat acc tca    6339
Ser Phe Gln Pro Arg Thr Ala Thr Val Thr Ile Arg Pro Asn Thr Ser
            2015                2020                2025 ggc tct gga gga acc aca agc aat tca caa gta atc aca ggg cct cag    6387
Gly Ser Gly Gly Thr Thr Ser Asn Ser Gln Val Ile Thr Gly Pro Gln
        2030                2035                2040 att cgc cct ggt atg acc gtg att aga aca cca ctc caa cag tca aca    6435
Ile Arg Pro Gly Met Thr Val Ile Arg Thr Pro Leu Gln Gln Ser Thr
    2045                2050                2055 cta gga aag gca att att cga aca cct gtg atg gta cag cca ggt gct    6483
Leu Gly Lys Ala Ile Ile Arg Thr Pro Val Met Val Gln Pro Gly Ala
2060                2065                2070                2075 cct cag caa gtg atg act caa atc atc agg ggg cag cct gtc tcc act    6531
Pro Gln Gln Val Met Thr Gln Ile Ile Arg Gly Gln Pro Val Ser Thr
                2080                2085                2090 gca gtc tcc gcc cct aac acg gtt tcc tca aca cct ggg cag aaa agc    6579
Ala Val Ser Ala Pro Asn Thr Val Ser Ser Thr Pro Gly Gln Lys Ser
            2095                2100                2105 tta act tca gca acg tcc act tca aat ata cag tct tca gcc tca caa    6627
Leu Thr Ser Ala Thr Ser Thr Ser Asn Ile Gln Ser Ser Ala Ser Gln
        2110                2115                2120 ccc cct cgc ccc caa caa gga caa gtg aag ctc acc atg gct caa ctt    6675
Pro Pro Arg Pro Gln Gln Gly Gln Val Lys Leu Thr Met Ala Gln Leu
    2125                2130                2135 act cag tta aca cag ggc cac ggt ggc aat caa ggt ttg aca gta gta    6723
Thr Gln Leu Thr Gln Gly His Gly Gly Asn Gln Gly Leu Thr Val Val
2140                2145                2150                2155 att caa gga caa ggt caa act act gga cag ttg cag ttg ata cct caa    6771
Ile Gln Gly Gln Gly Gln Thr Thr Gly Gln Leu Gln Leu Ile Pro Gln
                2160                2165                2170 ggg gtg act gta ctc cca ggc cca ggc cag cag cta atg caa gct gca    6819
Gly Val Thr Val Leu Pro Gly Pro Gly Gln Gln Leu Met Gln Ala Ala
            2175                2180                2185 atg cca aat ggt act gtt cag cga ttc ctc ttt acc cca ttg gca aca    6867
Met Pro Asn Gly Thr Val Gln Arg Phe Leu Phe Thr Pro Leu Ala Thr
        2190                2195                2200 aca gcc acc aca gcc agc acc acc acc act gtt tcc acg aca gca        6915
Thr Ala Thr Thr Ala Ser Thr Thr Thr Thr Val Ser Thr Thr Ala
    2205                2210                2215 gca ggt aca ggt gaa caa agg cag agt aaa ctg tca ccc cag atg cag    6963
Ala Gly Thr Gly Glu Gln Arg Gln Ser Lys Leu Ser Pro Gln Met Gln
2220                2225                2230                2235 gta cat caa gac aaa acc ctg cca cca gct cag tca tca agt gtg ggt    7011
Val His Gln Asp Lys Thr Leu Pro Pro Ala Gln Ser Ser Ser Val Gly
                2240                2245                2250 cca gca aaa gcc cag cca cag act gct cag cct tca gct cgg ccc cag    7059
Pro Ala Lys Ala Gln Pro Gln Thr Ala Gln Pro Ser Ala Arg Pro Gln
            2255                2260                2265 ccc caa acc cag ccc cag tcc cca gct cag cct gaa gtt cag act cag    7107
Pro Gln Thr Gln Pro Gln Ser Pro Ala Gln Pro Glu Val Gln Thr Gln
        2270                2275                2280
```

```
cct gaa gtt cag acc caa aca act gtt tca tcc cat gtc cct tct gaa    7155
Pro Glu Val Gln Thr Gln Thr Thr Val Ser Ser His Val Pro Ser Glu
    2285                2290                2295 gca caa ccc acc cac gca cag tca tcc aag ccc caa gtt gca gca cag    7203
Ala Gln Pro Thr His Ala Gln Ser Ser Lys Pro Gln Val Ala Ala Gln
2300                2305                2310                2315 tct cag cct caa agt aat gtc caa gga cag tct cct gtt cgt gtc caa    7251
Ser Gln Pro Gln Ser Asn Val Gln Gly Gln Ser Pro Val Arg Val Gln
        2320                2325                2330 agt cca tca cag act cga ata cgt cca tca act cca tcc caa ctg tct    7299
Ser Pro Ser Gln Thr Arg Ile Arg Pro Ser Thr Pro Ser Gln Leu Ser
            2335                2340                2345 cct gga caa caa tcc cag gtt cag act aca acc tca caa ccg att cca    7347
Pro Gly Gln Gln Ser Gln Val Gln Thr Thr Thr Ser Gln Pro Ile Pro
                2350                2355                2360 att caa cca cat aca tct ctt cag ata cct tcc caa ggc cag cca cag    7395
Ile Gln Pro His Thr Ser Leu Gln Ile Pro Ser Gln Gly Gln Pro Gln
                    2365                2370                2375 tca caa ccc cag gta cag tct tca act caa act ctt tca tca gga caa    7443
Ser Gln Pro Gln Val Gln Ser Ser Thr Gln Thr Leu Ser Ser Gly Gln
2380                2385                2390                2395 act tta aat caa gtt agt gtt tca tcc cca tcc cgt cct cag cta caa    7491
Thr Leu Asn Gln Val Ser Val Ser Ser Pro Ser Arg Pro Gln Leu Gln
        2400                2405                2410 ata cag cag cca cag ccc caa gtc att gct gtg cct cag ctg caa caa    7539
Ile Gln Gln Pro Gln Pro Gln Val Ile Ala Val Pro Gln Leu Gln Gln
            2415                2420                2425 caa gtc cag gtt ctc tct cag atc cag tca cag gtt gtg gct cag ata    7587
Gln Val Gln Val Leu Ser Gln Ile Gln Ser Gln Val Val Ala Gln Ile
                2430                2435                2440 cag gct cag caa agt ggt gtg ccc cag caa atc aaa ctc cag tta cct    7635
Gln Ala Gln Gln Ser Gly Val Pro Gln Gln Ile Lys Leu Gln Leu Pro
                    2445                2450                2455 atc caa att cag caa agc agt gct gtg cag act cac cag att cag aat    7683
Ile Gln Ile Gln Gln Ser Ser Ala Val Gln Thr His Gln Ile Gln Asn
2460                2465                2470                2475 gtg gtt aca gtg cag gca gcc agt gtg caa gag cag ttg caa agg gtt    7731
Val Val Thr Val Gln Ala Ala Ser Val Gln Glu Gln Leu Gln Arg Val
        2480                2485                2490 cag caa ctc agg gat cag cag caa aag aag aaa cag caa cag ata gaa    7779
Gln Gln Leu Arg Asp Gln Gln Gln Lys Lys Lys Gln Gln Gln Ile Glu
            2495                2500                2505 att aac gtg aac aca ccc tcc aag ctt cta atc aaa gtt gaa atc att    7827
Ile Asn Val Asn Thr Pro Ser Lys Leu Leu Ile Lys Val Glu Ile Ile
                2510                2515                2520 cag aaa cag gtg gtg atg aag cat aat gct gta ata gaa cat tta aaa    7875
Gln Lys Gln Val Val Met Lys His Asn Ala Val Ile Glu His Leu Lys
                    2525                2530                2535 cag aaa aag agc atg act cca gct gaa aga gaa gag aat caa aga atg    7923
Gln Lys Lys Ser Met Thr Pro Ala Glu Arg Glu Glu Asn Gln Arg Met
2540                2545                2550                2555 att gtc tgt aac cag gtg atg aag tat att ttg gat aag ata gat aaa    7971
Ile Val Cys Asn Gln Val Met Lys Tyr Ile Leu Asp Lys Ile Asp Lys
        2560                2565                2570 gaa gaa aaa cag gca gca aaa aaa cgg aag cgt gaa gag agt gtg gag    8019
Glu Glu Lys Gln Ala Ala Lys Lys Arg Lys Arg Glu Glu Ser Val Glu
            2575                2580                2585
```

```
cag aaa cgt agc aag cag aat gcc act aag ctg tca gct ctg ctc ttc      8067
Gln Lys Arg Ser Lys Gln Asn Ala Thr Lys Leu Ser Ala Leu Leu Phe
        2590                2595                2600 aag cac aaa gag cag ctc aga gcc gag atc ctg aag aag aga gca ctc      8115
Lys His Lys Glu Gln Leu Arg Ala Glu Ile Leu Lys Lys Arg Ala Leu
    2605                2610                2615 ctg gac aag gat ctg caa att gaa gtg cag gaa gag ctg aag aga gac      8163
Leu Asp Lys Asp Leu Gln Ile Glu Val Gln Glu Glu Leu Lys Arg Asp
2620                2625                2630                2635 ctg aaa att aag aaa gaa aaa gac ctg atg cag ttg gct cag gcc aca      8211
Leu Lys Ile Lys Lys Glu Lys Asp Leu Met Gln Leu Ala Gln Ala Thr
            2640                2645                2650 gca gta gct gca ccc tgc ccc cca gtg aca cca gtt ctt cca gcc cct      8259
Ala Val Ala Ala Pro Cys Pro Pro Val Thr Pro Val Leu Pro Ala Pro
                2655                2660                2665 cca gcc cct cca cct tca cct ccc cct cca cct ggt gtg caa cac aca      8307
Pro Ala Pro Pro Pro Ser Pro Pro Pro Pro Pro Gly Val Gln His Thr
            2670                2675                2680 ggc ctt ctg tcc acg ccc acc tta cct gtt gct tcc cag aag agg aag      8355
Gly Leu Leu Ser Thr Pro Thr Leu Pro Val Ala Ser Gln Lys Arg Lys
        2685                2690                2695 cgg gaa gag gaa aaa gac tcc agc tca aag tcc aag aaa aag aaa atg      8403
Arg Glu Glu Glu Lys Asp Ser Ser Ser Lys Ser Lys Lys Lys Lys Met
2700                2705                2710                2715 atc tct act acc tca aag gaa act aag aag gac aca aag ctt tac tgt      8451
Ile Ser Thr Thr Ser Lys Glu Thr Lys Lys Asp Thr Lys Leu Tyr Cys
            2720                2725                2730 atc tgt aaa acg cct tat gat gaa tct aaa ttt tat att ggc tgt gat      8499
Ile Cys Lys Thr Pro Tyr Asp Glu Ser Lys Phe Tyr Ile Gly Cys Asp
                2735                2740                2745 cgg tgt cag aat tgg tac cat ggg cgc tgc gtt ggc atc ttg caa agt      8547
Arg Cys Gln Asn Trp Tyr His Gly Arg Cys Val Gly Ile Leu Gln Ser
            2750                2755                2760 gag gca gag ctc att gat gag tat gtc tgt cca cag tgc cag tca aca      8595
Glu Ala Glu Leu Ile Asp Glu Tyr Val Cys Pro Gln Cys Gln Ser Thr
        2765                2770                2775 gag gat gcc atg aca gtg ctc acg cca cta aca gag aag gat tat gag      8643
Glu Asp Ala Met Thr Val Leu Thr Pro Leu Thr Glu Lys Asp Tyr Glu
2780                2785                2790                2795 ggg ttg aag agg gtg ctc cgt tcc tta cag gcc cat aag atg gcc tgg      8691
Gly Leu Lys Arg Val Leu Arg Ser Leu Gln Ala His Lys Met Ala Trp
            2800                2805                2810 cct ttc ctt gaa cca gta gac cct aat gat gca cca gat tat tat ggt      8739
Pro Phe Leu Glu Pro Val Asp Pro Asn Asp Ala Pro Asp Tyr Tyr Gly
                2815                2820                2825 gtt att aag gaa cct atg gac ctt gcc acc atg gaa gaa aga gta caa      8787
Val Ile Lys Glu Pro Met Asp Leu Ala Thr Met Glu Glu Arg Val Gln
            2830                2835                2840 aga cga tat tat gaa aag ctg acg gaa ttt gtg gca gat atg acc aaa      8835
Arg Arg Tyr Tyr Glu Lys Leu Thr Glu Phe Val Ala Asp Met Thr Lys
        2845                2850                2855 att ttt gat aac tgt cgt tac tac aat cca agt gac tcc cca ttt tac      8883
Ile Phe Asp Asn Cys Arg Tyr Tyr Asn Pro Ser Asp Ser Pro Phe Tyr
2860                2865                2870                2875 cag tgt gca gaa gtt ctc gaa tca ttc ttt gta cag aaa ttg aaa ggc      8931
Gln Cys Ala Glu Val Leu Glu Ser Phe Phe Val Gln Lys Leu Lys Gly
            2880                2885                2890
```

```
ttc aaa gct agc agg tct cat aac aac aaa ctg cag tct aca gct tct     8979
Phe Lys Ala Ser Arg Ser His Asn Asn Lys Leu Gln Ser Thr Ala Ser
        2895                2900                2905 taaagttcag cgtgttaacc taacataaaa cacagcaaga atctggttgt ctgaactatt   9039
ttaaattaag gagccagatg tttttagtca ggctatcctg acaagacttg acctaaactt   9099 cgttttatt ggtcataaca gtccaattat attcttggcc aattttgtcc aacggacaag    9159
aaaaaagcaa agtcaacgac accattatct tgtcaagatc agatggtttt actattgtgg   9219
cagaagcgag aaaactttgt ttattgaaaa aaaaagaaaa agaaagcaag aaaaaaagat   9279
actatggggt caagtgtaac tccatggaaa tgccacgtct gctcttcagt gaagaagctg   9339
gtttagagtc tcacagaaaa cttttgactg tatttattta ttgttgcaaa aaagacgctt   9399
ttttattgct gccctcattt gtcagctaag tattttttct tataaaatcc agccccggtt   9459
acatataatc atctgtatct tatcatgatt cctgtaggta aaagtacaag acgacctcta   9519
gatgtctttt ctttctatga aggagctgc tatgtacaca tgtgcacaca cacacaactg    9579
ggaatcaaca atgagtttat tgttcatggt agattaaaat taagcttgca taaaggttgg   9639
gctaagtggt ccttgggcta cagactctgt tgccttgaat ataacagtac aatttgtcaa   9699
ttactctgca ccaggctaaa gtgagtaaaa tctatttgaa ggtatcttgt ttgtaaacat   9759
ttgtcagatt ctaattttt tcttttgtat taaaattcaa ctatggatgt atatgaaaca    9819
aaataaatgg agataatttt tctcccacaa aaaaaaaaa aaaaaa                  9865
```

<210> SEQ ID NO 3
<211> LENGTH: 23
<212> TYPE: DNA
<213> ORGANISM: Artificial Sequence
<220> FEATURE:
<223> OTHER INFORMATION: primer for PCR

<400> SEQUENCE: 3
ggattatgag gggttgaaga ggg                                           23

<210> SEQ ID NO 4
<211> LENGTH: 24
<212> TYPE: DNA
<213> ORGANISM: Artificial Sequence
<220> FEATURE:
<223> OTHER INFORMATION: primer for PCR

<400> SEQUENCE: 4
aaggcaacag agtctgtagc ccaa                                          24

<210> SEQ ID NO 5
<211> LENGTH: 19
<212> TYPE: DNA
<213> ORGANISM: Artificial Sequence
<220> FEATURE:
<223> OTHER INFORMATION: primer for PCR

<400> SEQUENCE: 5
cctcagctgc aacaagtcc                                                19

<210> SEQ ID NO 6
<211> LENGTH: 22
<212> TYPE: DNA
<213> ORGANISM: Artificial Sequence
<220> FEATURE:
<223> OTHER INFORMATION: primer for PCR -continued

```
<400> SEQUENCE: 6
gcactgcttt gctgaatttg ga                                              22

<210> SEQ ID NO 7
<211> LENGTH: 21
<212> TYPE: DNA
<213> ORGANISM: Artificial Sequence
<220> FEATURE:
<223> OTHER INFORMATION: primer for PCR

<400> SEQUENCE: 7
aagatgttgt cttggagccg t                                               21

<210> SEQ ID NO 8
<211> LENGTH: 24
<212> TYPE: DNA
<213> ORGANISM: Artificial Sequence
<220> FEATURE:
<223> OTHER INFORMATION: primer for PCR

<400> SEQUENCE: 8 tttttttacca tttgcttcag tccc                                           24

<210> SEQ ID NO 9
<211> LENGTH: 9700
<212> TYPE: DNA
<213> ORGANISM: Homo sapiens
<220> FEATURE:
<221> NAME/KEY: CDS
<222> LOCATION: (472)...(8814)

<400> SEQUENCE: 9
```

| | | |
|---|---|---|
| agccgccact gcgtccggcc ctccccgtca gctttcccctt ctcccgccgc ctgggctcca | 60 | |
| acaagagggg ccggcggggc aggccgacca agcagcccgc ggctcccgct gcggagcgct | 120 | |
| gcgcccggc cccgccgccg ccgccgccca cgtccggacc catcggggc tcccctcgcc | 180 | |
| gatacgcggt agtagccggg gcaggtgggc agccgccagg ctgaggtggc gcccaagacg | 240 | |
| cggctgagct cgcccagggt gggcagcagt agccggagga agccgccgcc gccgccgccg | 300 | |
| gcccccccca gcaccagcgc cccgggccgg ggggggcgag gaggcggggg cggcacgacg | 360 | |
| ggggggcgggg gcgcggcgg ccacctgtcc cggaccaccg cggcccggag ggccgtcaac | 420 | |
| aaagtggtgt acgatgacca cgagagcgag gcggtggagg aagaggagga c atg gtc | 477 |
| | | Met Val |
| | | 1 |

| | | |
|---|---|---|
| tcc gag gag gag gag gag gag gac ggc gac gcc gag gag acc cag gat | 525 |
| Ser Glu Glu Glu Glu Glu Glu Asp Gly Asp Ala Glu Glu Thr Gln Asp | |
| 5               10              15 | |

| | | |
|---|---|---|
| tct gag gac gac gag gag gat gag atg gaa gag gac gac gat gac tcc | 573 |
| Ser Glu Asp Asp Glu Glu Asp Glu Met Glu Glu Asp Asp Asp Asp Ser | |
| 20              25              30 | |

| | | |
|---|---|---|
| gat tat ccg gag gag atg gaa gac gac gac gac gac gcc agt tac tgc | 621 |
| Asp Tyr Pro Glu Glu Met Glu Asp Asp Asp Asp Asp Ala Ser Tyr Cys | |
| 35              40              45              50 | |

| | | |
|---|---|---|
| acg gaa agc agc ttc agg agc cat agt acc tac agc agc act cca ggt | 669 |
| Thr Glu Ser Ser Phe Arg Ser His Ser Thr Tyr Ser Ser Thr Pro Gly | |
| 55              60              65 | |

| | | |
|---|---|---|
| agg cga aaa cca aga gta cat cgg cct cgt tct cct ata ttg gaa gaa | 717 |
| Arg Arg Lys Pro Arg Val His Arg Pro Arg Ser Pro Ile Leu Glu Glu | |
| 70              75              80 | |

| | | |
|---|---|---|
| aaa gac atc ccg ccc ctt gaa ttt ccc aag tcc tct gag gat tta atg | 765 |
| Lys Asp Ile Pro Pro Leu Glu Phe Pro Lys Ser Ser Glu Asp Leu Met | |

-continued

```
                  85                       90                       95
gtg cct aat gag cat ata atg aat gtc att gcc att tac gag gta ctg        813
Val Pro Asn Glu His Ile Met Asn Val Ile Ala Ile Tyr Glu Val Leu
100                     105                     110 cgg aac ttt ggc act gtt ttg aga tta tct cct ttt cgc ttt gag gac        861
Arg Asn Phe Gly Thr Val Leu Arg Leu Ser Pro Phe Arg Phe Glu Asp
115                     120                     125                 130 ttt tgt gca gct ctg gtg agc caa gag cag tgc aca ctc atg gca gag        909
Phe Cys Ala Ala Leu Val Ser Gln Glu Gln Cys Thr Leu Met Ala Glu
                    135                     140                     145 atg cat gtt gtg ctt ttg aaa gca gtt ctg cgt gaa gaa gac act tcc        957
Met His Val Val Leu Leu Lys Ala Val Leu Arg Glu Glu Asp Thr Ser
            150                     155                     160 aat act acc ttt gga cct gct gat ctg aaa gat agc gtt aat tcc aca       1005
Asn Thr Thr Phe Gly Pro Ala Asp Leu Lys Asp Ser Val Asn Ser Thr
                165                     170                     175 ctg tat ttc ata gat ggg atg acg tgg cca gag gtg ctg cgg gtg tac       1053
Leu Tyr Phe Ile Asp Gly Met Thr Trp Pro Glu Val Leu Arg Val Tyr
180                     185                     190 tgt gag agt gat aag gag tac cat cac gtt ctt cct tac caa gag gca       1101
Cys Glu Ser Asp Lys Glu Tyr His His Val Leu Pro Tyr Gln Glu Ala
195                     200                     205                 210 gag gac tac cca tat gga cca gta gag aac aag atc aaa gtt cta cag       1149
Glu Asp Tyr Pro Tyr Gly Pro Val Glu Asn Lys Ile Lys Val Leu Gln
                    215                     220                     225 ttt cta gtc gat cag ttt ctt aca aca aat att gct cga gag gaa ttg       1197
Phe Leu Val Asp Gln Phe Leu Thr Thr Asn Ile Ala Arg Glu Glu Leu
                230                     235                     240 atg tct gaa ggg gtg ata cag tat gat gac cat tgt agg gtt tgt cac       1245
Met Ser Glu Gly Val Ile Gln Tyr Asp Asp His Cys Arg Val Cys His
            245                     250                     255 aaa ctt ggg gat ttg ctt tgc tgt gag aca tgt tca gca gta tac cat       1293
Lys Leu Gly Asp Leu Leu Cys Cys Glu Thr Cys Ser Ala Val Tyr His
260                     265                     270 ttg gaa tgt gtg aag cca cct ctt gag gag gtg cca gag gac gag tgg       1341
Leu Glu Cys Val Lys Pro Pro Leu Glu Glu Val Pro Glu Asp Glu Trp
275                     280                     285                 290 cag tgt gaa gtc tgt gta gca cac aag gtg cct ggt gtg act gac tgt       1389
Gln Cys Glu Val Cys Val Ala His Lys Val Pro Gly Val Thr Asp Cys
                    295                     300                     305 gtt gct gaa atc caa aaa aat aaa cca tat att cga cat gaa cct att       1437
Val Ala Glu Ile Gln Lys Asn Lys Pro Tyr Ile Arg His Glu Pro Ile
                310                     315                     320 gga tat gat aga agt cgg agg aaa tac tgg ttc ttg aac cga aga ctc       1485
Gly Tyr Asp Arg Ser Arg Arg Lys Tyr Trp Phe Leu Asn Arg Arg Leu
            325                     330                     335 ata ata gaa gaa gat aca gaa aat gaa aat gaa aag aaa att tgg tat       1533
Ile Ile Glu Glu Asp Thr Glu Asn Glu Asn Glu Lys Lys Ile Trp Tyr
340                     345                     350 tac agc aca aag gtc caa ctt gca gaa tta att gac tgt cta gac aaa       1581
Tyr Ser Thr Lys Val Gln Leu Ala Glu Leu Ile Asp Cys Leu Asp Lys
355                     360                     365                 370 gat tat tgg gaa gca gaa ctc tgc aaa att cta gaa gaa atg cgt gaa       1629
Asp Tyr Trp Glu Ala Glu Leu Cys Lys Ile Leu Glu Glu Met Arg Glu
                    375                     380                     385 gaa atc cac cga cac atg gac ata act gaa gac ctg acc aat aag gct       1677
Glu Ile His Arg His Met Asp Ile Thr Glu Asp Leu Thr Asn Lys Ala
                390                     395                     400 cgg ggc agt aac aaa tcc ttt ctg gcg gca gct aat gaa gaa att tgg       1725
```

```
                    Arg Gly Ser Asn Lys Ser Phe Leu Ala Ala Ala Asn Glu Glu Ile Leu
                                    405                 410                 415 gag tcc ata aga gcc aaa aag gga gac att gat aat gtt aaa agc cca          1773
Glu Ser Ile Arg Ala Lys Lys Gly Asp Ile Asp Asn Val Lys Ser Pro
        420                 425                 430 gaa gaa aca gaa aaa gac aag aat gag act gag aat gac tct aaa gat          1821
Glu Glu Thr Glu Lys Asp Lys Asn Glu Thr Glu Asn Asp Ser Lys Asp
435                 440                 445                 450 gct gag aaa aac aga gaa gaa ttt gaa gac cag tcc ctt gaa aaa gac          1869
Ala Glu Lys Asn Arg Glu Glu Phe Glu Asp Gln Ser Leu Glu Lys Asp
                    455                 460                 465 agt gac gac aaa aca cca gat gat gac cct gag caa gga aaa tct gag          1917
Ser Asp Asp Lys Thr Pro Asp Asp Asp Pro Glu Gln Gly Lys Ser Glu
        470                 475                 480 gta ggt gat ttc aaa tcg gag aag tcc aac ggg gag cta agt gaa tct          1965
Val Gly Asp Phe Lys Ser Glu Lys Ser Asn Gly Glu Leu Ser Glu Ser
                485                 490                 495 cct gga gct gga aaa gga gca tct ggc tca act cga atc atc acc aga          2013
Pro Gly Ala Gly Lys Gly Ala Ser Gly Ser Thr Arg Ile Ile Thr Arg
        500                 505                 510 ttg cgg aat cca gat agc aaa ctt agt cag ctg aag agc cag cag gtg          2061
Leu Arg Asn Pro Asp Ser Lys Leu Ser Gln Leu Lys Ser Gln Gln Val
515                 520                 525                 530 gca gcc gct gca cat gaa gca aat aaa tta ttt aag gag ggc aaa gag          2109
Ala Ala Ala Ala His Glu Ala Asn Lys Leu Phe Lys Glu Gly Lys Glu
                    535                 540                 545 gta ctg gta gtt aac tct caa gga gaa att tca cgg ttg agc acc aaa          2157
Val Leu Val Val Asn Ser Gln Gly Glu Ile Ser Arg Leu Ser Thr Lys
        550                 555                 560 aag gaa gtg atc atg aaa gga aat atc aac aat tat ttt aaa ttg ggt          2205
Lys Glu Val Ile Met Lys Gly Asn Ile Asn Asn Tyr Phe Lys Leu Gly
                565                 570                 575 caa gaa ggg aag tat cgc gtc tac cac aat caa tac tcc acc aat tca          2253
Gln Glu Gly Lys Tyr Arg Val Tyr His Asn Gln Tyr Ser Thr Asn Ser
        580                 585                 590 ttt gct ttg aat aag cac cag cac aga gaa gac cat gat aag aga agg          2301
Phe Ala Leu Asn Lys His Gln His Arg Glu Asp His Asp Lys Arg Arg
595                 600                 605                 610 cat ctt gca cat aag ttc tgt ctg act cca gca gga gag ttc aaa tgg          2349
His Leu Ala His Lys Phe Cys Leu Thr Pro Ala Gly Glu Phe Lys Trp
                    615                 620                 625 aac ggt tct gtc cat ggg tcc aaa gtt ctt acc ata tct act ctg aga          2397
Asn Gly Ser Val His Gly Ser Lys Val Leu Thr Ile Ser Thr Leu Arg
        630                 635                 640 ctg act atc acc caa tta gaa aac aac atc cct tca tcc ttt ctt cat          2445
Leu Thr Ile Thr Gln Leu Glu Asn Asn Ile Pro Ser Ser Phe Leu His
                645                 650                 655 ccc aac tgg gca tca cat agg gca aat tgg atc aag gca gtt cag atg          2493
Pro Asn Trp Ala Ser His Arg Ala Asn Trp Ile Lys Ala Val Gln Met
        660                 665                 670 tgt agc aaa ccc aga gaa ttt gca ttg gct tta gcc att ttg gag tgt          2541
Cys Ser Lys Pro Arg Glu Phe Ala Leu Ala Leu Ala Ile Leu Glu Cys
675                 680                 685                 690 gca gtt aaa cca gtt gtg atg cta cca ata tgg cga gaa ttt tta gga          2589
Ala Val Lys Pro Val Val Met Leu Pro Ile Trp Arg Glu Phe Leu Gly
                    695                 700                 705 cat acc agg tta cac cgg atg aca tca att gaa aga gaa gaa aag gag          2637
His Thr Arg Leu His Arg Met Thr Ser Ile Glu Arg Glu Glu Lys Glu
        710                 715                 720
```

```
aaa gtc aaa aaa aaa gag aag aaa cag gaa gaa gaa gaa acg atg cag    2685
Lys Val Lys Lys Lys Glu Lys Lys Gln Glu Glu Glu Glu Thr Met Gln
        725                 730                 735 caa gcg aca tgg gta aaa tac aca ttt cca gtt aag cat cag gtt tgg    2733
Gln Ala Thr Trp Val Lys Tyr Thr Phe Pro Val Lys His Gln Val Trp
    740                 745                 750 aaa caa aaa ggt gaa gag tac aga gtg aca gga tat ggt ggt tgg agc    2781
Lys Gln Lys Gly Glu Glu Tyr Arg Val Thr Gly Tyr Gly Gly Trp Ser
755                 760                 765                 770 tgg att agt aaa act cat gtt tat agg ttt gtt cct aaa ttg cca ggc    2829
Trp Ile Ser Lys Thr His Val Tyr Arg Phe Val Pro Lys Leu Pro Gly
            775                 780                 785 aat act aat gtg aat tac aga aag tcg tta gaa gga acc aaa aat aat    2877
Asn Thr Asn Val Asn Tyr Arg Lys Ser Leu Glu Gly Thr Lys Asn Asn
        790                 795                 800 atg gat gaa aat atg gat gag tca gat aaa aga aaa tgt tca cga agt    2925
Met Asp Glu Asn Met Asp Glu Ser Asp Lys Arg Lys Cys Ser Arg Ser
    805                 810                 815 cca aaa aaa ata aaa ata gag cct gat tct gaa aaa gat gag gta aaa    2973
Pro Lys Lys Ile Lys Ile Glu Pro Asp Ser Glu Lys Asp Glu Val Lys
820                 825                 830 ggt tca gat gct gca aaa gga gca gac caa aat gaa atg gat atc tca    3021
Gly Ser Asp Ala Ala Lys Gly Ala Asp Gln Asn Glu Met Asp Ile Ser
835                 840                 845                 850 aag att act gag aag aag gac caa gat gtg aag gag ctc tta gat tct    3069
Lys Ile Thr Glu Lys Lys Asp Gln Asp Val Lys Glu Leu Leu Asp Ser
            855                 860                 865 gac agt gat aaa ccc tgc aag gaa gaa cca atg gaa gta gac gat gac    3117
Asp Ser Asp Lys Pro Cys Lys Glu Glu Pro Met Glu Val Asp Asp Asp
        870                 875                 880 atg aaa aca gag tca cat gta aat tgt cag gag agt tct caa gta gat    3165
Met Lys Thr Glu Ser His Val Asn Cys Gln Glu Ser Ser Gln Val Asp
    885                 890                 895 gtg gtc aat gtt agt gag ggt ttt cat cta agg act agt tac aaa aag    3213
Val Val Asn Val Ser Glu Gly Phe His Leu Arg Thr Ser Tyr Lys Lys
900                 905                 910 aaa aca aaa tca tcc aaa cta gat gga ctt ctt gaa agg aga att aaa    3261
Lys Thr Lys Ser Ser Lys Leu Asp Gly Leu Leu Glu Arg Arg Ile Lys
915                 920                 925                 930 cag ttt aca ctg gaa gaa aaa cag cga ctc gaa aaa atc aag ttg gag    3309
Gln Phe Thr Leu Glu Glu Lys Gln Arg Leu Glu Lys Ile Lys Leu Glu
            935                 940                 945 ggt gga att aag ggt ata gga aag act tct aca aat tct tca aaa aat    3357
Gly Gly Ile Lys Gly Ile Gly Lys Thr Ser Thr Asn Ser Ser Lys Asn
        950                 955                 960 ctc tct gaa tca cca gta ata acg aaa gca aaa gaa ggg tgt cag agt    3405
Leu Ser Glu Ser Pro Val Ile Thr Lys Ala Lys Glu Gly Cys Gln Ser
    965                 970                 975 gac tcg atg aga caa gaa cag agc cca aat gca aat aat gat caa cct    3453
Asp Ser Met Arg Gln Glu Gln Ser Pro Asn Ala Asn Asn Asp Gln Pro
980                 985                 990 gag gac ttg att cag gga tgt tca caa agt gat tcc tca gtt ctt aga    3501
Glu Asp Leu Ile Gln Gly Cys Ser Gln Ser Asp Ser Ser Val Leu Arg
995                 1000                1005                1010 atg agt gat cct agt cat acc aca aac aaa ctt tat cca aaa gat cga    3549
Met Ser Asp Pro Ser His Thr Thr Asn Lys Leu Tyr Pro Lys Asp Arg
            1015                1020                1025 gtg tta gat gat gtc tcc att cgg agc cca gaa aca aaa tgt ccg aaa    3597
Val Leu Asp Asp Val Ser Ile Arg Ser Pro Glu Thr Lys Cys Pro Lys
        1030                1035                1040
```

```
caa aat tcc att gaa aat gac ata gaa gaa aaa gtc tct gac ctt gcc    3645
Gln Asn Ser Ile Glu Asn Asp Ile Glu Glu Lys Val Ser Asp Leu Ala
        1045                1050                1055 agt aga ggc cag gaa ccc act aag agt aaa acc aaa gga aat gat ttt    3693
Ser Arg Gly Gln Glu Pro Thr Lys Ser Lys Thr Lys Gly Asn Asp Phe
1060                1065                1070 ttc atc gat gac tct aaa cta gcc agt gca gat gat att ggt act ttg    3741
Phe Ile Asp Asp Ser Lys Leu Ala Ser Ala Asp Asp Ile Gly Thr Leu
1075                1080                1085                1090 atc tgt aag aac aaa aaa ccg ctc ata cag gag gaa agt gac acc att    3789
Ile Cys Lys Asn Lys Lys Pro Leu Ile Gln Glu Glu Ser Asp Thr Ile
        1095                1100                1105 gtt tct tct tcc aag agt gct tta cat tca tca gtg cct aaa agt acc    3837
Val Ser Ser Ser Lys Ser Ala Leu His Ser Ser Val Pro Lys Ser Thr
        1110                1115                1120 aat gac aga gat gcc aca cct ctg tca aga gca atg gac ttt gaa gga    3885
Asn Asp Arg Asp Ala Thr Pro Leu Ser Arg Ala Met Asp Phe Glu Gly
        1125                1130                1135 aaa ctg gga tgt gac tct gaa tct aat agc act ttg gaa aat agt tct    3933
Lys Leu Gly Cys Asp Ser Glu Ser Asn Ser Thr Leu Glu Asn Ser Ser
        1140                1145                1150 gat acc gtg tct att cag gat agc agt gaa gaa gat atg att gtt cag    3981
Asp Thr Val Ser Ile Gln Asp Ser Ser Glu Glu Asp Met Ile Val Gln
1155                1160                1165                1170 aat agc aat gaa agc att tct gaa cag ttc aga act cga gaa caa gat    4029
Asn Ser Asn Glu Ser Ile Ser Glu Gln Phe Arg Thr Arg Glu Gln Asp
            1175                1180                1185 gtt gaa gtc ttg gag ccg tta aag tgt gag ttg gtt tct ggt gag tcc    4077
Val Glu Val Leu Glu Pro Leu Lys Cys Glu Leu Val Ser Gly Glu Ser
            1190                1195                1200 act gga aac tgt gag gac agg ctg ccg gtc aag ggg act gaa gca aat    4125
Thr Gly Asn Cys Glu Asp Arg Leu Pro Val Lys Gly Thr Glu Ala Asn
        1205                1210                1215 ggt aaa aaa cca agt cag cag aag aaa tta gag gag aga cca gtt aat    4173
Gly Lys Lys Pro Ser Gln Gln Lys Lys Leu Glu Glu Arg Pro Val Asn
        1220                1225                1230 aaa tgt agt gat caa ata aag cta aaa aat acc act gac aaa aag aat    4221
Lys Cys Ser Asp Gln Ile Lys Leu Lys Asn Thr Thr Asp Lys Lys Asn
1235                1240                1245                1250 aat gaa aat cga gag tct gaa aag aaa gga cag aga aca agt aca ttt    4269
Asn Glu Asn Arg Glu Ser Glu Lys Lys Gly Gln Arg Thr Ser Thr Phe
            1255                1260                1265 caa ata aat gga aaa gat aat aaa ccc aaa ata tat ttg aaa ggt gaa    4317
Gln Ile Asn Gly Lys Asp Asn Lys Pro Lys Ile Tyr Leu Lys Gly Glu
        1270                1275                1280 tgc ttg aaa gaa att tct gag agt aga gta gta agt ggt aat gtt gaa    4365
Cys Leu Lys Glu Ile Ser Glu Ser Arg Val Val Ser Gly Asn Val Glu
        1285                1290                1295 cca aag gtt aat aat ata aat aaa ata atc cct gag aat gat att aaa    4413
Pro Lys Val Asn Asn Ile Asn Lys Ile Ile Pro Glu Asn Asp Ile Lys
        1300                1305                1310 tca ttg act gtt aaa gaa tct gct ata agg cca ttc att aat ggt gat    4461
Ser Leu Thr Val Lys Glu Ser Ala Ile Arg Pro Phe Ile Asn Gly Asp
1315                1320                1325                1330 gtc atc atg gaa gat ttt aat gaa aga aac agc tcc gaa aca aaa tcg    4509
Val Ile Met Glu Asp Phe Asn Glu Arg Asn Ser Ser Glu Thr Lys Ser
            1335                1340                1345
```

```
cat ttg ctg agt tct tca gat gct gaa ggt aac tac cga gat agc ctt      4557
His Leu Leu Ser Ser Ser Asp Ala Glu Gly Asn Tyr Arg Asp Ser Leu
            1350                1355                1360 gag acc ctg cca tca acc aaa gag tct gac agt aca cag acg acc aca      4605
Glu Thr Leu Pro Ser Thr Lys Glu Ser Asp Ser Thr Gln Thr Thr Thr
        1365                1370                1375 ccc tca gca tct tgt cca gaa agc aat tca gtt aat cag gta gaa gat      4653
Pro Ser Ala Ser Cys Pro Glu Ser Asn Ser Val Asn Gln Val Glu Asp
        1380                1385                1390 atg gaa ata gaa acc tca gaa gtt aag aaa gtt act tca tca cct att      4701
Met Glu Ile Glu Thr Ser Glu Val Lys Lys Val Thr Ser Ser Pro Ile
1395                1400                1405                1410 act tct gaa gag gaa tct aat ctc agt aat gac ttt att gat gaa aat      4749
Thr Ser Glu Glu Glu Ser Asn Leu Ser Asn Asp Phe Ile Asp Glu Asn
            1415                1420                1425 ggt ctg ccc atc aac aaa aat gaa aat gtc aat gga gaa tct aaa aga      4797
Gly Leu Pro Ile Asn Lys Asn Glu Asn Val Asn Gly Glu Ser Lys Arg
        1430                1435                1440 aaa acc gtc atc aca gaa gtc acc acg atg acc tcc aca gtg gcc aca      4845
Lys Thr Val Ile Thr Glu Val Thr Thr Met Thr Ser Thr Val Ala Thr
        1445                1450                1455 gaa tca aaa act gtg atc aag gta gaa aaa ggc gat aag caa act gtg      4893
Glu Ser Lys Thr Val Ile Lys Val Glu Lys Gly Asp Lys Gln Thr Val
        1460                1465                1470 gtt tct tcc aca gaa aat tgt gca aaa tcc act gtc aca acc acc act      4941
Val Ser Ser Thr Glu Asn Cys Ala Lys Ser Thr Val Thr Thr Thr Thr
1475                1480                1485                1490 aca aca gtg acc aag ctt tcc aca ccc tcc aca ggc ggc agt gtg gac      4989
Thr Thr Val Thr Lys Leu Ser Thr Pro Ser Thr Gly Gly Ser Val Asp
            1495                1500                1505 atc atc tct gta aag gag cag agc aaa acc gtg gtc acc acg aca gtg      5037
Ile Ile Ser Val Lys Glu Gln Ser Lys Thr Val Val Thr Thr Thr Val
        1510                1515                1520 aca gac tcc ctg acc acc acg gga ggc aca ctg gtt aca tct atg act      5085
Thr Asp Ser Leu Thr Thr Thr Gly Gly Thr Leu Val Thr Ser Met Thr
        1525                1530                1535 gtg agc aaa gag tat tcc aca cga gac aaa gtg aaa ctg atg aaa ttt      5133
Val Ser Lys Glu Tyr Ser Thr Arg Asp Lys Val Lys Leu Met Lys Phe
        1540                1545                1550 tca aga cca aag aag act cgt tca ggt aca gct ctg cca tcc tat aga      5181
Ser Arg Pro Lys Lys Thr Arg Ser Gly Thr Ala Leu Pro Ser Tyr Arg
1555                1560                1565                1570 aaa ttt gtt acc aag agc acc aag aag agc att ttt gtt ttg cct aat      5229
Lys Phe Val Thr Lys Ser Thr Lys Lys Ser Ile Phe Val Leu Pro Asn
            1575                1580                1585 gat gac tta aaa aag ttg gcc cga aaa gga gga atc cga gag gtc cct      5277
Asp Asp Leu Lys Lys Leu Ala Arg Lys Gly Gly Ile Arg Glu Val Pro
        1590                1595                1600 tat ttt aat tac aat gca aaa cct gct ttg gat ata tgg cca tat cct      5325
Tyr Phe Asn Tyr Asn Ala Lys Pro Ala Leu Asp Ile Trp Pro Tyr Pro
        1605                1610                1615 tct cct aga ccg acc ttt ggc atc act tgg agg tat aga ctt cag aca      5373
Ser Pro Arg Pro Thr Phe Gly Ile Thr Trp Arg Tyr Arg Leu Gln Thr
        1620                1625                1630 gta aag tcc tta gct gga gtg agc ctg atg tta cgg tta ctg tgg gca      5421
Val Lys Ser Leu Ala Gly Val Ser Leu Met Leu Arg Leu Leu Trp Ala
1635                1640                1645                1650
```

-continued

| | |
|---|---|
| agt ttg aga tgg gat gat atg gcg gcc aag gtt cct cca gga gga ggg<br>Ser Leu Arg Trp Asp Asp Met Ala Ala Lys Val Pro Pro Gly Gly Gly<br>               1655                      1660                      1665 | 5469 |
| agt aca cgg aca gaa aca tcc gaa act gaa atc aca aca aca gaa ata<br>Ser Thr Arg Thr Glu Thr Ser Glu Thr Glu Ile Thr Thr Thr Glu Ile<br>               1670                      1675                      1680 | 5517 |
| att aag agg aga gat gtt ggt cct tat ggc att cga ttt gaa tat tgt<br>Ile Lys Arg Arg Asp Val Gly Pro Tyr Gly Ile Arg Phe Glu Tyr Cys<br>               1685                      1690                      1695 | 5565 |
| atc agg aaa atc att tgt ccc att gga gtt cca gaa aca cca aaa gaa<br>Ile Arg Lys Ile Ile Cys Pro Ile Gly Val Pro Glu Thr Pro Lys Glu<br>        1700                      1705                      1710 | 5613 |
| acg cct aca cct cag agg aaa ggc ctt cga tca agt gca ctg cgg cca<br>Thr Pro Thr Pro Gln Arg Lys Gly Leu Arg Ser Ser Ala Leu Arg Pro<br>1715                      1720                      1725                      1730 | 5661 |
| aag aga cca gaa acg ccc aag caa act ggc cct gtt att att gaa acc<br>Lys Arg Pro Glu Thr Pro Lys Gln Thr Gly Pro Val Ile Ile Glu Thr<br>               1735                      1740                      1745 | 5709 |
| tgg gta gca gaa gaa gaa ctg gaa ttg tgg gag atc agg gca ttt gct<br>Trp Val Ala Glu Glu Glu Leu Glu Leu Trp Glu Ile Arg Ala Phe Ala<br>        1750                      1755                      1760 | 5757 |
| gag aga gtg gag aaa gaa aag gca caa gca gtt gag caa cag gct aag<br>Glu Arg Val Glu Lys Glu Lys Ala Gln Ala Val Glu Gln Gln Ala Lys<br>               1765                      1770                      1775 | 5805 |
| aaa cga ctg gag cag cag aag ccg aca gtg att gca act tcc act act<br>Lys Arg Leu Glu Gln Gln Lys Pro Thr Val Ile Ala Thr Ser Thr Thr<br>        1780                      1785                      1790 | 5853 |
| tcc cca aca agc agt aca acc agc acc atc tct cca gca cag aaa gtt<br>Ser Pro Thr Ser Ser Thr Thr Ser Thr Ile Ser Pro Ala Gln Lys Val<br>1795                      1800                      1805                      1810 | 5901 |
| atg gtg gcc ccc ata agt ggc tca gtt aca act gga acc aaa atg gta<br>Met Val Ala Pro Ile Ser Gly Ser Val Thr Thr Gly Thr Lys Met Val<br>               1815                      1820                      1825 | 5949 |
| cta act act aaa gtt gga tct cca gct aca gta aca ttc caa caa aac<br>Leu Thr Thr Lys Val Gly Ser Pro Ala Thr Val Thr Phe Gln Gln Asn<br>        1830                      1835                      1840 | 5997 |
| aag aac ttt cat caa acc ttt gct aca tgg gtt aag caa ggc cag tca<br>Lys Asn Phe His Gln Thr Phe Ala Thr Trp Val Lys Gln Gly Gln Ser<br>               1845                      1850                      1855 | 6045 |
| aat tca ggc gtt gtt caa gta cag cag aaa gtc ctg ggt atc att cca<br>Asn Ser Gly Val Val Gln Val Gln Gln Lys Val Leu Gly Ile Ile Pro<br>        1860                      1865                      1870 | 6093 |
| tca agt aca ggt acc agt cag caa acc ttt act tca ttc cag ccc agg<br>Ser Ser Thr Gly Thr Ser Gln Gln Thr Phe Thr Ser Phe Gln Pro Arg<br>1875                      1880                      1885                      1890 | 6141 |
| aca gca aca gtc aca att agg ccc aat acc tca ggc tct gga gga acc<br>Thr Ala Thr Val Thr Ile Arg Pro Asn Thr Ser Gly Ser Gly Gly Thr<br>               1895                      1900                      1905 | 6189 |
| aca agc aat tca caa gta atc aca ggg cct cag att cgc cct ggt atg<br>Thr Ser Asn Ser Gln Val Ile Thr Gly Pro Gln Ile Arg Pro Gly Met<br>        1910                      1915                      1920 | 6237 |
| acc gtg att aga aca cca ctc caa cag tca aca cta gga aag gca att<br>Thr Val Ile Arg Thr Pro Leu Gln Gln Ser Thr Leu Gly Lys Ala Ile<br>               1925                      1930                      1935 | 6285 |
| att cga aca cct gtg atg gta cag cca ggt gct cct cag caa gtg atg<br>Ile Arg Thr Pro Val Met Val Gln Pro Gly Ala Pro Gln Gln Val Met<br>        1940                      1945                      1950 | 6333 |

```
act caa atc atc agg ggg cag cct gtc tcc act gca gtc tcc gcc cct     6381
Thr Gln Ile Ile Arg Gly Gln Pro Val Ser Thr Ala Val Ser Ala Pro
1955                1960                1965                1970 aac acg gtt tcc tca aca cct ggg cag aaa agc tta act tca gca acg     6429
Asn Thr Val Ser Ser Thr Pro Gly Gln Lys Ser Leu Thr Ser Ala Thr
            1975                1980                1985 tcc act tca aat ata cag tct tca gcc tca caa ccc cct cgc ccc caa     6477
Ser Thr Ser Asn Ile Gln Ser Ser Ala Ser Gln Pro Pro Arg Pro Gln
        1990                1995                2000 caa gga caa gtg aag ctc acc atg gct caa ctt act cag tta aca cag     6525
Gln Gly Gln Val Lys Leu Thr Met Ala Gln Leu Thr Gln Leu Thr Gln
    2005                2010                2015 ggc cac ggt ggc aat caa ggt ttg aca gta gta att caa gga caa ggt     6573
Gly His Gly Gly Asn Gln Gly Leu Thr Val Val Ile Gln Gly Gln Gly
2020                2025                2030 caa act act gga cag ttg cag ttg ata cct caa ggg gtg act gta ctc     6621
Gln Thr Thr Gly Gln Leu Gln Leu Ile Pro Gln Gly Val Thr Val Leu
2035                2040                2045                2050 cca ggc cca ggc cag cag cta atg caa gct gca atg cca aat ggt act     6669
Pro Gly Pro Gly Gln Gln Leu Met Gln Ala Ala Met Pro Asn Gly Thr
            2055                2060                2065 gtt cag cga ttc ctc ttt acc cca ttg gca aca aca gcc acc aca gcc     6717
Val Gln Arg Phe Leu Phe Thr Pro Leu Ala Thr Thr Ala Thr Thr Ala
        2070                2075                2080 agc acc acc acc acc act gtt tcc acg aca gca gca ggt aca ggt gaa     6765
Ser Thr Thr Thr Thr Thr Val Ser Thr Thr Ala Ala Gly Thr Gly Glu
    2085                2090                2095 caa agg cag agt aaa ctg tca ccc cag atg cag gta cat caa gac aaa     6813
Gln Arg Gln Ser Lys Leu Ser Pro Gln Met Gln Val His Gln Asp Lys
2100                2105                2110 acc ctg cca cca gct cag tca tca agt gtg ggt cca gca aaa gcc cag     6861
Thr Leu Pro Pro Ala Gln Ser Ser Ser Val Gly Pro Ala Lys Ala Gln
2115                2120                2125                2130 cca cag act gct cag cct tca gct cgg ccc cag ccc caa acc cag ccc     6909
Pro Gln Thr Ala Gln Pro Ser Ala Arg Pro Gln Pro Gln Thr Gln Pro
            2135                2140                2145 cag tcc cca gct cag cct gaa gtt cag act cag cct gaa gtt cag acc     6957
Gln Ser Pro Ala Gln Pro Glu Val Gln Thr Gln Pro Glu Val Gln Thr
        2150                2155                2160 caa aca act gtt tca tcc cat gtc cct tct gaa gca caa ccc acc cac     7005
Gln Thr Thr Val Ser Ser His Val Pro Ser Glu Ala Gln Pro Thr His
    2165                2170                2175 gca cag tca tcc aag ccc caa gtt gca gca cag tct cag cct caa agt     7053
Ala Gln Ser Ser Lys Pro Gln Val Ala Ala Gln Ser Gln Pro Gln Ser
2180                2185                2190 aat gtc caa gga cag tct cct gtt cgt gtc caa agt cca tca cag act     7101
Asn Val Gln Gly Gln Ser Pro Val Arg Val Gln Ser Pro Ser Gln Thr
2195                2200                2205                2210 cga ata cgt cca tca act cca tcc caa ctg tct cct gga caa caa tcc     7149
Arg Ile Arg Pro Ser Thr Pro Ser Gln Leu Ser Pro Gly Gln Gln Ser
            2215                2220                2225 cag gtt cag act aca acc tca caa ccg att cca att caa cca cat aca     7197
Gln Val Gln Thr Thr Thr Ser Gln Pro Ile Pro Ile Gln Pro His Thr
        2230                2235                2240 tct ctt cag ata cct tcc caa ggc cag cca cag tca caa ccc cag gta     7245
Ser Leu Gln Ile Pro Ser Gln Gly Gln Pro Gln Ser Gln Pro Gln Val
    2245                2250                2255
```

-continued

| | |
|---|---|
| cag tct tca act caa act ctt tca tca gga caa act tta aat caa gtt<br>Gln Ser Ser Thr Gln Thr Leu Ser Ser Gly Gln Thr Leu Asn Gln Val<br>    2260                      2265                      2270 | 7293 |
| agt gtt tca tcc cca tcc cgt cct cag cta caa ata cag cag cca cag<br>Ser Val Ser Ser Pro Ser Arg Pro Gln Leu Gln Ile Gln Gln Pro Gln<br>2275                      2280                      2285                      2290 | 7341 |
| ccc caa gtc att gct gtg cct cag ctg caa caa caa gtc cag gtt ctc<br>Pro Gln Val Ile Ala Val Pro Gln Leu Gln Gln Gln Val Gln Val Leu<br>    2295                      2300                      2305 | 7389 |
| tct cag atc cag tca cag gtt gtg gct cag ata cag gct cag caa agt<br>Ser Gln Ile Gln Ser Gln Val Val Ala Gln Ile Gln Ala Gln Gln Ser<br>           2310                      2315                      2320 | 7437 |
| ggt gtg ccc cag caa atc aaa ctc cag tta cct atc caa att cag caa<br>Gly Val Pro Gln Gln Ile Lys Leu Gln Leu Pro Ile Gln Ile Gln Gln<br>                2325                      2330                      2335 | 7485 |
| agc agt gct gtg cag act cac cag att cag aat gtg gtt aca gtg cag<br>Ser Ser Ala Val Gln Thr His Gln Ile Gln Asn Val Val Thr Val Gln<br>                    2340                      2345                      2350 | 7533 |
| gca gcc agt gtg caa gag cag ttg caa agg gtt cag caa ctc agg gat<br>Ala Ala Ser Val Gln Glu Gln Leu Gln Arg Val Gln Gln Leu Arg Asp<br>2355                      2360                      2365                      2370 | 7581 |
| cag cag caa aag aag aaa cag caa cag ata gaa att aag cgt gaa cac<br>Gln Gln Gln Lys Lys Lys Gln Gln Gln Ile Glu Ile Lys Arg Glu His<br>                      2375                      2380                      2385 | 7629 |
| acc ctc caa gct tct aat caa agt gaa atc att cag aaa cag gtg gtg<br>Thr Leu Gln Ala Ser Asn Gln Ser Glu Ile Ile Gln Lys Gln Val Val<br>                    2390                      2395                      2400 | 7677 |
| atg aag cat aat gct gta ata gaa cat tta aaa cag aaa aag agc atg<br>Met Lys His Asn Ala Val Ile Glu His Leu Lys Gln Lys Lys Ser Met<br>              2405                      2410                      2415 | 7725 |
| act cca gct gaa aga gaa gag aat caa aga atg att gtc tgt aac cag<br>Thr Pro Ala Glu Arg Glu Glu Asn Gln Arg Met Ile Val Cys Asn Gln<br>2420                      2425                      2430 | 7773 |
| gtg atg aag tat att ttg gat aag ata gat aaa gaa gaa aaa cag gca<br>Val Met Lys Tyr Ile Leu Asp Lys Ile Asp Lys Glu Glu Lys Gln Ala<br>2435                      2440                      2445                      2450 | 7821 |
| gca aaa aaa cgg aag cgt gaa gag agt gtg gag cag aaa cgt agc aag<br>Ala Lys Lys Arg Lys Arg Glu Glu Ser Val Glu Gln Lys Arg Ser Lys<br>                    2455                      2460                      2465 | 7869 |
| cag aat gcc act aag ctg tca gct ctg ctc ttc aag cac aaa gag cag<br>Gln Asn Ala Thr Lys Leu Ser Ala Leu Leu Phe Lys His Lys Glu Gln<br>                2470                      2475                      2480 | 7917 |
| ctc aga gcc gag atc ctg aag aag aga gca ctc ctg gac aag gat ctg<br>Leu Arg Ala Glu Ile Leu Lys Lys Arg Ala Leu Leu Asp Lys Asp Leu<br>            2485                      2490                      2495 | 7965 |
| caa att gaa gtg cag gaa gag ctg aag aga gac ctg aaa att aag aaa<br>Gln Ile Glu Val Gln Glu Glu Leu Lys Arg Asp Leu Lys Ile Lys Lys<br>2500                      2505                      2510 | 8013 |
| gaa aaa gac ctg atg cag ttg gct cag gcc aca gca gta gct gca ccc<br>Glu Lys Asp Leu Met Gln Leu Ala Gln Ala Thr Ala Val Ala Ala Pro<br>2515                      2520                      2525                      2530 | 8061 |
| tgc ccc cca gtg aca cca gtt ctt cca gcc cct cca gcc cct cca cct<br>Cys Pro Pro Val Thr Pro Val Leu Pro Ala Pro Pro Ala Pro Pro Pro<br>                    2535                      2540                      2545 | 8109 |
| tca cct ccc cct cca cct ggt gtg caa cac aca ggc ctt ctg tcc acg<br>Ser Pro Pro Pro Pro Pro Gly Val Gln His Thr Gly Leu Leu Ser Thr<br>                2550                      2555                      2560 | 8157 |
| ccc acc tta cct gtt gct tcc cag aag agg aag cgg gaa gag gaa aaa<br>Pro Thr Leu Pro Val Ala Ser Gln Lys Arg Lys Arg Glu Glu Glu Lys | 8205 |

-continued

```
                2565                2570                2575
gac tcc agc tca aag tcc aag aaa aag aaa atg atc tct act acc tca        8253
Asp Ser Ser Lys Ser Lys Lys Lys Met Ile Ser Thr Thr Ser
        2580                2585                2590 aag gaa act aag aag gac aca aag ctt tac tgt atc tgt aaa acg cct        8301
Lys Glu Thr Lys Lys Asp Thr Lys Leu Tyr Cys Ile Cys Lys Thr Pro
2595                2600                2605                2610 tat gat gaa tct aaa ttt tat att ggc tgt gat cgg tgt cag aat tgg        8349
Tyr Asp Glu Ser Lys Phe Tyr Ile Gly Cys Asp Arg Cys Gln Asn Trp
                2615                2620                2625 tac cat ggg cgc tgc gtt ggc atc ttg caa agt gag gca gag ctc att        8397
Tyr His Gly Arg Cys Val Gly Ile Leu Gln Ser Glu Ala Glu Leu Ile
        2630                2635                2640 gat gag tat gtc tgt cca cag tgc cag tca aca gag gat gcc atg aca        8445
Asp Glu Tyr Val Cys Pro Gln Cys Gln Ser Thr Glu Asp Ala Met Thr
        2645                2650                2655 gtg ctc acg cca cta aca gag aag gat tat gag ggg ttg aag agg gtg        8493
Val Leu Thr Pro Leu Thr Glu Lys Asp Tyr Glu Gly Leu Lys Arg Val
        2660                2665                2670 ctc cgt tcc tta cag gcc cat aag atg gcc tgg cct ttc ctt gaa cca        8541
Leu Arg Ser Leu Gln Ala His Lys Met Ala Trp Pro Phe Leu Glu Pro
2675                2680                2685                2690 gta gac cct aat gat gca cca gat tat tat ggt gtt att aag gaa cct        8589
Val Asp Pro Asn Asp Ala Pro Asp Tyr Tyr Gly Val Ile Lys Glu Pro
                2695                2700                2705 atg gac ctt gcc acc atg gaa gaa aga gta caa aga cga tat tat gaa        8637
Met Asp Leu Ala Thr Met Glu Glu Arg Val Gln Arg Arg Tyr Tyr Glu
        2710                2715                2720 aag ctg acg gaa ttt gtg gca gat atg acc aaa att ttt gat aac tgt        8685
Lys Leu Thr Glu Phe Val Ala Asp Met Thr Lys Ile Phe Asp Asn Cys
        2725                2730                2735 cgt tac tac aat cca agt gac tcc cca ttt tac cag tgt gca gaa gtt        8733
Arg Tyr Tyr Asn Pro Ser Asp Ser Pro Phe Tyr Gln Cys Ala Glu Val
        2740                2745                2750 ctc gaa tca ttc ttt gta cag aaa ttg aaa ggc ttc aaa gct agc agg        8781
Leu Glu Ser Phe Phe Val Gln Lys Leu Lys Gly Phe Lys Ala Ser Arg
2755                2760                2765                2770 tct cat aac aac aaa ctg cag tct aca gct tct taaagttcag cgtgttaacc     8834
Ser His Asn Asn Lys Leu Gln Ser Thr Ala Ser
                2775                2780 taacataaaa cacagcaaga atctggttgt ctgaactatt ttaaattaag gagccagatg     8894
tttttagtca ggctatcctg acaagacttg acctaaactt cgtttttatt ggtcataaca     8954
gtccaattat attcttggcc aattttgtcc aacggacaag aaaaaagcaa agtcaacgac     9014
accattatct tgtcaagatc agatggtttt actattgtgg cagaagcgag aaaactttgt     9074
ttattgaaaa aaaagaaaa agaaagcaag aaaaaaagat actatggggt caagtgtaac     9134
tccatggaaa tgccacgtct gctcttcagt gaagaagctg gtttagagtc tcacagaaaa     9194
cttttgactg tatttattta ttgttgcaaa aaagacgctt ttttattgct gccctcattt     9254
gtcagctaag tatttttcct tataaaatcc agccccggtt acatataatc atctgtatct     9314
tatcatgatt cctgtaggta aaagtacaag acgacctcta gatgtctttt ctttctatga     9374
aaggagctgc tatgtacaca tgtgcacaca cacacaactg ggaatcaaca atgagtttat     9434
tgttcatggt agattaaaat taagcttgca taaaggttgg gctaagtggt ccttgggcta     9494
cagactctgt tgccttgaat ataacagtac aattttgtcaa ttactctgca ccaggctaaa    9554
gtgagtaaaa tctatttgaa ggtatcttgt ttgtaaacat ttgtcagatt ctaattttttt    9614
```

-continued

```
tcttttgtat taaaattcaa ctatggatgt atatgaaaca aaataaatgg agataatttt    9674
tctcccacaa aaaaaaaaaa aaaaaa                                         9700
```

<210> SEQ ID NO 10
<211> LENGTH: 2781
<212> TYPE: PRT
<213> ORGANISM: Homo sapiens

<400> SEQUENCE: 10

```
Met Val Ser Glu Glu Glu Glu Asp Gly Asp Ala Glu Thr
 1               5                  10              15

Gln Asp Ser Glu Asp Glu Glu Asp Glu Glu Asp Asp Asp
                20              25              30

Asp Ser Asp Tyr Pro Glu Met Glu Asp Asp Asp Ala Ser
            35              40              45

Tyr Cys Thr Glu Ser Ser Phe Arg Ser His Ser Thr Tyr Ser Ser Thr
 50                  55                  60

Pro Gly Arg Arg Lys Pro Arg Val His Arg Pro Arg Ser Pro Ile Leu
 65                  70                  75                  80

Glu Glu Lys Asp Ile Pro Pro Leu Glu Phe Pro Lys Ser Ser Glu Asp
                 85                  90                  95

Leu Met Val Pro Asn Glu His Ile Met Asn Val Ile Ala Ile Tyr Glu
                100                 105                 110

Val Leu Arg Asn Phe Gly Thr Val Leu Arg Leu Ser Pro Phe Arg Phe
            115                 120                 125

Glu Asp Phe Cys Ala Ala Leu Val Ser Gln Glu Gln Cys Thr Leu Met
130                 135                 140

Ala Glu Met His Val Val Leu Leu Lys Ala Val Leu Arg Glu Glu Asp
145                 150                 155                 160

Thr Ser Asn Thr Thr Phe Gly Pro Ala Asp Leu Lys Asp Ser Val Asn
                165                 170                 175

Ser Thr Leu Tyr Phe Ile Asp Gly Met Thr Trp Pro Glu Val Leu Arg
            180                 185                 190

Val Tyr Cys Glu Ser Asp Lys Glu Tyr His His Val Leu Pro Tyr Gln
        195                 200                 205

Glu Ala Glu Asp Tyr Pro Tyr Gly Pro Val Glu Asn Lys Ile Lys Val
    210                 215                 220

Leu Gln Phe Leu Val Asp Gln Phe Leu Thr Thr Asn Ile Ala Arg Glu
225                 230                 235                 240

Glu Leu Met Ser Glu Gly Val Ile Gln Tyr Asp Asp His Cys Arg Val
                245                 250                 255

Cys His Lys Leu Gly Asp Leu Leu Cys Cys Glu Thr Cys Ser Ala Val
            260                 265                 270

Tyr His Leu Glu Cys Val Lys Pro Pro Leu Glu Val Pro Glu Asp
        275                 280                 285

Glu Trp Gln Cys Glu Val Cys Val Ala His Lys Val Pro Gly Val Thr
    290                 295                 300

Asp Cys Val Ala Glu Ile Gln Lys Asn Lys Pro Tyr Ile Arg His Glu
305                 310                 315                 320

Pro Ile Gly Tyr Asp Arg Ser Arg Arg Lys Tyr Trp Phe Leu Asn Arg
                325                 330                 335

Arg Leu Ile Ile Glu Glu Asp Thr Glu Asn Glu Asn Glu Lys Lys Ile
            340                 345                 350
```

-continued

```
Trp Tyr Tyr Ser Thr Lys Val Gln Leu Ala Glu Leu Ile Asp Cys Leu
        355                 360                 365

Asp Lys Asp Tyr Trp Glu Ala Glu Leu Cys Lys Ile Leu Glu Glu Met
        370                 375                 380

Arg Glu Glu Ile His Arg His Met Asp Ile Thr Glu Asp Leu Thr Asn
385                 390                 395                 400

Lys Ala Arg Gly Ser Asn Lys Ser Phe Leu Ala Ala Ala Asn Glu Glu
                405                 410                 415

Ile Leu Glu Ser Ile Arg Ala Lys Lys Gly Asp Ile Asp Asn Val Lys
                420                 425                 430

Ser Pro Glu Glu Thr Glu Lys Asp Lys Asn Glu Thr Glu Asn Asp Ser
                435                 440                 445

Lys Asp Ala Glu Lys Asn Arg Glu Glu Phe Glu Asp Gln Ser Leu Glu
450                 455                 460

Lys Asp Ser Asp Asp Lys Thr Pro Asp Asp Pro Glu Gln Gly Lys
465                 470                 475                 480

Ser Glu Val Gly Asp Phe Lys Ser Glu Lys Ser Asn Gly Glu Leu Ser
                485                 490                 495

Glu Ser Pro Gly Ala Gly Lys Gly Ala Ser Gly Ser Thr Arg Ile Ile
                500                 505                 510

Thr Arg Leu Arg Asn Pro Asp Ser Lys Leu Ser Gln Leu Lys Ser Gln
                515                 520                 525

Gln Val Ala Ala Ala His Glu Ala Asn Lys Leu Phe Lys Glu Gly
                530                 535                 540

Lys Glu Val Leu Val Val Asn Ser Gln Gly Glu Ile Ser Arg Leu Ser
545                 550                 555                 560

Thr Lys Lys Glu Val Ile Met Lys Gly Asn Ile Asn Asn Tyr Phe Lys
                565                 570                 575

Leu Gly Gln Glu Gly Lys Tyr Arg Val Tyr His Asn Gln Tyr Ser Thr
                580                 585                 590

Asn Ser Phe Ala Leu Asn Lys His Gln His Arg Glu Asp His Asp Lys
                595                 600                 605

Arg Arg His Leu Ala His Lys Phe Cys Leu Thr Pro Ala Gly Glu Phe
        610                 615                 620

Lys Trp Asn Gly Ser Val His Gly Ser Lys Val Leu Thr Ile Ser Thr
625                 630                 635                 640

Leu Arg Leu Thr Ile Thr Gln Leu Glu Asn Asn Ile Pro Ser Ser Phe
                645                 650                 655

Leu His Pro Asn Trp Ala Ser His Arg Ala Asn Trp Ile Lys Ala Val
                660                 665                 670

Gln Met Cys Ser Lys Pro Arg Glu Phe Ala Leu Ala Leu Ala Ile Leu
                675                 680                 685

Glu Cys Ala Val Lys Pro Val Val Met Leu Pro Ile Trp Arg Glu Phe
        690                 695                 700

Leu Gly His Thr Arg Leu His Arg Met Thr Ser Ile Glu Arg Glu Glu
705                 710                 715                 720

Lys Glu Lys Val Lys Lys Glu Lys Lys Gln Glu Glu Glu Thr
                725                 730                 735

Met Gln Gln Ala Thr Trp Val Lys Tyr Thr Phe Pro Val Lys His Gln
                740                 745                 750

Val Trp Lys Gln Lys Gly Glu Glu Tyr Arg Val Thr Gly Tyr Gly Gly
                755                 760                 765

Trp Ser Trp Ile Ser Lys Thr His Val Tyr Arg Phe Val Pro Lys Leu
```

-continued

```
            770             775             780
Pro Gly Asn Thr Asn Val Asn Tyr Arg Lys Ser Leu Glu Gly Thr Lys
785             790             795             800

Asn Asn Met Asp Glu Asn Met Asp Ser Asp Lys Arg Lys Cys Ser
            805             810             815

Arg Ser Pro Lys Lys Ile Lys Ile Glu Pro Asp Ser Glu Lys Asp Glu
            820             825             830

Val Lys Gly Ser Asp Ala Ala Lys Gly Ala Asp Gln Asn Glu Met Asp
            835             840             845

Ile Ser Lys Ile Thr Glu Lys Lys Asp Gln Asp Val Lys Glu Leu Leu
    850             855             860

Asp Ser Asp Ser Asp Lys Pro Cys Lys Glu Glu Pro Met Glu Val Asp
865             870             875             880

Asp Asp Met Lys Thr Glu Ser His Val Asn Cys Gln Glu Ser Ser Gln
            885             890             895

Val Asp Val Val Asn Val Ser Glu Gly Phe His Leu Arg Thr Ser Tyr
            900             905             910

Lys Lys Lys Thr Lys Ser Ser Lys Leu Asp Gly Leu Leu Glu Arg Arg
            915             920             925

Ile Lys Gln Phe Thr Leu Glu Glu Lys Gln Arg Leu Glu Lys Ile Lys
    930             935             940

Leu Glu Gly Gly Ile Lys Gly Ile Gly Lys Thr Ser Thr Asn Ser Ser
945             950             955             960

Lys Asn Leu Ser Glu Ser Pro Val Ile Thr Lys Ala Lys Glu Gly Cys
            965             970             975

Gln Ser Asp Ser Met Arg Gln Glu Gln Ser Pro Asn Ala Asn Asn Asp
            980             985             990

Gln Pro Glu Asp Leu Ile Gln Gly Cys Ser Gln Ser Asp Ser Ser Val
            995             1000            1005

Leu Arg Met Ser Asp Pro Ser His Thr Thr Asn Lys Leu Tyr Pro Lys
    1010            1015            1020

Asp Arg Val Leu Asp Asp Val Ser Ile Arg Ser Pro Glu Thr Lys Cys
1025            1030            1035            1040

Pro Lys Gln Asn Ser Ile Glu Asn Asp Ile Glu Glu Lys Val Ser Asp
            1045            1050            1055

Leu Ala Ser Arg Gly Gln Glu Pro Thr Lys Ser Lys Thr Lys Gly Asn
            1060            1065            1070

Asp Phe Phe Ile Asp Asp Ser Lys Leu Ala Ser Ala Asp Asp Ile Gly
            1075            1080            1085

Thr Leu Ile Cys Lys Asn Lys Lys Pro Leu Ile Gln Glu Glu Ser Asp
    1090            1095            1100

Thr Ile Val Ser Ser Ser Lys Ser Ala Leu His Ser Ser Val Pro Lys
1105            1110            1115            1120

Ser Thr Asn Asp Arg Asp Ala Thr Pro Leu Ser Arg Ala Met Asp Phe
            1125            1130            1135

Glu Gly Lys Leu Gly Cys Asp Ser Glu Ser Asn Ser Thr Leu Glu Asn
            1140            1145            1150

Ser Ser Asp Thr Val Ser Ile Gln Asp Ser Ser Glu Glu Asp Met Ile
            1155            1160            1165

Val Gln Asn Ser Asn Glu Ser Ile Ser Glu Gln Phe Arg Thr Arg Glu
    1170            1175            1180

Gln Asp Val Glu Val Leu Glu Pro Leu Lys Cys Glu Leu Val Ser Gly
1185            1190            1195            1200
```

```
Glu Ser Thr Gly Asn Cys Glu Asp Arg Leu Pro Val Lys Gly Thr Glu
                1205                1210                1215
Ala Asn Gly Lys Lys Pro Ser Gln Gln Lys Lys Leu Glu Glu Arg Pro
            1220                1225                1230
Val Asn Lys Cys Ser Asp Gln Ile Lys Leu Lys Asn Thr Thr Asp Lys
            1235                1240                1245
Lys Asn Asn Glu Asn Arg Glu Ser Glu Lys Lys Gly Gln Arg Thr Ser
        1250                1255                1260
Thr Phe Gln Ile Asn Gly Lys Asp Asn Lys Pro Lys Ile Tyr Leu Lys
1265                1270                1275                1280
Gly Glu Cys Leu Lys Glu Ile Ser Glu Ser Arg Val Val Ser Gly Asn
            1285                1290                1295
Val Glu Pro Lys Val Asn Asn Ile Asn Lys Ile Ile Pro Glu Asn Asp
            1300                1305                1310
Ile Lys Ser Leu Thr Val Lys Glu Ser Ala Ile Arg Pro Phe Ile Asn
        1315                1320                1325
Gly Asp Val Ile Met Glu Asp Phe Asn Glu Arg Asn Ser Ser Glu Thr
    1330                1335                1340
Lys Ser His Leu Leu Ser Ser Ser Asp Ala Glu Gly Asn Tyr Arg Asp
1345                1350                1355                1360
Ser Leu Glu Thr Leu Pro Ser Thr Lys Glu Ser Asp Ser Thr Gln Thr
                1365                1370                1375
Thr Thr Pro Ser Ala Ser Cys Pro Glu Ser Asn Ser Val Asn Gln Val
            1380                1385                1390
Glu Asp Met Glu Ile Glu Thr Ser Glu Val Lys Lys Val Thr Ser Ser
        1395                1400                1405
Pro Ile Thr Ser Glu Glu Ser Asn Leu Ser Asn Asp Phe Ile Asp
    1410                1415                1420
Glu Asn Gly Leu Pro Ile Asn Lys Asn Glu Asn Val Asn Gly Glu Ser
1425                1430                1435                1440
Lys Arg Lys Thr Val Ile Thr Glu Val Thr Thr Met Thr Ser Thr Val
                1445                1450                1455
Ala Thr Glu Ser Lys Thr Val Ile Lys Val Glu Lys Gly Asp Lys Gln
            1460                1465                1470
Thr Val Val Ser Ser Thr Glu Asn Cys Ala Lys Ser Thr Val Thr Thr
        1475                1480                1485
Thr Thr Thr Thr Val Thr Lys Leu Ser Thr Pro Ser Thr Gly Gly Ser
    1490                1495                1500
Val Asp Ile Ile Ser Val Lys Glu Gln Ser Lys Thr Val Val Thr Thr
1505                1510                1515                1520
Thr Val Thr Asp Ser Leu Thr Thr Thr Gly Thr Leu Val Thr Ser
                1525                1530                1535
Met Thr Val Ser Lys Glu Tyr Ser Thr Arg Asp Lys Val Lys Leu Met
            1540                1545                1550
Lys Phe Ser Arg Pro Lys Lys Thr Arg Ser Gly Thr Ala Leu Pro Ser
        1555                1560                1565
Tyr Arg Lys Phe Val Thr Lys Ser Thr Lys Ser Ile Phe Val Leu
    1570                1575                1580
Pro Asn Asp Asp Leu Lys Lys Leu Ala Arg Lys Gly Gly Ile Arg Glu
1585                1590                1595                1600
Val Pro Tyr Phe Asn Tyr Asn Ala Lys Pro Ala Leu Asp Ile Trp Pro
            1605                1610                1615
```

-continued

```
Tyr Pro Ser Pro Arg Pro Thr Phe Gly Ile Thr Trp Arg Tyr Arg Leu
            1620                1625                1630

Gln Thr Val Lys Ser Leu Ala Gly Val Ser Leu Met Leu Arg Leu Leu
            1635                1640                1645

Trp Ala Ser Leu Arg Trp Asp Asp Met Ala Ala Lys Val Pro Pro Gly
            1650                1655                1660

Gly Gly Ser Thr Arg Thr Glu Thr Ser Glu Thr Glu Ile Thr Thr Thr
1665                1670                1675                1680

Glu Ile Ile Lys Arg Arg Asp Val Gly Pro Tyr Gly Ile Arg Phe Glu
            1685                1690                1695

Tyr Cys Ile Arg Lys Ile Ile Cys Pro Ile Gly Val Pro Glu Thr Pro
            1700                1705                1710

Lys Glu Thr Pro Thr Pro Gln Arg Lys Gly Leu Arg Ser Ser Ala Leu
            1715                1720                1725

Arg Pro Lys Arg Pro Glu Thr Pro Lys Gln Thr Gly Pro Val Ile Ile
            1730                1735                1740

Glu Thr Trp Val Ala Glu Glu Leu Glu Leu Trp Glu Ile Arg Ala
1745                1750                1755                1760

Phe Ala Glu Arg Val Glu Lys Glu Lys Ala Gln Ala Val Glu Gln Gln
            1765                1770                1775

Ala Lys Lys Arg Leu Glu Gln Gln Lys Pro Thr Val Ile Ala Thr Ser
            1780                1785                1790

Thr Thr Ser Pro Thr Ser Ser Thr Thr Ser Thr Ile Ser Pro Ala Gln
            1795                1800                1805

Lys Val Met Val Ala Pro Ile Ser Gly Ser Val Thr Thr Gly Thr Lys
            1810                1815                1820

Met Val Leu Thr Thr Lys Val Gly Ser Pro Ala Thr Val Thr Phe Gln
1825                1830                1835                1840

Gln Asn Lys Asn Phe His Gln Thr Phe Ala Thr Trp Val Lys Gln Gly
            1845                1850                1855

Gln Ser Asn Ser Gly Val Val Gln Val Gln Gln Lys Val Leu Gly Ile
            1860                1865                1870

Ile Pro Ser Ser Thr Gly Thr Ser Gln Gln Thr Phe Thr Ser Phe Gln
            1875                1880                1885

Pro Arg Thr Ala Thr Val Thr Ile Arg Pro Asn Thr Ser Gly Ser Gly
            1890                1895                1900

Gly Thr Thr Ser Asn Ser Gln Val Ile Thr Gly Pro Gln Ile Arg Pro
1905                1910                1915                1920

Gly Met Thr Val Ile Arg Thr Pro Leu Gln Gln Ser Thr Leu Gly Lys
            1925                1930                1935

Ala Ile Ile Arg Thr Pro Val Met Val Gln Pro Gly Ala Pro Gln Gln
            1940                1945                1950

Val Met Thr Gln Ile Ile Arg Gly Gln Pro Val Ser Thr Ala Val Ser
            1955                1960                1965

Ala Pro Asn Thr Val Ser Ser Thr Pro Gly Gln Lys Ser Leu Thr Ser
            1970                1975                1980

Ala Thr Ser Thr Ser Asn Ile Gln Ser Ser Ala Ser Gln Pro Pro Arg
1985                1990                1995                2000

Pro Gln Gln Gly Gln Val Lys Leu Thr Met Ala Gln Leu Thr Gln Leu
            2005                2010                2015

Thr Gln Gly His Gly Gly Asn Gln Gly Leu Thr Val Val Ile Gln Gly
            2020                2025                2030

Gln Gly Gln Thr Thr Gly Gln Leu Gln Leu Ile Pro Gln Gly Val Thr
```

-continued

```
                    2035                2040                2045
Val Leu Pro Gly Pro Gly Gln Gln Leu Met Gln Ala Ala Met Pro Asn
    2050                2055                2060

Gly Thr Val Gln Arg Phe Leu Phe Thr Pro Leu Ala Thr Thr Ala Thr
2065                2070                2075                2080

Thr Ala Ser Thr Thr Thr Thr Thr Val Ser Thr Thr Ala Ala Gly Thr
                2085                2090                2095

Gly Glu Gln Arg Gln Ser Lys Leu Ser Pro Gln Met Gln Val His Gln
            2100                2105                2110

Asp Lys Thr Leu Pro Pro Ala Gln Ser Ser Val Gly Pro Ala Lys
        2115                2120                2125

Ala Gln Pro Gln Thr Ala Gln Pro Ser Ala Arg Pro Gln Pro Gln Thr
    2130                2135                2140

Gln Pro Gln Ser Pro Ala Gln Pro Glu Val Gln Thr Gln Pro Glu Val
2145                2150                2155                2160

Gln Thr Gln Thr Thr Val Ser Ser His Val Pro Ser Glu Ala Gln Pro
                2165                2170                2175

Thr His Ala Gln Ser Ser Lys Pro Gln Val Ala Ala Gln Ser Gln Pro
            2180                2185                2190

Gln Ser Asn Val Gln Gly Gln Ser Pro Val Arg Val Gln Ser Pro Ser
        2195                2200                2205

Gln Thr Arg Ile Arg Pro Ser Thr Pro Ser Gln Leu Ser Pro Gly Gln
    2210                2215                2220

Gln Ser Gln Val Gln Thr Thr Thr Ser Gln Pro Ile Pro Ile Gln Pro
2225                2230                2235                2240

His Thr Ser Leu Gln Ile Pro Ser Gln Gly Gln Pro Gln Ser Gln Pro
                2245                2250                2255

Gln Val Gln Ser Ser Thr Gln Thr Leu Ser Ser Gly Gln Thr Leu Asn
            2260                2265                2270

Gln Val Ser Val Ser Ser Pro Ser Arg Pro Gln Leu Gln Ile Gln Gln
        2275                2280                2285

Pro Gln Pro Gln Val Ile Ala Val Pro Gln Leu Gln Gln Gln Val Gln
    2290                2295                2300

Val Leu Ser Gln Ile Gln Ser Gln Val Val Ala Gln Ile Gln Ala Gln
2305                2310                2315                2320

Gln Ser Gly Val Pro Gln Gln Ile Lys Leu Gln Leu Pro Ile Gln Ile
                2325                2330                2335

Gln Gln Ser Ser Ala Val Gln Thr His Gln Ile Gln Asn Val Val Thr
            2340                2345                2350

Val Gln Ala Ala Ser Val Gln Glu Gln Leu Gln Arg Val Gln Gln Leu
        2355                2360                2365

Arg Asp Gln Gln Gln Lys Lys Lys Gln Gln Gln Ile Glu Ile Lys Arg
    2370                2375                2380

Glu His Thr Leu Gln Ala Ser Asn Gln Ser Glu Ile Ile Gln Lys Gln
2385                2390                2395                2400

Val Val Met Lys His Asn Ala Val Ile Glu His Leu Lys Gln Lys Lys
                2405                2410                2415

Ser Met Thr Pro Ala Glu Arg Glu Glu Asn Gln Arg Met Ile Val Cys
            2420                2425                2430

Asn Gln Val Met Lys Tyr Ile Leu Asp Lys Ile Asp Lys Glu Glu Lys
        2435                2440                2445

Gln Ala Ala Lys Lys Arg Lys Arg Glu Glu Ser Val Glu Gln Lys Arg
    2450                2455                2460
```

-continued

```
Ser Lys Gln Asn Ala Thr Lys Leu Ser Ala Leu Leu Phe Lys His Lys
2465                2470                2475                2480

Glu Gln Leu Arg Ala Glu Ile Leu Lys Lys Arg Ala Leu Leu Asp Lys
                2485                2490                2495

Asp Leu Gln Ile Glu Val Gln Glu Leu Lys Arg Asp Leu Lys Ile
            2500                2505                2510

Lys Lys Glu Lys Asp Leu Met Gln Leu Ala Gln Ala Thr Ala Val Ala
            2515                2520                2525

Ala Pro Cys Pro Pro Val Thr Pro Val Leu Pro Ala Pro Pro Ala Pro
        2530                2535                2540

Pro Pro Ser Pro Pro Pro Pro Gly Val Gln His Thr Gly Leu Leu
2545                2550                2555                2560

Ser Thr Pro Thr Leu Pro Val Ala Ser Gln Lys Arg Lys Arg Glu Glu
                2565                2570                2575

Glu Lys Asp Ser Ser Ser Lys Ser Lys Lys Lys Lys Met Ile Ser Thr
            2580                2585                2590

Thr Ser Lys Glu Thr Lys Lys Asp Thr Lys Leu Tyr Cys Ile Cys Lys
            2595                2600                2605

Thr Pro Tyr Asp Glu Ser Lys Phe Tyr Ile Gly Cys Asp Arg Cys Gln
    2610                2615                2620

Asn Trp Tyr His Gly Arg Cys Val Gly Ile Leu Gln Ser Glu Ala Glu
2625                2630                2635                2640

Leu Ile Asp Glu Tyr Val Cys Pro Gln Cys Gln Ser Thr Glu Asp Ala
            2645                2650                2655

Met Thr Val Leu Thr Pro Leu Thr Glu Lys Asp Tyr Glu Gly Leu Lys
            2660                2665                2670

Arg Val Leu Arg Ser Leu Gln Ala His Lys Met Ala Trp Pro Phe Leu
            2675                2680                2685

Glu Pro Val Asp Pro Asn Asp Ala Pro Asp Tyr Tyr Gly Val Ile Lys
2690                2695                2700

Glu Pro Met Asp Leu Ala Thr Met Glu Glu Arg Val Gln Arg Arg Tyr
2705                2710                2715                2720

Tyr Glu Lys Leu Thr Glu Phe Val Ala Asp Met Thr Lys Ile Phe Asp
            2725                2730                2735

Asn Cys Arg Tyr Tyr Asn Pro Ser Asp Ser Pro Phe Tyr Gln Cys Ala
            2740                2745                2750

Glu Val Leu Glu Ser Phe Phe Val Gln Lys Leu Lys Gly Phe Lys Ala
            2755                2760                2765

Ser Arg Ser His Asn Asn Lys Leu Gln Ser Thr Ala Ser
    2770                2775                2780
```

TRANSCRIPTIONAL REGULATORY FACTOR

This application is a divisional application of U.S. patent application Ser. No. 09/698,295, filed on Oct. 27, 2000, now U.S. Pat. No. 6,689,584 which is a continuation-in-part of PCT/JP99/02340, filed Apr. 30, 1999, and claims priority from Japanese Patent Application No. 10/137,631, filed Apr. 30, 1998.

TECHNICAL FIELD

This invention relates to a novel transcriptional regulatory factor comprising bromodomains and the encoding gene.

BACKGROUND OF THE INVENTION

The bromodomain is a characteristic amino-acid motif seen in transcriptional regulatory factors and is believed to be involved in the interactions with other transcriptional regulatory factors. Proteins comprising the bromodomain, normally have one or two (Tamkun et al. (1992) Nuc. Acids Res. 20:2603; Haynes et al. (1992) Nuc. Acids Res. 20: 2603), but as many as five (Nicolas et al. (1996) Gene 175(12):233–240) bromodomain motifs. This motif has been identified in a wide range of animals, for example, in the homeotic gene (Digan et al. (1986) Dev. Biol. 114: 161–169; Tamkun et al. (1992) Cell 68: 561–572) of the fruit fly (Drosophila), in the transcriptional regulatory genes of yeasts (Winston et al. (1987) Genetics 115:649–656; Laurent et al. (1991) Proc. Nat. Acad. Sci. USA 88:2687–2691) and in mammals (Denis et al. (1996) Genes and Devel. 10:261–271; Yang et al. (1996) Nature 382:319–324). According to a recent report (Jeanmougin et al. (1997) Trends Biochem. Sci. 22:151–153), 37 bromodomain genes, including 13 human genes are recorded in the database. In addition to the bromodomain motif of amino acid residues 59–63, the sequences adjacent to the motif are also structurally conserved, and furthermore, 4 α-helixes (Z, A, B, and C) are reported to be coded within the long 110 amino acids.

When these bromodomain-comprising transcriptional regulatory factors are compared, they all regulate signal-dependent transcription in actively proliferating cells (Tamkun et al. (1992) Cell 68:561–572; Haynes et al. (1992) Nuc. Acids Res. 20:2603). This characteristic implies that oncogenesis may occur when a gene encoding a bromodomain-containing protein undergoes abnormal regulation. In reality, six bromodomain genes have been experimentally proven to associate with oncogenesis. Three of these genes HRX/ALL-1 (Tkachuk et al. (1992) Cell 71:691–700; Gu et al. (1992) Cell 71:701–708); TIF1 (Miki et al. (1991) Proc. Nat. Acad. Sci. USA 88:5167–5171; Le Douarin et al. (1995) EMBO J. 14:2020–2033) and CBP (Borrow et al. (1996) Nature Genet. 14:33–41) are linked with the gene cleavage points in leukemia. All three of these proteins contain the C4HC3 (also called PHD/LAP/TRX) zinc-finger (Aasland et al. (1995) Trends Biochem. Sci. 20:56–59; Koken et al. (1995) CR Acad. Sci. III, 318:733–739; Saha et al. (1995) Proc. Nat. Acad. Sci. USA 92:9737–9741). Also, there are findings that CBP/P300 interact with p53 (Gu et al. (1997) Nature 387:819–823; Lill et al.(1997) Nature 387: 823–827) and other various transcriptional factors, suggesting that CBP and the homologous gene P300 play a key-role in cancer.

The other three genes have been suggested to be linked with cancer in various ways. BRG1 interacts with retinoblastoma protein RB (Dunaief et al. (1994) Cell 79:119–130), inducing formation of flat, growth-arrested cells, and thereby showing a tumor-suppressive activity. RING3 has a homology with the fruit fly (Drosophila) growth control protein fsh (Haynes et al. (1989) Dev. Biol. 134:246–257) and is a serine-threonine kinase having endonuclear autophosphorylation activity. This activity has been reported to be linked to the growth phase of chronic and acute lymphocytic leukemia (Denis et al. (1996) Genes and Devel. 10:261–271). As for P/CAF, it has been reported to inhibit the interaction between E1A and p300/CBP (Yang et al. (1996) Nature 382:319–324). When P/CAF is exogenously expressed on HeLa cells, the cell cycle is inhibited. This is believed to be due to the disruption of the transcriptional regulation of E1A by the binding of P/CAF to p300/CBP. Similar to p300/CBP (Bannister and Kouzarides (1996) Nature 384:641–643), P/CAF has been reported to contain histone acetyl-transferase activity (Yang et al. (1996) Nature 382:319–324).

Thus, regulatory abnormalities of transcriptional regulatory factors comprising bromodomains are envisaged to be closely associated with various diseases, particularly, cancer and other cell-proliferation-linked diseases. Hence, attention has been focused on transcriptional regulatory factors comprising bromodomains in the recent years as novel targets for the treatment of cancer and other cell-proliferation-linked diseases.

SUMMARY OF THE INVENTION

The present invention provides a novel transcriptional regulatory factor comprising bromodomains, the encoding gene, a method of production, and a screening method for a drug-candidate compound that utilizes the protein and the gene of the present invention.

In order to solve the above-mentioned problems, EST databases were BLAST searched using various nucleotide sequences encoding known bromodomain motifs. As a result, several potential bromodomain-gene-encoding ESTs were found by the search using nucleotide sequence of Tetrahymena thermophila HAT A1 gene. One of these ESTs, the fetal lung cDNA library-derived EST (W17142) was found to encode an unknown gene. Therefore, isolation of full-length cDNA of EST W17142 was initiated. Specifically, primers were designed based on the EST W17142 sequence, and an amplification product was obtained by the polymerase chain reaction using testicular cDNA as the template. Then, the testicular cDNA library was screened using this amplification product as the probe, and a re-screening of the library was done using the cDNA clone comprising the above-mentioned EST sequence, thereby successfully isolating a full-length cDNA corresponding to EST W17142. By structural analysis of the protein encoded by the isolated cDNA, the present Inventors found that apart from the bromodomain, said protein had several regions and domains conserved in transcriptional regulatory factors.

Also, they found that the protein encoded by the isolated cDNA interacts with hSNF2H and hSNF2L that are implicated in the series of processes related to the chromatin-mediated transcriptional regulatory mechanism, and also with the transcription co-activator NcoA-62/Skip, which interacts with the ligand-binding domains of various nuclear receptors (VDR, RAR) and the Ski viral oncoprotein.

The transcriptional regulatory factor and the encoding gene revealed by the Inventors can be utilized for the screening of compounds inhibiting the binding between said transcriptional regulatory factor and an interacting factor, and compounds which regulate the binding activity. The compounds thus isolated are expected to be applied as pharmaceuticals.

Namely, the present invention relates to a novel transcriptional regulatory factor comprising a bromodomain and the encoding gene, as well as methods of production, and a screening method for related-factors and drug-candidate compounds that utilize the protein and the gene of the present invention. Specifically, the present invention relates to:

1. a protein comprising the amino acid sequence of SEQ ID NO:1 or 10;

2. a transcriptional regulatory factor comprising a bromodomain and the amino acid sequence of SEQ ID NO:1 or 10, wherein one or more amino acids are replaced, deleted, added, and/or inserted;

3. a protein comprising the amino acid sequence of SEQ ID NO:1 or 10, wherein one or more amino acids are replaced, deleted, added, and/or inserted, and having an activity to bind to a protein selected from the group consisting of hSNF2H, hSNF2L, NCoA-62/Skip and homologues thereof;

4. a transcriptional regulatory factor comprising a bromodomain, and encoded by a DNA hybridizing with the DNA comprising the nucleotide sequence of SEQ ID NO:2 or 9;

5. a transcriptional regulatory factor encoded by a DNA hybridizing with the DNA comprising the nucleotide sequence of SEQ ID NO:2 or 9, and having an activity to bind to a protein selected from the group consisting of hSNF2H, hSNF2L, NCoA-62/Skip and homologues thereof;

6. a DNA encoding the transcriptional regulatory factor of any one of (1) to (5);

7. the DNA of (6), which contains the coding region of the nucleotide sequence of SEQ ID NO:2 or 9;

8. a vector containing the DNA of (6) or (7);

9. a transformant carrying, in an expressible manner, the DNA of (6) or (7);

10. a method for producing the transcriptional regulatory factor of any one of (1) to (5), the method comprising culturing the transformant of (9);

11. an antibody which binds to the transcriptional regulatory factor of any one of (1) to (5);

12. a method for screening a compound having an activity to bind to the transcriptional regulatory factor of any one of (1) to (5), the method comprising the steps of, (a) exposing a test sample to said transcriptional regulatory factor, (b) detecting the binding activity between the test sample and said transcriptional regulatory factor, and, (c) selecting a compound having the binding activity to said transcriptional regulatory factor;

13. a method for screening a compound which promotes or inhibits the binding between the transcriptional regulatory factor of any one of (1) to (5) and a protein selected from the group consisting of hSNF2H, hSNF2L, NCoA-62/Skip and homologues thereof, the method comprising the steps of, (a) exposing the transcriptional regulatory factor to hSNF2H, hSNF2L, NCoA-62/Skip or homologues thereof, in the presence of the test sample, (b) detecting the binding activity between said transcriptional regulatory factor and hSNF2H, hSNF2L, NCoA-62/Skip or homologues thereof, (c) selecting a compound which increases or decreases said binding activity when compared with the binding activity in the absence of the test sample (control);

14. a compound which is obtainable by the method of (13), which inhibits the binding between the transcriptional regulatory factor of any one of (1) to (5) and a protein selected from the group consisting of hSNF2H, hSNF2L, NCoA-62/Skip and homologues thereof; and 15. a DNA comprising at least 15 nucleotides, which can specifically hybridize with the DNA comprising the nucleotide sequence of SEQ ID NO:2 or 9. The DNA can also be at least 351, 400, 450, 500, 700, 1000, 2200, 2500, or 3000 bp in length.

Herein, "transcriptional regulatory factor" indicates a protein that regulates gene expression. "Bromodomain" means, an amino acid motif associated with protein-protein interactions conserved within transcriptional regulatory factors linked to signal-dependent transcription.

The present invention relates to a transcriptional regulatory factor comprising a bromodomain. The amino acid sequences of the protein named "TCoA1" included in the present invention, and its variant are shown in SEQ ID NO:1 and SEQ ID NO:10, respectively, and the nucleotide sequences of their cDNA in SEQ ID NO:2 and SEQ ID NO:9, respectively (unless otherwise noted, these will be grouped as "TCoA1", hereafter). "TCoA1" is most deeply associated with the presumed proteins of nematode (*C. elegans*) chromosome III genes F26H11.2, F26H11.3a and F26H11.3b (Wilson et al. (1994) Nature 368:32–38), the function of which are unknown and which were identified by the genomic sequence of one cosmid F26H11. When the amino acid sequence of these two proteins—the presumed nematode protein and the "TCoA1" protein—are compared, although the domain configurations are different, they are extremely alike.

Like many bromodomain proteins, "TCoA1" has one bromodomain. Being structurally similar to the TIF family, GCN5 and P/CAF, this bromodomain is situated close to the carboxyl-terminus (Jeanmougin et al. (1997) Trends Biochem. Sci. 22:151–153). Like other bromodomain proteins, "TCoA1" has a C4HC3 zinc-finger. The combination of the bromodomain and the zinc-finger has been discovered frequently in the gene cleavage points in several leukemia, so far (Tkachuk et al. (1992) Cell 71:691–700; Gu et al. (1992) Cell 71: 701–708; Miki et al. (1991) Proc. Nat. Acad. Sci. USA 88:5167–5171; Le Douarin et al. (1995) EMBO J. 14:2020–2033; Borrow et al. (1996) Nature Genet. 14:33–41). Therefore, "TCoA1" is a candidate cleavage gene associated with chromosome no. 17 q23.

"TCoA1" has numerous nuclear transport signal motifs. This indicates that "TCoA1" protein is located within the nucleus. Like other bromodomain proteins, "TCoA1" has a LXXLL motif series that likely determines the site of interaction with nuclear receptors (Heery et al. (1997) Trends Biochem. Sci. 22:151–153; Torchia et al. (1997) Nature 387:677–684). The possibility that it interacts with the receptor bound to a ligand via the LXXLL domain indicates that "TCoA1" functions as a transcriptional co-activator. In the carboxyl terminus of "TCoA1", a glutamine-rich domain is located spanning a very large region. Glutamine-rich domains have been identified in many transcriptional regulatory factors including bromodomain-containing proteins like p300/CBP (Shikama et al. (1997) Trends in Cell Biol. 2:230–236) and fsh protein of fruit fly (*Drosophila*) (Haynes et al. (1989) Dev. Biol. 134:246–257). These acidic regions have been predicted to be associated with the protein-protein interactions that determine the function as an active substance (Courey et al. (1989) Cell 59:827–836). "TCoA1" protein has many common characteristics with other bromodomain proteins known to be linked to cell-proliferation-linked diseases such as cancer. Therefore, "TCoA1" protein may also be linked to cancer, and thus, the "TCoA1" protein and its gene, a compound that regulate the function of the "TCoA1" protein can be applied for the prevention and treatment of cancer and other cell-proliferation-linked diseases.

Moreover, the fact that hSNF2H and hSNF2L, which interact with "TCoA1", are involved in the series of processes related to the chromatin-mediated transcriptional regulatory mechanism, strongly indicates that "TCoA1" is playing some sort of a role in chromatin-mediated transcriptional regulation. Therefore, it can be conceived that "TCoA1" is playing a major role as a protein that integrates transcriptional responses towards nuclear receptors by associating with the chromatin reconstruction mechanism.

The transcriptional regulatory factor of the present invention can be prepared by methods known to one skilled in the art, as a recombinant protein made using genetic engineering techniques, and also as a natural protein. For example, a recombinant protein can be prepared by inserting DNA encoding the protein of the present invention (for example, DNA comprising the nucleotide sequence of SEQ ID NO:2 or 9) into a suitable expression vector, introducing this into a host cell, and purifying the protein from the resulting transformant. The natural protein can be acquired by preparing a column coupled with an antibody obtained by immunizing a small animal with the recombinant protein, and performing affinity chromatography for extracts of tissues or cells (for example, testis, tumor cells, etc.) expressing high levels of the transcriptional regulatory factor of the present invention.

Also, this invention features a transcriptional regulatory factor, which is functionally equivalent to the "TCoA1" protein (SEQ ID NO:1 or 10). This transcriptional regulatory factor includes, mutants of the "TCoA1" protein (SEQ ID NO:1 or 10) and "TCoA1" proteins obtained from various living organisms.

To isolate a protein functionally equivalent to a certain protein, the method of inserting a mutation into the amino acids within the protein is well known to one skilled in the art. In other words, for a person skilled in the art, the isolation of a transcriptional regulatory factor functionally equivalent to the "TCoA1" protein, is a standard procedure which can be done using, for example, the PCR-mediated, site-directed-mutation-induction system (GIBCO-BRL, Gaithersburg, Md.), oligonucleotide-mediated, sight-directed-mutagenesis (Kramer et al. (1987) Methods in Enzymol. 154:350–367) suitably replacing amino acids that do not influence the function of the "TCoA1" protein set forth in SEQ ID NO:1 or 10. Mutations of amino acids can occur spontaneously as well. The transcriptional regulatory factor of the invention includes those comprising the amino acid sequence of "TCoA1" protein in SEQ ID NO:1 or 10 in which one or more amino acids have been replaced, deleted, added, and/or inserted, and have a binding-activity with hSNF2H, hSNF2L and NcoA-62/Skip, and those comprising the amino acid sequence of "TCoA 1" protein in SEQ ID NO:1 or 10 in which one or more amino acids have been replaced, deleted, added, and/or inserted, and comprise a bromodomain.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The number of amino acids that are mutated is not particularly restricted, as long as the function of the "TCoA1" protein is maintained. Normally, it is within 50 amino acids, preferably within 30 amino acids, more preferably within 10 amino acids and even more preferably within 3 amino acids. The site of mutation may be any site, as long as the function of the "TCoA1" protein is maintained.

Proteins having amino acid sequences modified by deleting, adding and/or replacing one or more amino acid residues of a certain amino acid sequence, have been known to retain the original biological activity (Mark et al., Proc. Natl. Acad. Sci. USA (1984) 81:5662–5666; Zoller et al. Nucleic Acids Research (1982) 10:6487–6500; Wang et al., Science 224:1431–1433; Dalbadie-McFarland et al., Proc. Natl. Acad. Sci. USA (1982) 79:6409–6413).

As for the amino acid residue to be mutated, it is preferable to be mutated into a different amino acid in which the properties of the amino acid side-chain are conserved. Examples of properties of amino acid side chains are, hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). (The parenthetic letters indicate the one-letter codes of amino acids). A "conservative amino acid substitution is a replacement of one amino acid belonging to one of the above groups with another amino acid in the same group.

In the present invention, the protein having several deletions in the amino acid sequence of the "TCoA1" protein (SEQ ID NO:1 or 10) includes a partial peptide comprising binding-activity with hSNF2H, hSNF2L, NcoA-62/Skip or homologues thereof. As described in Example 6 (FIG. 5), the N-terminus of the "TCoA1" protein has a binding-activity with hSNF2H, hSNF2L, NcoA-62/Skip or homologues thereof. Peptides such as these, inhibit the binding between "TCoA1" protein and the above binding-proteins in vivo, and thus can be used to inhibit the functions of the "TCoA1" protein in vivo.

A fusion protein including the "TCoA1" protein can be given as an example of a protein into which several amino acid residues have been added to the amino acid sequence of the "TCoA1" protein (SEQ ID NO:1 or 10). Fusion proteins are, fusions of the "TCoA1" protein and other peptides or proteins, and are included in the present invention. Fusion proteins can be made by techniques well known to a person skilled in the art, such as by linking the DNA encoding the "TCoA1" protein of the invention with DNA encoding other peptides or proteins, so as the frames match, inserting this into an expression vector and expressing it in a host. There is no restriction as to the peptides or proteins fused to the protein of the present invention.

Known peptides, for example, FLAG (Hopp et al., Biotechnology (1988) 6:1204–1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and such, can be used as peptides that are fused to the protein of the present invention. Examples of proteins that are fused to protein of the invention are, GST (glutathione-S-transferase), Influenza agglutinin (HA), immunoglobulin constant region, β-galactosidase, MBP (maltose-binding protein), and such.

Fusion proteins can be prepared by fusing commercially available DNA encoding these peptides or proteins with the DNA encoding the protein of the present invention and expressing the fused DNA prepared.

The hybridization technique (Sambrook et al., Molecular Cloning 2$^{nd}$ ed. 9.47–9.58, Cold Spring Harbor Lab. press, 1989) is well known to one skilled in the art as an alternative method for isolating a protein functionally equivalent to a certain protein. In other words, for a person skilled in the art, it is a general procedure to obtain a transcriptional regulatory factor functionally equivalent to the "TCoA1" protein, by isolating DNA having a high homology with the whole or part of the DNA encoding the "TCoA1" protein of SEQ ID NO:2 using the hybridization technique. The transcriptional regulatory factor of the present invention, includes transcriptional regulatory factors comprising bromodomains which are encoded by the DNA hybridizing with the DNA encoding "TCoA1" protein of SEQ ID NO:2. Animals which can be used to isolate a functionally equivalent transcriptional regulatory factor are, apart from humans, for example, mice, rats, cattle, monkeys and pigs, but there are no restrictions to the animal used. The stringency of hybridization is defined as equilibrium hybridization under the following conditions: 42° C., 2×SSC, 0.1% SDS (low stringency); 50° C., 2×SSC, 0.1% SDS (medium stringency); and 65° C., 2×SSC, 0.1% SDS (high stringency). If washings are necessary to achieve equilibrium, the washings are performed with the hybridization solution for the particular stringency desired. In general, the higher the temperature, the higher is the homology between two strands hybridizing at equilibrium. However, several factors other than temperature can influence the stringency of hybridization and one skilled in the art can suitably select the factors to accomplish a similar stringency.

In place of hybridization, the gene amplification method using a primer synthesized based on the sequence information of the DNA sequence of SEQ ID NO:9 encoding the "TCoA1" protein, for example, the polymerase chain reaction (PCR) method can be utilized to isolate a DNA encoding a transcriptional regulatory factor functionally equivalent to the "TCoA1" protein.

Proteins encoded by the DNA isolated through the above hybridization technique or gene amplification techniques, normally have a high homology to the amino acid sequence of the "TCoA1" protein. "High homology" refers to, normally a homology of 40% or higher, preferably 60% or higher, more preferably 80% or higher, even more preferably 95% or higher with the amino acid sequence of the "TCoA1" protein. The homology of a protein can be determined by following the algorithm in "Wilbur, W. J. and Lipman, D. J. Proc. Natl. Acad. Sci. USA (1983) 80, 726–730".

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See www.ncbi.nlm.nih.gov.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

Transcriptional regulatory factors functionally equivalent to the "TCoA 1" protein (SEQ ID NO:1 or 10) isolated by the above hybridization technique or gene amplification techniques include, those having a binding activity with hSNF2H, hSNF2L and NcoA-62/Skip, and a high homology in the primary structure with the "TCoA1" protein (SEQ ID NO:1 or 10), and those having the bromodomain, which is a motif thought to be vital to the function linked with cancer, and a high homology in the primary structure with the "TCoA1" protein (SEQ ID NO:10).

Other than the bromodomain, these transcriptional regulatory factors also comprise sequences involved in the interactions with other proteins (for example, leucine-zipper, LXXLL motif), sequences involved in the binding with DNA (for example, zinc-finger), and nuclear transport signals.

The existence of the bromodomain within a protein can be determined by searching the bromodomain motif PROSITE database on DNASIS (Hitachi Software Engineering).

This invention also relates to a DNA encoding the above transcriptional regulatory factor. There is no restriction as to the DNA of the present invention as long as it encodes the transcriptional regulatory factor of the invention, and includes cDNA, genomic DNA and chemically synthesized DNA. Also as long as they can encode the protein of the invention, DNAs comprising arbitrary sequences based on the degeneracy of the genetic code are also included. cDNA encoding the protein of the invention can be prepared, for example, by preparing a primer based on nucleotide information (for example, SEQ ID NO:9) of DNA encoding the transcriptional regulatory factor of the invention and performing plaque PCR (for example please refer, Affara N A et al. (1994) Genomics 22:205–210). In the case of genomic DNA, preparation can be done for example, by the method using commercially available "Qiagen genomic DNA kits" (Qiagen, Hilden, Germany). The nucleotide sequence of the DNA acquired can be decided by ordinary methods in the art by using, for example, the commercially available "dye terminator sequencing kit" (Applied Biosystems). The DNA of the present invention, as stated later, can be utilized for the production of a recombinant protein and gene therapy.

The present invention also features a vector into which the DNA of the present invention has been inserted. There is no restriction as to the vector to which DNA is inserted, and various vectors such as those for expressing the transcriptional regulatory factor of the present invention in vivo and those for preparing the recombinant protein can be used according to the objective. To express the transcriptional regulatory factor of the present invention in vivo (especially for gene therapy), various viral vectors and non-viral vectors can be used. Examples of viral vectors are, adenovirus vectors (pAdexLcw) and retrovirus vectors (pZIPneo), etc. Cationic liposomes can be given as examples of non-viral vectors. Expression vectors are especially useful when using for the purpose of producing the transcriptional regulatory factor of the invention. For example, when using colibacili (E. coli) the "pREP4" (Qiagen, Hilden, Germany) and such vectors, when using yeast "SP-Q01" (Stratagene, La Jolla, Calif.) and such, when using insect cells "Bac-to-Bac baculovirus expression system" (GIBCO-BRL, Gaithersburg, Md.) are highly appropriate, but there is no restriction. Also, when using mammalian cells such as CHO cells, COS cells, NIH3T3 cells, for example, the "LacSwitch II expression system (Stratagene, La Jolla, Calif.) is highly suitable, but there is no restriction. Insertion of the DNA of the present invention into a vector can be done using ordinary methods in the art.

The present invention also refers to a transformant, carrying, in an expressible manner, the DNA of the present invention. The transformant of the present invention includes, those carrying the above-mentioned vector into which DNA of the present invention has been inserted, and those having host genomes into which the DNA of the present invention has been integrated. As long as the DNA of the present invention is maintained in an expressible manner, no distinction is made as to the form of existence of the transformants. There is no particular restriction as to the cells into which the vector is inserted. For example, when using for the purpose of gene therapy, various cells can be used as target cells according to the type of disease. Also, when the purpose is to produce the transcriptional regulatory factor of the present invention, for example, E. coli, yeast, animal cells and insect cells can be used as hosts. Introduction of a vector into a cell can be done using known methods such as electroporation and calcium phosphate method.

Common methods applied in the art may be used to isolate and purify said recombinant protein from the transformant made for the production of recombinant proteins. For example, after collecting the transformant and obtaining the extracts, the objective protein can be purified and prepared by, ion exchange chromatography, reverse phase chromatography, gel filtration, or affinity chromatography where an antibody against the protein of the present invention has been immobilized in the column, or by combining several of these columns.

Also when the protein of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column. After purifying the fusion protein, it is also possible to exclude regions other than the objective protein by cutting with thrombin or factor-Xa as required.

The present invention also features an antibody binding to the transcriptional regulatory factor of the invention. There is no particular restriction as to the form of the antibody of the present invention and include, apart from polyclonal antibodies, monoclonal antibodies as well. The antiserum obtained by immunizing animals such as rabbits with the transcriptional regulatory factor of the present invention, polyclonal and monoclonal antibodies of all classes, humanized antibodies made by genetic engineering, human antibodies, are also included. The antibodies of the present invention can be prepared by the following methods. Polyclonal antibodies can be made by, obtaining the serum of small animals such as rabbits immunized with the transcriptional regulatory factor of the present invention, attaining a fraction recognizing only the transcriptional regulatory factor of the invention by an affinity column coupled with the protein of the present invention, and purifying immunoglobulin G or M from this fraction by a protein G or protein A column. Monoclonal antibodies can be made by immunizing small animals such as mice with the transcriptional regulatory factor of the present invention, excising the spleen from the animal, homogenizing the organ into cells, fusing the cells with mouse myeloma cells using a reagent such as polyethylene glycol, selecting clones that produce antibodies against the transcriptional regulatory factor of the invention from the fused cells (hybridomas), transplanting the obtained hybridomas into the abdominal cavity of a mouse, and extracting ascites. The obtained monoclonal antibodies can be purified by, for example, ammonium sulfate precipitation, protein A or protein G column, DEAE ion exchange chromatography, or an affinity column to which the transcriptional regulatory factor of the present invention is coupled. The antibody of the invention can be used for purifying and detecting the transcriptional regulatory factor of the invention. It can also be used as a pharmaceutical drug to inhibit the function of the present transcriptional regulatory factor. When using the antibody as a drug, in the view-point of immunogenicity, human antibodies or humanized antibodies are effective. The human antibodies or humanized antibodies can be prepared by methods commonly known to one skilled in the art. For example, human antibodies can be made by, immunizing a mouse whose immune system has been changed to that of humans, with the transcriptional regulatory factor of the invention. Also, humanized antibodies can be prepared by, for example, cloning the antibody gene from monoclonal antibody producing cells and using the CDR graft method which transplants the antigen-recognition site of the gene into a known human antibody.

The present invention also relates to a method for screening a compound that binds to the transcriptional regulatory factor of the invention. The screening method of the invention includes the steps of, (a) exposing a test sample to the transcriptional regulatory factor of the invention, (b) detecting the binding activity between the test sample and the transcriptional regulatory factor of the invention, and (c) selecting a compound having an activity to bind to the transcriptional regulatory factor of the invention. Any test sample can be used for the screening without particular restrictions. Examples are, cell extracts, culture supernatants, synthetic low molecular weight compound libraries, purified proteins, expression products of gene libraries, synthetic peptide libraries, and so on.

Isolation of a compound that binds to the transcriptional regulatory factor using said transcriptional regulatory factor can be done using methods commonly known to one skilled in the art. The screening of a protein which binds to the transcriptional regulatory factor of the invention can be done by, for example, creating a cDNA library from tissues or cells (for example, testis tissue cells and tumor cell lines) expected to express a protein binding to the transcriptional regulatory factor of the invention using a phage vector (λgt11 and Zap, etc.), expressing this cDNA library on LB-agarose, fixing the expressed proteins on the filter, biotin-labeling the transcriptional regulatory factor of the invention or purifying it as a fusion protein with GST protein, reacting this with the above-described filter, and detecting plaques expressing the binding proteins using streptavidin or anti-GST antibody (West Western Blotting method) (Skolnik et al. (1991) Cloning of PI3 kinase-associated p85 utilizing a novel method for expression/cloning of target proteins for receptor tyrosine kinases, Cell 65:83–90). The screening of a protein binding to the transcriptional regulatory factor of the invention or its gene, can also be done by following "the two-hybrid system" ("MATCHMAKER Two-hybrid System", "Mammalian MATCHMAKER Two-Hybrid Assay Kit", "MATCH-MAKER One-Hybrid System" (Clontech), "HybriZAP Two-Hybrid Vector System" (Stratagene), or Reference— "Dalton S, and Treisman R (1992) Characterization of SAP-1, a protein recruited by serum response factor to the c-fos serum response element. Cell 68, 597–612"). In the two-hybrid system, the transcriptional regulatory factor of the invention is fused to the SRF-binding region or GAL4-binding region and expressed in yeast cells. A cDNA library, is prepared from cells expected to express a protein binding to the transcriptional regulatory factor of the invention, in a way that the library is expressed in the form of being fused to the VP16 or GAL4 transcriptional activation region. The cDNA library is then introduced into the above yeast cells and the cDNA derived from the library is isolated from the positive clones detected (when a protein binding to the transcriptional regulatory factor of the invention is expressed in yeast cells, the binding of the two activates a reporter gene making positive clones detectable). A protein binding to the transcriptional regulatory factor of the invention can be recovered by, introducing the cDNA isolated above to $E.$ $coli$ and expressing the protein encoded by said cDNA.

Also, a protein binding to the transcriptional regulatory factor of the invention can be screened by, applying the culture supernatants or cell extracts of cells expected to express a protein binding to the transcriptional regulatory factor of the invention onto an affinity column in which the protein of the invention is immobilized and purifying the protein that binds specifically to the column.

The method of screening molecules that bind when the immobilized transcriptional regulatory factor of the invention is exposed to synthetic chemical compounds, or natural substance banks, or a random phage peptide display library, or the method of screening using high-throughput based on combinatorial chemistry techniques (Wrighton et al., Small peptides as potent mimetics of the protein hormone erythropoietin, Science (UNITED STATES) (1996), 273:458–464; Verdine G. L., The combinatorial chemistry of nature, Nature (ENGLAND) (1996) 384:11–13; Hogan J. C., Jr., Directed combinatorial chemistry. Nature (ENGLAND) (1996) 384:17–19) to isolate low molecular weight compounds, proteins (or their genes) and peptides are methods well known to one skilled in the art.

A biosensor using the surface plasmon resonance phenomenon may be used as a mean for detecting or quantifying the bound compound in the present invention. When such a biosensor is used, the interaction between the protein of the invention and a test compound can be observed real-time as a surface plasmon resonance signal, using only a minute amount of proteins without labeling (for example, BIAcore, Pharmacia). Therefore, it is possible to evaluate the binding between the transcriptional regulatory factor of the invention and a test compound using a biosensor such as BIAcore.

The present invention also relates to a method for screening a compound able to promote or inhibit the binding between the transcriptional regulatory factor of the invention and an interacting-protein. Detection of a binding between the TCoA1 protein and hSNF2H, hSNF2L, NCoA-62/Skip or homologues thereof enabled such a screening. This screening can be done using the method comprising the steps of: (a) exposing the transcriptional regulatory factor of the invention to hSNF2H, hSNF2L, NCoA-62/Skip or homologues thereof, under the presence of a test sample; (b) detecting the binding activity between the transcriptional regulatory factor of the invention and hSNF2H, hSNF2L, NCoA-62/Skip or homologues thereof; and (c) selecting a compound which decreases said binding-activity when compared with the assay in the absence of a test sample (control).

There are no particular restrictions as to the test sample used. Examples are, cell extracts, culture supernatants, libraries of synthetic low molecular weight compounds, purified proteins, expression products of gene libraries, synthetic peptide libraries, etc. The compound isolated by the above-described screening of a protein binding to the protein of the invention may also be used as a test sample.

The transcriptional regulatory factor of the invention used for the screening may be a whole protein or a partial peptide comprising binding regions with hSNF2H, hSNF2L, NCoA-62/Skip or homologues thereof. hSNF2H, hSNF2L, NCoA-62/Skip or homologues thereof used for the screening may be whole proteins or partial peptides comprising binding regions with the transcriptional regulatory factor of the invention.

The detection of the binding activity between the transcriptional regulatory factor of the invention and hSNF2H, hSNF2L, NCoA-62/Skip or homologues thereof, can be performed, for example, as follows.

A test sample and hSNF2H, hSNF2L, NCoA-62/Skip or homologues thereof is added to the transcriptional regulatory factor of the invention immobilized on a microplate, reacted with a mouse or rabbit antibody against hSNF2H, hSNF2L, NCoA-62/Skip or homologues thereof, further reacted with an anti-mouse or anti-rabbit antibody labeled with peroxidase, alkaline phosphatase and such, a labeled enzyme substrate is added and the enzyme activity is measured. Compounds that show an enzyme activity that is lower to or higher than that in the absence of a test sample, are selected. Thereby, compounds having an activity to promote or inhibit the binding between the transcriptional regulatory factor of the invention and hSNF2H, hSNF2L, NCoA-62/Skip or homologues thereof are obtained.

This screening may be performed also by, using hSNF2H, hSNF2L, NCoA-62/Skip or homologues thereof as the immobilized protein, and the transcriptional regulatory factor of the invention as the protein that is added with the test sample.

Also, the transcriptional regulatory factor of the invention or hSNF2H, hSNF2L, NCoA-62/Skip or homologues thereof added together with the test sample may be directly labeled with peroxidase, or alkaline phosphatase, or used as a fusion protein with such enzymes. Compounds having an activity that activates or inhibits the binding between the transcriptional regulatory factor of the invention and hSNF2H, hSNF2L, NCoA-62/Skip or homologues thereof may also be selected by, expressing as fusion proteins with enzymes other than the above, such as, luciferase, β-galactosidase, or GFP protein and measuring the inhibition or promotion of the enzyme activity by a test sample. The mammalian two-hybrid system (Clontech, Palo Alto) can also be used to screen a compound that promotes or inhibits the binding between the transcriptional regulatory factor of the invention and an interacting-protein. Namely, using the two-hybrid system, the transcriptional regulatory factor of the invention and an interacting-protein is expressed in mammalian cells, a test sample is added to said mammalian cells, and then reporter-activity is measured. The detected reporter-activity is compared, and compounds that give a value that is lower to or higher than the reporter-activity in the absence of a test sample, are selected. Thus, a compound that promotes or inhibits the binding between the transcriptional regulatory factor of the invention and hSNF2H, hSNF2L, NCoA-62/Skip or homologues thereof can be obtained.

A compound screened by the screening of the invention may be applied for the prevention and treatment of cancer and other cell-proliferation-linked diseases. When using the isolated compound as a pharmaceutical for humans and other mammals, such as, mice, rats, guinea-pigs, rabbits, chicken, cats, dogs, sheep, pigs, monkeys, baboons, chimpanzees, the isolated compound can be directly administered or can be formulated into a dosage form using known pharmaceutical preparation methods. For example, according to the need, the drugs can be taken orally as sugar-coated tablets, capsules, elixirs and microcapsules or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, solvents, surfactants, stabilizers, flavoring agents, excipients, vehicles, preservatives and binders, in a unit dose form required for generally accepted drug implementation. The amount of active ingredients in these preparations makes a suitable dosage within the indicated range acquirable.

Examples for additives which can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers; may be formulated with a buffer such as phosphate buffer and sodium acetate buffer; a pain-killer such as procaine hydrochloride; a stabilizer such as benzyl alcohol, phenol; and an anti-oxidant. The prepared injection is filled into a suitable ampule.

Methods well known to one skilled in the art may be used to administer a pharmaceutical compound to patients, for example as intraarterial, intravenous, percutaneous injections and also as intranasal, transbronchial, intramuscular or oral administrations. The dosage and method of administration vary according to the body-weight and age of a patient and the administration method but one skilled in the art can suitably select them. If said compound is encodable by a DNA, said DNA can be inserted into a vector for gene therapy and perform the therapy. The dosage and method of administration vary according to the body-weight, age, and symptoms of a patient but one skilled in the art can select them suitably.

For example, although there are some differences according to the symptoms, the dose of a compound that binds with the transcriptional regulatory factor of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

This invention also features a DNA containing at least 15 nucleotides, which can specifically hybridize with DNA encoding the "TCoA1" protein. The term "specifically hybridize" as used herein, indicates that cross-hybridization does not occur significantly with DNA encoding other proteins, in the above-mentioned hybridizing conditions, preferably under stringent hybridizing conditions. Such DNA includes, probes, primers, nucleotides and nucleotide derivatives (for example, antisense oligonucleotides and ribozymes), which specifically hybridize with DNA encoding the protein of the invention or its complementary DNA.

The present invention includes an antisense oligonucleotide that hybridizes with any site within the nucleotide sequence of SEQ ID NO:2 or 9. This antisense oligonucleotide is preferably that against the at least 15 continuous nucleotides in the nucleotide sequence of SEQ ID NO:2 or 9. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products are, lower alkyl phosphonate modifications such as methyl-phosphonate-type or ethyl-phosphonate-type, phosphothioate modifications and phosphoramidate modifications.

The term "antisense oligonucleotides" as used herein means, not only those in which the entire nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NO:9.

Such DNAs are indicated as those having, in the "at least 15 continuous nucleotide sequence region", a homology of at least 70% or higher, preferably at 80% or higher, more preferably 90% or higher, even more preferably 95% or higher. The algorithm stated herein can be used to determine homology. Such DNAs are useful as probes for the isolation or detection of DNA encoding the protein of the invention as stated in a later example or as a primer used for amplifications.

The antisense oligonucleotide derivative of the present invention, acts upon cells producing the protein of the invention by binding to the DNA or mRNA encoding the protein and inhibits its transcription or translation, promotes the degradation of the mRNA, inhibiting the expression of the protein of the invention resulting in the inhibition of the protein's function.

The antisense oligonucleotide derivative of the present invention can be made into an external preparation such as a liniment and a poultice by mixing with a suitable base material, which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following usual methods.

The antisense oligonucleotide derivative is given to the patient by, directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the invention inhibits the expression of the protein of the invention and thereby useful for suppressing the biological activity of the protein of the invention. Also, expression-inhibitors comprising the antisense oligonucleotide of the invention are useful in the point that they can inhibit the biological activity of the protein of the invention.

CH4C3: CH4C3 zinc-finger; bHLH: basic helix-loop-helix; Q-rich: glutamine-rich; C2HC4: C2HC4 zinc-finger; BDM: bromodomain; T: LXXLL motif.

Figure 2A:
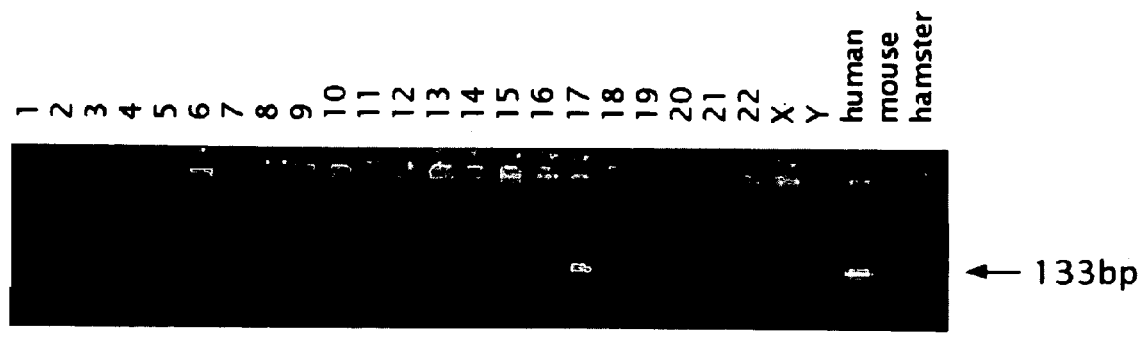

FIG. 2a shows the results of analysis of mono-chromosome hybrid cell panel against chromosome no. 17 using nb15G and nb15H primers. Shows the human chromosome including each hybrid. The product of 133 bp was specifically amplified in GM10498 cell-system, which is a mono-chromosome of human chromosome no. 17.

Figure 2B:
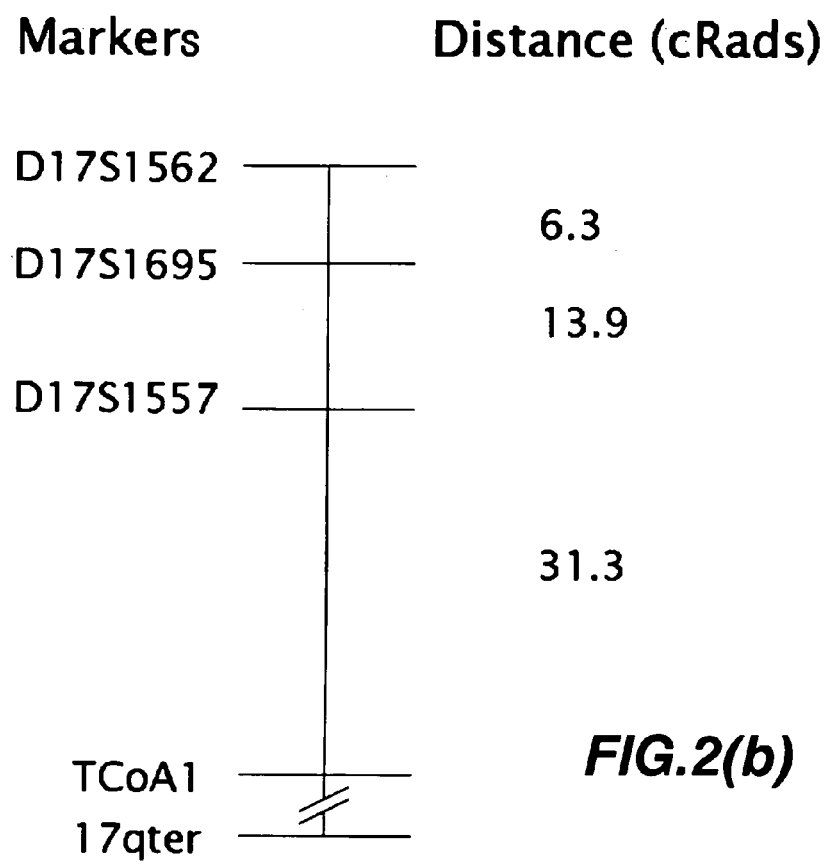

FIG. 2b shows the result of GeneBridge 4 radiation hybrid panel analysis by which the location of "TCoA1" was determined on chromosome no. 17.

FIG. 3a–b shows the electrophoretic pattern of the "TCoA1" expression in normal human tissues as detected by northern-blot analysis. "TCoA1" was used as the probe when hybridizing the filter in "3a" and actin was used in "3b". The right side of the figure shows markers.

Figure 4:
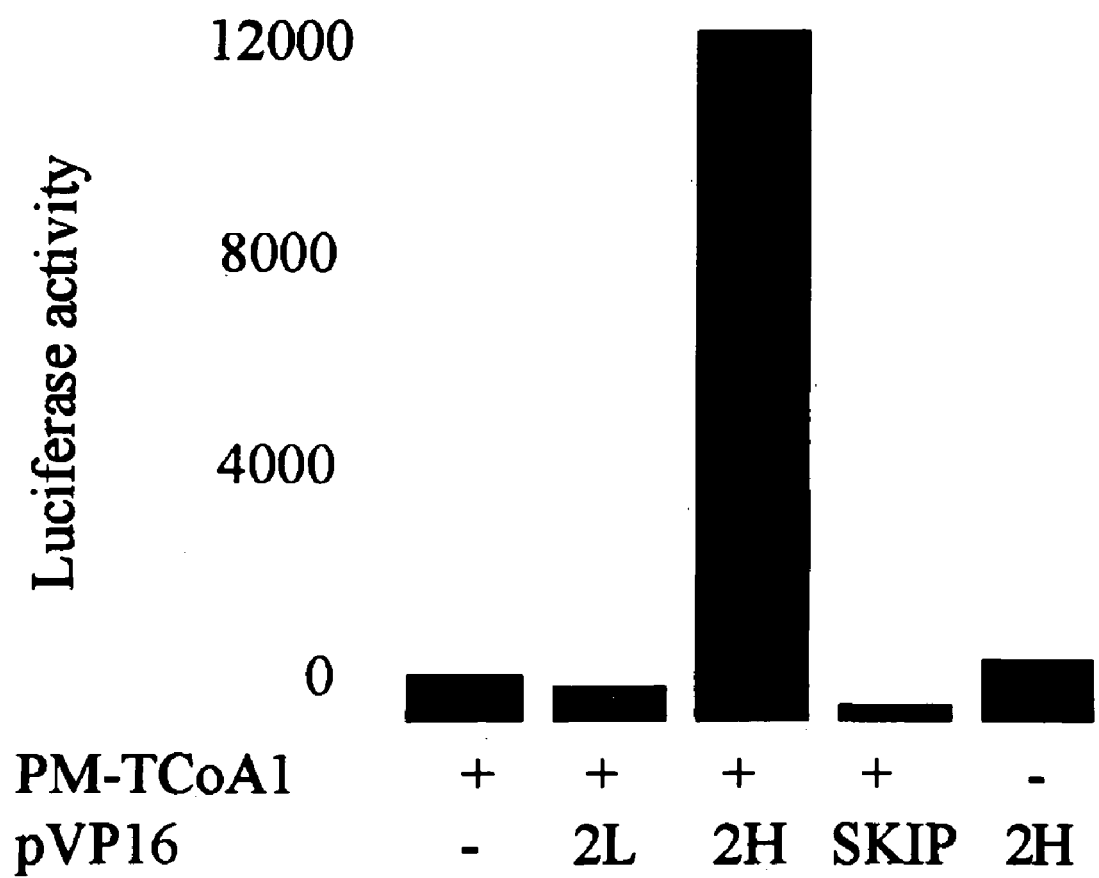

FIG. 4 shows the results obtained by using the mammalian two-hybrid analysis system detecting the interaction between "TCoA1" and hSNF2H, hSNF2L, and NcoA-62/Skip.

Figure 5:
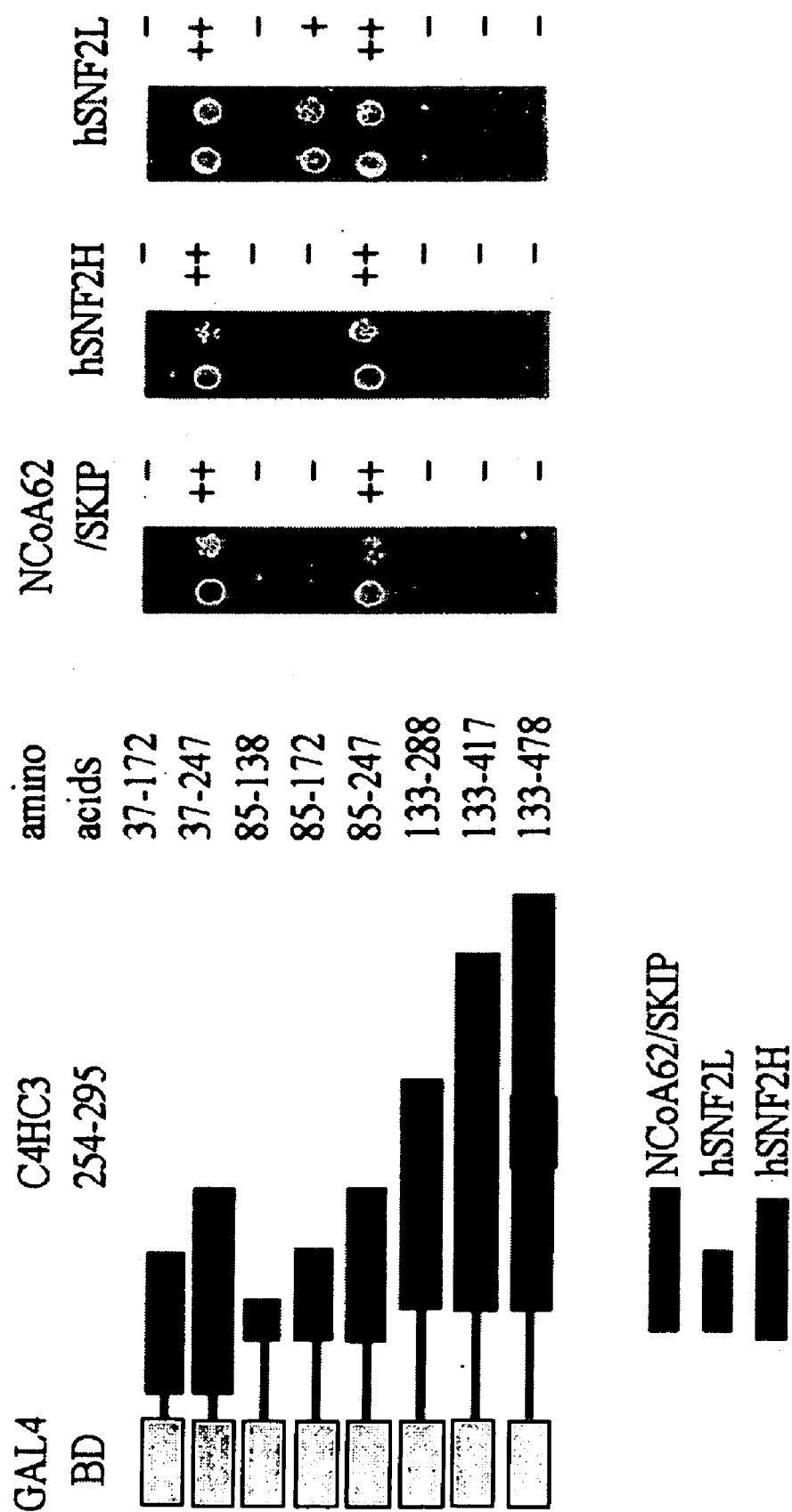

FIG. 5 shows the map of the interaction between the C-terminus of TCoA1 and hSNF2H, hSNF2L, or NcoA-62/Skip.

Figure 6:
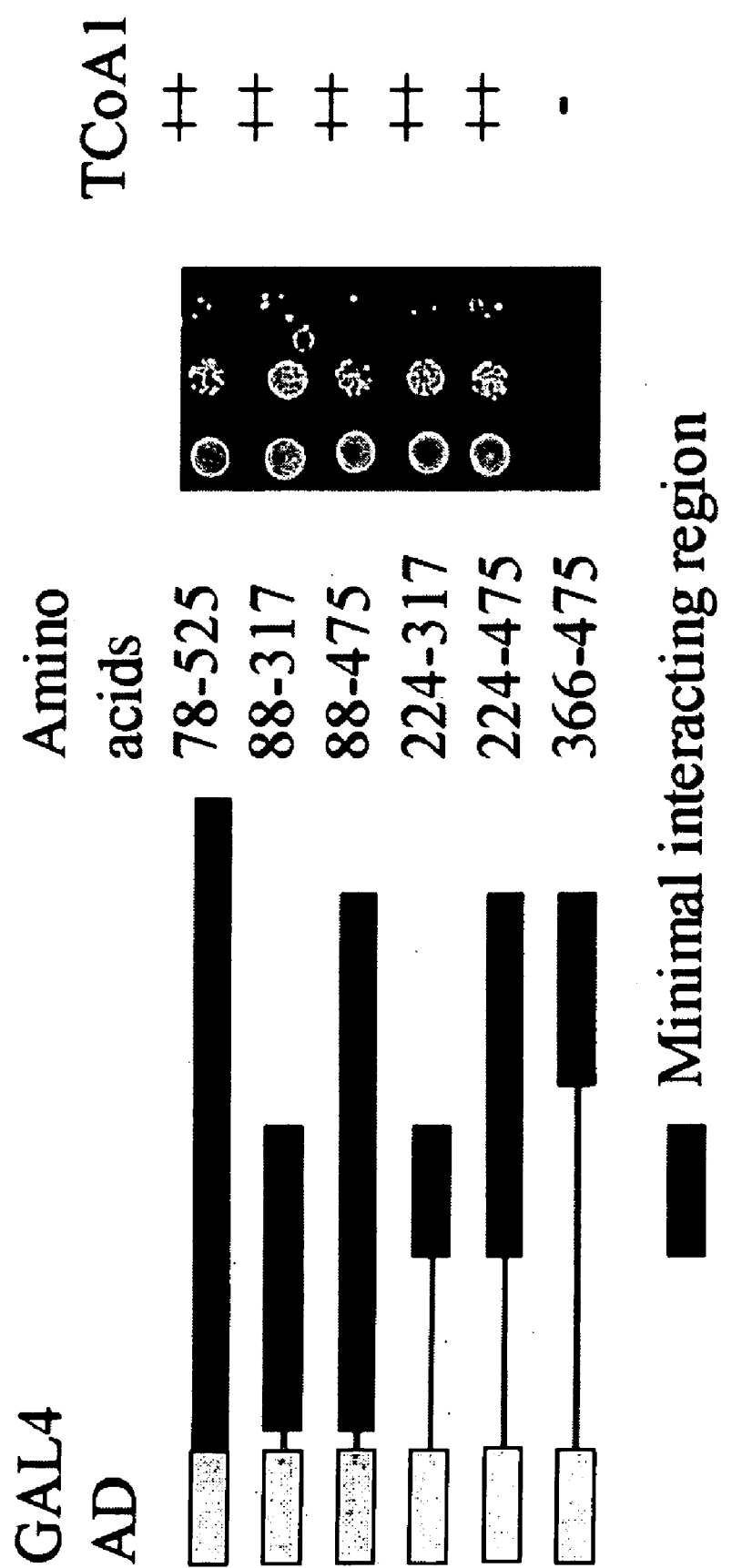

FIG. 6 shows the map of the interaction between TCoA1 and NcoA-62/Skip. The minimal interacting region (position 224–317) is shown at the bottom.

Figure 7:
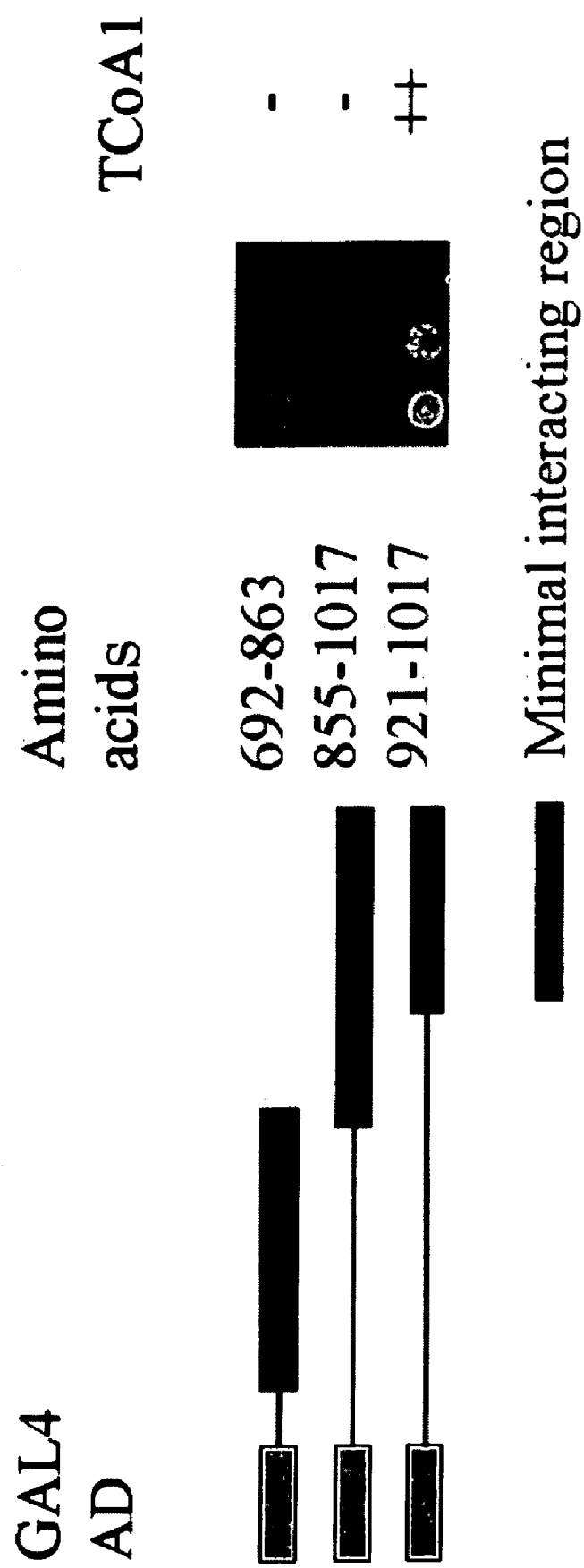

FIG. 7 shows the map of the interaction between TCoA1 and hSNF2H. The minimal interacting region (position 921–1017) is shown at the bottom.

Figure 8:
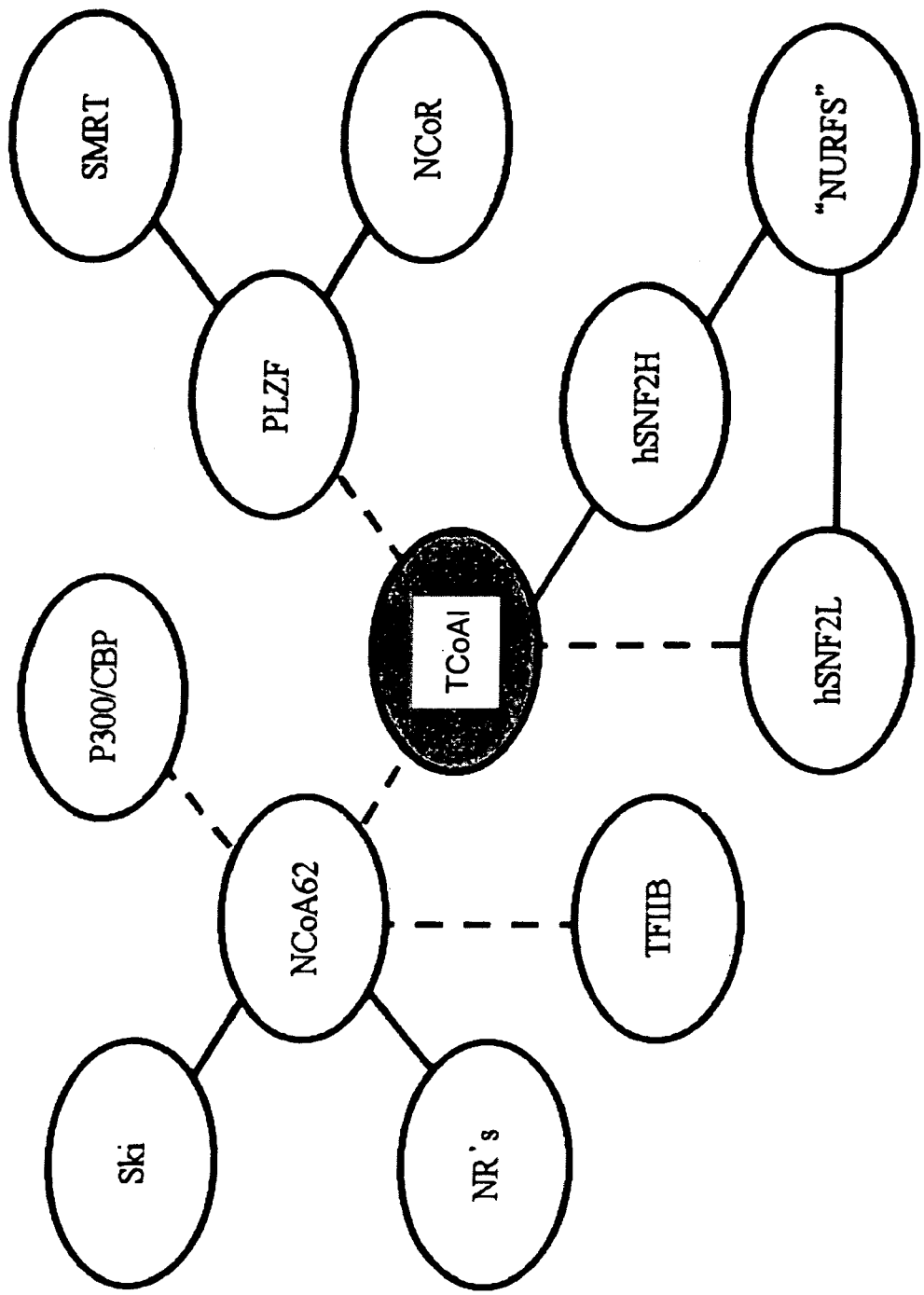

FIG. 8 shows the proteins that associate in the interaction with TCoA1. Unverified interactions are shown in dashed lines.

DETAILED DESCRIPTION OF THE INVENTION

The present invention will be explained in detail below with reference to examples, but it is not construed as being limited thereto.

EXAMPLE 1

Isolation of the "TCoA1" Gene (1) Identification of a Novel Gene comprising a Bromodomain EST database was BLAST searched using various nucleotide sequences encoding known bromodomain motifs. As a result, several potential bromodomain-gene-encoding ESTs were identified by the search using nucleotide sequence of *Tetrahymena thermophila* HATA1 gene (Brownwell et al., (1996) Cell 84:843–851). One of these ESTs, the fetal lung cDNA library-derived EST (WI 7142), was discovered to provide a novel gene.

(2) Isolation of Full-Length Nucleotide Sequence

The cloning of full-length cDNA against ESTW17142 was done as follows. First the PCR primers nb15U (GGAT-TATGAGGGGTTGAAGAGGG/SEQ ID NO:3) and nb15L (AAGGCAACAGAGTCTGTAGCCCAA/SEQ ID NO:4) were designed and a 119 bp amplification product was obtained by the polymerase chain reaction using testicular cDNA as the template. The amplified product was directly purified by a QIAquick (Qiagen) purifying column. Next, the testicular cDNA library (HL3024a, Clontech) was screened using this amplification product as the probe, and a re-screening of the library was done using the cDNA clone comprising the above-mentioned EST sequence. The above probe was [α-$^{32}$P]dCTP labeled by random priming and purified by CHROMA SPIN 10 column (Clontech). The library-filter was hybridized using ExpressHyb Hybridization Solution (Clontech) for one hour at 65° C. The filter was washed at 65° C. with 0.5×SSC. 0.1% SDS until it reached the final stringency. Next, in order to identify the hybridizing clone, autoradiography was performed at –70° C. for one to three days. The same procedure was done repeatedly until the obtained clones were linked to acquire a nucleotide sequence covering the whole coding-regions of the gene. All nucleotide sequences were determined by the ABI377 Auto Sequencer using ABI dye-terminator chemistry. Since clones of the 5' terminus were high in GC content, subcloning to the plasmid was done prior to sequence determination.

Figure 1:
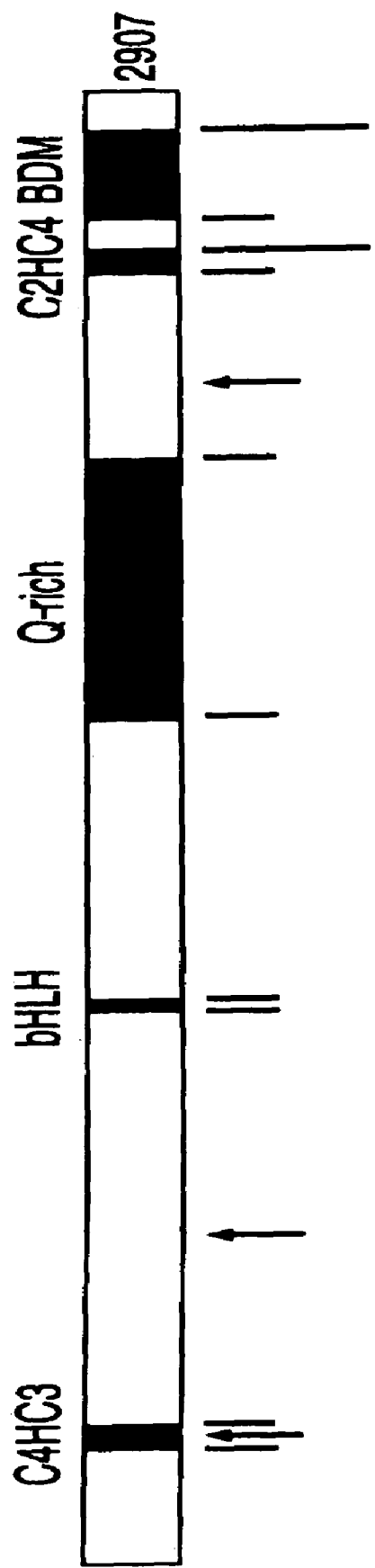
FIG. 1 shows the alignment of the domains identified in "TCoA1". The symbols within the figure are shown below.

The library-screening gave 9865 bp nucleotide sequence. In this whole nucleotide sequence, an open reading frame (ORF) existed, which encoded 2993 amino acids terminating at nucleotide position 8979. This ORF was followed by 3'UTR of 877 bp until the polyA tail (FIG. 1). This sequence is believed to be the whole sequence since, the length of the sequence is comparable to the 10.5 Kb shown by northern blot analysis, and since the 5' terminus is GC rich and coincides with the existence of a CpG island seen at initiation points of many genes (Cross et al. (1995) Curr. Opin. Genet. Dev. 5:309–314). The nucleotide sequence of isolated cDNA is shown in SEQ ID NO:2 and the amino acid sequence of the protein encoded by said cDNA in SEQ ID NO:1.

(3) Determination of Homology and the Motif Characteristics of the Transcriptional Factor The motif was searched by PROSITE. The comparisons of proteins were done using Bestfit within GCG The nuclear localization signal was identified by PSORT. Motif search revealed that several conserved regions and domains were located in the amino acid sequence of presumed proteins (FIG. 1). These conserved regions had the C4HC3 zinc-finger (Aasland et al. (1995) Trends Biochem. Sci. 20:56–59; Koken et al. (1995) CR Acad. Sci. III, 318: 733–739), a basic helix-loop-helix domain (Murre et al. (1989) Cell 58:537–544), an extensive hydrophobic glutamine-rich domain, CH2CH3 zinc-finger, and a bromo-domain. Furthermore, there is a LXXLL motif (Torchia et al. (1997) Nature 387:677–684; Heery et al. (1997) Nature 387:733–736) that most likely furnishes the interaction with nuclear receptors. All these motifs have the characteristic to present the functions as a transcriptional regulatory factor. As a result of the PSORT program, in all, eight consensus sequences were discovered at the nuclear site, which closely associate with the above function (Robbins et al. (1991) Cell 64:615–23). Expressing the function of the gene, it was named "TCoA1" (transcriptional co-activator).

When the nucleotide sequence of "TCoA1" is analyzed upon the non-redundant DNA database, it was found that "TCoA1" has a 100% homology with 2,183 bp of the FAC1 gene (Zhu et al. (1996) Biochemica et Biophysica Acta 1309:5–8) presumed to encode a protein of 810 residues. FAC 1 was initially isolated by immunoscreening of an expression library using Alz50 (Bowser et al. (1995) Dev. Neuroscience 17:20–37) monoclonal antibody. In addition to having a region that coincides spanning an extensive region with the nucleotide sequence of "TCoA1", FAC1 also coincides with the "TCoA1" results, which were obtained using the external nucleotide sequence of the region that overlaps with FAC 1, in the transcription size (Bowser et al. (1995) Dev. Neuroscience 17:20–37) and localization (Zhu et al. (1996) Biochemica et Biophysica Acta 1309:5–8). In other words, it can be envisaged that the 2673 bp nucleotide sequence of FAC 1 is a partial sequence that is equivalent to the nucleotides from nucleotide position 248 of the 5'terminus' to nucleotide position 2631. Comparison of the nucleotide sequences of FCA1 and TCoA1 revealed that a single nucleotide-deleted error sequence (at position 2400 A) exists in FAC 1, and thus, it can be assumed that translation terminates at an early stage together with the shift of the reading frame of ORF. Similarly, a misrecognition of the initiation point of methionine residue had been triggered by a 5' terminus sequence error in FAC 1.

The predicted amino acid sequence of "TCoA I" has several extensive regions that have homologies with the presumed proteins of nematode (C. elegans), F26H11.2, F26H11.3a and F26H11.3b (Wilson at al., (1994) Nature 368:32–38). Results of analysis using "Gene Finder" software made the prediction of the gene that encodes these proteins possible by searching the genomic sequences contained in the F26H11 cosmid. The nucleotide sequences of "TCoA1" N terminus coincided with F26H11.g and C terminus with F26H11.I. This result showed that the both proteins presumed by "TCoA1" and FCA1 are equivalent to a single protein in the nematode, and it is believed that "TCoA1" is the human homologue of the nematode protein.

EXAMPLE 2

Chromosome Mapping of "TCoA1"

To determine the chromosomal location of "TCoA1", DNA obtainable from each of the 24 monochromosomal human/rodent somatic cell lines (Dubois et al. (1993) Genomics 16:315–319) acquired from Coriell Cell Repositories, New Jersey, were amplified using the PCR primers nb15G (CCTCAGCTGCAACAAGTCC/SEQ ID NO:5) and nb15H (GCACTGCTTTGCTGAATTTGGA/SEQ ID NO:6). As predicted, 133 bp PCR product was amplified from the GM 10567 cell system suggesting the possibility that the gene of the invention is located on human chromosome no.17 (FIG. 2A).

The "TCoA1" region locus was determined using Genebridge4 radiation hybrid panel of 91 hybrids (Walter et al. (1994) Nature Genetics 7:22–28). Screening was done by re-using primer-G and primer-H and performing PCR for that hybrid panel. By evaluating the respective hybrids as being positive or negative in regard to amplification, the binary code produced was compared with the similarity code for the marker that forms the framework map using the server at the web-address www-genome.wi.mit.edu/cgi-bin/contig/rhmapper.pl to determine the chromosomal location of the gene of the invention. "TCoA1" recognized to be located in the marker D17S1557 (FIG. 2B). Only a score below 11 showing the possibility of "TCoA1" existing at a site away from D17S1557 was detected. This site coincides with the results by FISH showing FAC1 is on chromosome no. 17 q24 (Bowser (1996) Genomics 38:455–457).

To find out a more precise location of "TCoA1", screening by hierarchical PCR (Jones et al. (1994) Genomics 24:266–275) using the CEPH mega-YAC library and primers nb15S (AAGATGTTGTCTTGGAGCCGT/SEQ ID NO:7) and nb15Q (TTTTTTACCATTTGCTTCAGTCCC/SEQ ID NO:8). The single clone 983d12 was identified but no information of this clone was obtainable even by searching the map information of YAC 983d12 using CEPH infoclone database (www.cephb.fr/infoclone.html). However, hybridization of Alu-PCR products showed that the two clones (902c10 and 938f7) which partially overlap with 983d12, were both positive against D17S789 at the end of D17S1557. This coincides with the results of radiation hybrid obtained by the Inventors and from a cytogenetic point-of-view, means that "TCoA1" is located on chromosome no. 17 q23 (Collins et al. (1996) Proc. Natl. Acad. Sci. USA 93:14771–14775). Though slightly different, this location is close to the chromosome no. 17 q24 (Bowser (1996) Genomics 38:455–457) location reported for FAC1.

EXAMPLE 3

Analysis of "TCoA1" Expression

Northern hybridization was done using 240 bp cDNA probe and 16 normal tissues as panels. The probe was [α-$^{32}$P]dCTP labeled by random priming and purified by CHROMA SPIN 10 column (Clontech). Hybridization for northern analysis was done using ExpressHyb Hybridization Solution (Clontech) for one hour at 65° C. The filter was washed at 65° C. with 0.5×SSC, 0.1% SDS until it reached the final stringency. Next, in order to identify hybridizing transcripts, autoradiography was performed at −70° C. for one to three days. mRNA blot was purchased from Clontech, and hybridization was done using the 240 bp cDNA probe equivalent to the nucleotide position 300–450. Approximately 10.5 kb mRNA was detected in almost all tissues, and the size of the transcripts was equivalent to that of ORF identified by the nucleotide sequence, and also coincided with the reported results for FAC1 (FIG. 3).

EXAMPLE 4

Determination of the Full-Length cDNA Nucleotide Sequence of TCoA1

To obtain a complete cDNA, the Inventors screened the testicular cDNA library (HL3024a, Clontech) again using the 119 bp amplification product of Example 1 (2) as the probe. Screening was done under the same conditions as Example 1 (2).

When the cDNA nucleotide sequence obtained by the above screening was read, it was a sequence of 9700 nucleotides in which an inframe stop codon existed upstream the methionine initiation codon. Thus, the obtained cDNA was revealed to be full-length. The nucleotide sequence of the isolated full-length cDNA is given in SEQ ID NO:9, and the amino acid sequence of the protein encoded by said cDNA in SEQ ID NO:10.

When the nucleotide sequence of TCoA1 was compared with FAC1 (Zhu et al. (1996) Biochemica et Biophysica Acta 1309:5–8), the following nucleotide sequences coincided almost fully: position 57–1519 of FAC-1 with position 461–1917 of TcoA1, and position 1898–2622 of FAC-1 with position 1918–2643 of TCoA1. However, the position 1520–1897 of FAC-1 does not exist in the nucleotide sequence of TCoA1. The nucleotide sequence of TCoA1 has an open reading frame (ORF) coding 2781 amino acids, whereas the nucleotide sequence of FAC-1 has an ORF equivalent to a mere 810 amino acids, which is only a small part of TCoA1 beginning with a methionine initiation codon. The amino acid sequence of TCoA1 maintains two C4HC3 zinc-fingers (amino acid position 254–295) and one bromodomain (amino acid position 2684–2747). There is also an extensive glutamine-rich region (amino acid position 1840–2400).

EXAMPLE 5

Identification of Proteins Interacting with the N Terminal Region of TCoA1

Using a cDNA clone encoding the first 482 amino acids of TcoA1 including the C4HC3 zinc finger, yeast two-hybrid cDNA library (Clontech, Palo Alto) of the mouse-testis and human-brain was screened. This yeast two-hybrid cDNA library screening was done using yeast-vector PJ69-4A (James et al. (1996) Genetics 144(4):1425–36) according to the protocol of Clontech.

As a result, hSNF2H gene (Aihara et al. (1998) Cytogenet Cell Genet 81(3–4):191–3) was isolated from the human cDNA library, and the corresponding gene was isolated from the mouse cDNA library. hSNF2L gene (Aihara et al. (1998) Cytogenet Cell Genet 81(3–4): 191–3) and also, a transcriptional co-activator NCoA-62 (also known as Skip) (Baudino et al. (1998) J. Biol. Chem. 273(26):16434–41, Dahl et al. (1998) Oncogene 16(12):1579–86) were isolated from the human cDNA library.

hSNF2H/2L is the human homologue of *D. melanogaster*'s ISWI. This ISWI protein has been discovered within the chromatin reconstruction complex and this complex has been reported to be the molecular-device that reconstructs nucleosomes upon DNA in an ATPase-dependent manner (Varga-Weisz et al. (1998) Curr. Opin. Cell Biol 10(3):346–53). Within these complexes, hSNF2H and hSNF2L acts as an ATPase subunit.

Recently, there was a report suggesting the possibility that ISWI alone has an activity to reconstruct chromosomes (Corona et al. (1999) Mol. Cell 3(2):239–45). A 50 amino acid deletion at the C terminus was found when the obtained full-length sequence of hSNF2H was compared with the sequence on the database (GenBank Accession No.AB010882) and alternative splicing is believed to be occurring.

NCoA-62/Skip is a transcriptional co-activator interacting with Ski, a viral oncoprotein and ligand-binding domains of various nuclear receptors (VDR, RAR). NCoA-62/Skip also has a homology with the fruit fly (*Drosophila*) Bx42 protein induced by ecdysone.

To verify the interactions between TCoA1 and above-mentioned proteins, analysis was done using constructs of mammalian two-hybrid system (Clontech, Palo Alto) according to protocols of Clontech. As a result, though a specific interaction could be found between TCoA1 and hSNF2H (FIG. 4), no interaction was seen for hSNF2L and Skip. Judging by the similarity of hSNF2H and hSNF2L, the lack of hSNF2L interaction was surprising and hSNF2L was probably not expressed in this system.

EXAMPLE 6

The Interaction Map of TCoA1

The experiment for the construction of the interaction map was done as follows, using the yeast two-hybrid system. cDNAs encoding various regions (refer FIG. 5) were cloned to pAS vector (Clontech). Also cDNAs encoding the three proteins (hSNF2H, hSNF2L and NCoA-62/Skip) used in the detection of interaction with various regions of TCA1, were cloned to the pACT vector (Clontech). A combination of these vectors were introduced to a yeast-host (PJ69–4A), and the interaction between proteins expressed within said host was detected using luciferase as the reporter.

The results revealed a region that interacts with all three proteins (hSNF2H, hSNF2L and bx42 (NCoA-62/Skip)). Namely, as seen in FIG. 5, all three proteins interacted with the 85–247 amino acids of TCoA1.

This fact revealed that C4HC3 zinc finger known to be a protein interacting site was omitted from the site interacting with these 3 proteins.

EXAMPLE 7

Functional Analysis of the Bromodomain Interacting Protein

The clones (hSNF2H, hSNF2L, NCoA-62/Skip) interacting with TCoA1 identified by the yeast two-hybrid screening, encode a huge polypeptide. Accordingly, the Inventors next identified the regions within these proteins that interact with TCoA1, using the yeast two-hybrid system. Specifically, a pACT vector (Clontech) constructs (FIG. 6, FIG. 7), which contained cDNA encoding a series of partially overlapping polypeptides within NcoA-62 and hSNF2H, were prepared and introduced to yeast cells (PJ69-4A) together with the pAS vector (Clontech) containing cDNA encoding the amino acids of the 1–525 site of TCoA1 protein, and the interaction between proteins expressed within said host was detected using luciferase as the reporter.

For NcoA-62, the region of approximately 450 amino acids including the complete carboxyl terminus domain of the original clone, and the series of five deletion clones in the said region were examined (FIG. 5). As a result, amino acids of the position 224–317 within NcoA-62 were identified as the region interacting with TCoA1.

As for hSNF2H, the three deletion clones were analyzed (FIG. 7). As a result, the region within hSNF2H that interacts with TCoA1 protein was mapped to the carboxyl terminus (position 921–1017). The other clone having the same region (position 855–1017) failed to show any interaction. This may be due to the fact that this clone makes a special secondary structure.

INDUSTRIAL APPLICABILITY

The transcriptional regulatory factor and the DNA encoding said factor can be used for the treatment of cancer and other cell-proliferation-linked diseases and also for the screening of drug-candidate compounds. Furthermore, antibodies binding to the transcriptional regulatory factor of the present invention, compounds that regulate the function of said transcriptional regulatory factor, and compounds that inhibit the interaction between said transcriptional regulatory factor and other proteins, may be utilized as therapeutic agents and preventive drugs for these diseases.

What is claimed is:

1. An isolated nucleic acid consisting of SEQ ID NO:2 or SEQ ID NO:9.

2. An isolated nucleic acid comprising SEQ ID NO:2 or SEQ ID NO:9.

3. An isolated nucleic acid encoding a polypeptide comprising a sequence as set forth in SEQ ID NO:1 or 10.

4. An isolated nucleic acid comprising a strand that hybridizes under stringent conditions to a single stranded probe, the sequence of which probe consists of SEQ ID NO:2 or 9 or the complement thereof, wherein the nucleic acid encodes a polypeptide that contains at least one bromodomain and binds to a protein selected from the group consisting of hSNF2H, hSNF2L, and NCoA-62/Skip, and wherein the stringent conditions comprise hybridization and washing at 50° C. in 2×SSC containing 0.1% SDS.

5. The nucleic acid of claim 4, wherein the polypeptide comprises a sequence of as set forth in SEQ ID NO:1 or 10.

6. The nucleic acid of claim 4, wherein the strand is at least 3000 nucleotides in length.

7. A vector comprising the nucleic acid of claim 1.

8. A vector comprising the nucleic acid of claim 2.

9. A vector comprising the nucleic acid of claim 3.

10. A vector comprising the nucleic acid of claim 4.

11. A cultured host cell comprising the nucleic acid of claim 1.

12. A cultured host cell comprising the nucleic acid of claim 2.

13. A cultured host cell comprising the nucleic acid of claim 3.

14. A cultured host cell comprising the nucleic acid of claim 4.

15. A method of producing a polypeptide, the method comprising culturing the cultured host cell of claim 11 in a culture, expressing the polypeptide encoded by the nucleic acid in the cultured host cell, and isolating the polypeptide from the culture.

16. An isolated nucleic acid encoding a polypeptide the sequence of which comprise the amino acid sequence of SEQ ID NO:1 or SEQ ID NO:10 with 0 to 50 conservative amino acid substitutions, wherein the polypeptide binds to a protein selected from the group consisting of hSNF2H, hSNF2L, and NCoA-62/Skip.

17. The isolated nucleic, acid of claim 16, wherein the number of conservative amino acid substitutions is 0 to 30.

18. The isolated nucleic acid of claim 16, wherein the number of conservative amino acid substitutions is 0 to 10.

19. An isolated nucleic acid comprising a nucleotide sequence that is at least 70% identical to SEQ ID NO:2 or SEQ ID NO:9, wherein the nucleic acid encodes a polypeptide that contains at least one bromodomain and binds to a protein selected from the group consisting of hSNF2H, hSNF2L, and NCoA-62/Skip.

20. The isolated nucleic acid of claim 19, wherein the nucleotide sequence is at least 90% identical to SEQ ID NO:2 or SEQ ID NO:9.

21. The isolated nucleic acid of claim 19, wherein the nucleotide sequence is at least 95% identical to SEQ ID NO:2 or SEQ ID NO:9.

22. An isolated nucleic acid comprising a sequence that encodes a polypeptide the amino acid sequence of which is at least 60% identical to SEQ ID NO:1 or SEQ ID NO:10, wherein the polypeptide contains at least one bromodomain and binds to a protein selected from the group consisting of hSNF2H, hSNF2L, and NCoA-62/Skip.

23. The isolated nucleic acid of claim 22, wherein the amino acid sequence is at least 80% identical to SEQ ID NO:1 or SEQ ID NO:10.

24. The isolated nucleic acid of claim 22, wherein the amino acid sequence is at least 95% identical to SEQ ID NO:1 or SEQ ID NO:10.

25. The isolated nucleic acid of claim 16, wherein the number of conservative amino acid substitutions is 0 to 3.

26. The isolated nucleic acid of claim 19, wherein the nucleotide sequence is at least 80% identical to SEQ ID NO:2 or SEQ ID NO:9.

27. A vector comprising the nucleic acid of claim 16.

28. A vector comprising the nucleic acid of claim 19.

29. A vector comprising the nucleic acid of claim 22.

30. A cultured host cell comprising the nucleic acid of claim 16.

31. A cultured host cell comprising the nucleic acid of claim 19.

32. A cultured host cell comprising the nucleic acid of claim 22.

33. A method of producing a polypeptide, the method comprising culturing the cultured host cell of claim 30 in a culture, expressing the polypeptide encoded by the nucleic acid in the cultured host cell, and isolating the polypeptide from the culture.

34. A method of producing a polypeptide, the method comprising culturing the cultured host cell of claim 31 in a culture, expressing the polypeptide encoded by the nucleic acid in the cultured host cell, and isolating the polypeptide from the culture.

35. A method of producing a polypeptide, the method comprising culturing the cultured host cell of claim 32 in a culture, expressing the polypeptide encoded by the nucleic acid in the cultured host cell, and isolating the polypeptide from the culture.

36. An isolated nucleic acid comprising a strand that hybridizes under stringent conditions to a single stranded probe, the sequence of which probe consists of SEQ ID NO:2 or SEQ ID NO:9 or the complement thereof, wherein the nucleic acid is at least 70% identical to SEQ ID NO:2 or SEQ ID NO:9 wherein the nucleic acid encodes a polypeptide that contains at least one bromodomain and binds to a protein selected from the group consisting of hSNF2H, hSNF2L, and NCoA-62/Skip and wherein the stringent conditions comprise hybridization and washing at 50° in 22×SSC containing 0.1% SDS.

37. The isolated nucleic acid of claim 36, wherein the nucleic acid is at least 80% identical to SEQ ID NO:2 or SEQ ID NO:9.

38. The isolated nucleic acid of claim 36, wherein the nucleic acid is at least 90% identical to SEQ ID NO:2 or SEQ ID NO:9.

39. An isolated nucleic acid comprising a strand that hybridizes under stringent conditions to a single stranded probe, the sequence of which probe consists of SEQ ID NO:2 or SEQ ID NO.9 or the complement thereof, wherein the nucleic acid encodes a polypeptide the amino acid sequence of which is at least 60% identical to SEQ ID NO:1 or SEQ ID NO:10 and contains at least one bromodomain and binds to a protein selected from the group consisting of hSNF2H, hSNF2L, and NCoA-62/Skip, and wherein the stringent conditions comprise hybridization and washing at 50° C. in 2×SSC containing 0.1% SDS.

40. The isolated nucleic acid of claim 38, wherein the amino acid sequence is at least 80% identical to SEQ ID NO:1 or SEQ ID NO:10.

\* \* \* \* \*